US008431379B2

(12) United States Patent
Thompson et al.

(10) Patent No.: US 8,431,379 B2
(45) Date of Patent: Apr. 30, 2013

(54) THERMAL AND ACID TOLERANT BETA XYLOSIDASES, ARABINOFURANOSIDASES, GENES ENCODING, RELATED ORGANISMS, AND METHODS

(75) Inventors: David N. Thompson, Idaho Falls, ID (US); Vicki S. Thompson, Idaho Falls, ID (US); Kastli D. Schaller, Ammon, ID (US); William A. Apel, Jackson, WY (US); David W. Reed, Idaho Falls, ID (US); Jeffrey A. Lacey, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 242 days.

(21) Appl. No.: 12/802,911

(22) Filed: Jun. 15, 2010

(65) Prior Publication Data

US 2010/0311110 A1 Dec. 9, 2010

Related U.S. Application Data

(63) Continuation-in-part of application No. 12/321,636, filed on Jan. 23, 2009, now Pat. No. 7,923,234.

(60) Provisional application No. 61/023,639, filed on Jan. 25, 2008.

(51) Int. Cl.
*C12N 9/24* (2006.01)
(52) U.S. Cl.
USPC .............................................. 435/200; 435/15
(58) Field of Classification Search .................. 435/193, 435/200
See application file for complete search history.

(56) References Cited

U.S. PATENT DOCUMENTS

| 4,237,226 | A | 12/1980 | Grethlein |
| 4,581,333 | A | 4/1986 | Kourilsky et al. |
| 4,624,922 | A | 11/1986 | Horikoshi et al. |
| 5,098,825 | A | 3/1992 | Tchen et al. |
| 5,882,905 | A | 3/1999 | Saha et al. |
| 5,916,795 | A | 6/1999 | Fukunaga et al. |
| 5,948,667 | A | 9/1999 | Cheng et al. |
| 6,083,733 | A | 7/2000 | Gronberg et al. |
| 6,268,197 | B1 | 7/2001 | Schulein et al. |
| 6,426,211 | B1 | 7/2002 | De Buyl et al. |
| 6,506,585 | B2 | 1/2003 | Danielsen et al. |
| 6,777,212 | B2 | 8/2004 | Asakura et al. |
| 6,833,259 | B2 | 12/2004 | Bhosle et al. |
| 7,727,755 | B2 | 6/2010 | Thompson et al. |
| 2003/0134395 | A1 | 7/2003 | Shetty |
| 2003/0233675 | A1 | 12/2003 | Cao et al. |
| 2004/0029129 | A1 | 2/2004 | Wang et al. |
| 2005/0112742 | A1 | 5/2005 | Thompson et al. |
| 2006/0105442 | A1 | 5/2006 | Wu et al. |
| 2006/0211083 | A1 | 9/2006 | Katzen et al. |
| 2007/0082381 | A1 | 4/2007 | Wilting et al. |
| 2007/0134778 | A1 | 6/2007 | Benning et al. |
| 2007/0148728 | A1 | 6/2007 | Johnson et al. |
| 2009/0203107 | A1 | 8/2009 | Thompson et al. |
| 2009/0215168 | A1 | 8/2009 | Lee et al. |
| 2009/0221049 | A1 | 9/2009 | Shaw et al. |
| 2009/0226978 | A1 | 9/2009 | Thompson et al. |
| 2009/0253205 | A1 | 10/2009 | Thompson et al. |
| 2009/0263859 | A1 | 10/2009 | Thompson et al. |
| 2009/0269827 | A1 | 10/2009 | Thompson et al. |
| 2010/0203583 | A1 | 8/2010 | Thompson et al. |
| 2010/0311110 | A1 | 12/2010 | Thompson et al. |
| 2011/0081683 | A1 | 4/2011 | Thompson et al. |
| 2011/0275135 | A1 | 11/2011 | Lee et al. |
| 2012/0015407 | A1 | 1/2012 | Thompson et al. |

FOREIGN PATENT DOCUMENTS

| DE | 197 17 893 A1 | 1/1999 |
| WO | 81/00577 | 3/1981 |
| WO | 99/06584 A1 | 2/1999 |
| WO | 03/068926 | 8/2003 |
| WO | 2005/066339 | 7/2005 |
| WO | 2006/117247 A1 | 11/2006 |

OTHER PUBLICATIONS

International Search Report of the International Searching Authority for PCT/US06/42566, dated Jul. 25, 2008.
PCT International Preliminary Report on Patentability of the International Search Authority for PCT/US09/32333, dated Aug. 3, 2010.
PCT International Preliminary Report on Patentability of the International Searching Authority for PCT/US09/00442, dated Jul. 27, 2010.
PCT International Preliminary Report on Patentability of the International Searching Authority for PCT/US09/34701, dated Aug. 24, 2010.
PCT International Preliminary Report on Patentability of the International Searching Authority for PCT/US09/35275, dated Aug. 31, 2010.
PCT International Preliminary Report on Patentability of the International Searching Authority for PCT/US09/35331, dated Aug. 31, 2010.
PCT International Preliminary Report on Patentability of the International Search Authority for PCT/US09/35307, mailed Jan. 25, 2011.
PCT International Search Report of the International Search Authority for PCT/US10/25521 Jul. 14, 2010.
Extended Supplementary European Search Report for EP 09 70 9191, dated Mar. 29, 2012, 6 pages.
Schwarz, Wolfgang H., "A list of cellulolytic bacteria," Technische Universitat Munchen, Apr. 24, 2003, 8 pages.
Simpson et al., "An extremely Thermostable xylanase from the thermophilic eubacterium *Thermotoga*," Biochem. J. (1991) 277, 413-417.
Smook, G.A., "Handbook for Pulp & Paper Technologists," Tappi Pr; 2nd Ed. (Jun. 1992) pp. 65-88.

(Continued)

*Primary Examiner* — Tekchand Saidha
(74) *Attorney, Agent, or Firm* — TraskBritt

(57) ABSTRACT

Isolated and/or purified polypeptides and nucleic acid sequences encoding polypeptides from *Alicyclobacillus acidocaldarius* and variations thereof are provided. Further provided are methods of at least partially degrading xylotriose, xylobiose, and/or arabinofuranose-substituted xylan using isolated and/or purified polypeptides and nucleic acid sequences encoding polypeptides from *Alicyclobacillus acidocaldarius* and variations thereof.

11 Claims, 13 Drawing Sheets

OTHER PUBLICATIONS

Subramaniyan et al., "Cellulase-free xylanases from *Bacillus* and other microorganisms," FEMS Microbiology Letters 183 (2000) 1-7.

Sunna et al., "Glycosyl hydrolases from hyperthermophiles," Extremophiles (1997) 12-13.

Techapun et al., "Production of a cellulose-free xylanase from agricultural waste materials by a thermotolerant *Streptomyces* sp.," Biotechnology Letters 23: 1685-1689, 2001.

Thompson et al., "Comparison of Pretreatment Methods on the Basis of Available Surface Area," Bioresource Technology 39 (1992) 155-163.

Thompson et al., "In Vitro Degradation of Natural Insoluble Lignin in Aqueous Media by the Extracellular Peroxidases of Phanerochaete chrysosporium," 1998 John Wiley & Sons, Inc. pp. 704-717.

Thompson et al., "Measurement of fumonsins in corn with a fiber-optic fluoroimmunosensor," SPIE vol. 2980, (2010) pp. 532-538.

Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.

Thompson et al., "Purification and Characterization of a Novel Thermo-Alkali-Stable Catalase from *Thermus brockianus*," Biotechnol. Prog. 2003, 19, 1292-1299.

Thompson et al., "Thermoacidophilic Cellulases and Hemicellulases from *Alicyclobacillus acidocaldarius*," Idaho National Laboratory, 2006, 1 page.

Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.

Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.

Turner et al., "Potential and utilization of thermophiles and thermostable enzymes in biorefining," Microbial Cell Factories, Biomed Central, London, NL, vol. 6, No. 1, Mar. 15, 2007, p. 9.

Uhl et al., "The first description of an archaeal hemicellulase: the xylanase from *Thermococcus zilligii* strain AN1," Extremophiles (1999) 3:263-267.

Viikari et al., "Xylanases in bleaching: From an idea to the industry," FEMS Microbiology Reviews 13 (1994) 335-350.

Walseth, Curtis S., Occurrence of Cellulases in Enzyme Preparations from Microorganisms, TAPPI vol. 35, No. 5, May 1952, pp. 228-233.

Ward et al., "Characterization of a new bacteriophage which infects bacteria of the genus *Acidiphilium*," Journal of General Virology (1993) 74: 2419-2425.

Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.

Wright et al., "Ethanol from Biomass by Enzymatic Hydrolysis," Chemical Engineering Progress, Aug. 1988, pp. 62-74.

Yuan et al., Expression of acidophilic alpha-amylase from *Alicyclobacillus acidocaldarius*, Sheng Wu Gong Cheng Xue Bao, Jan. 2005, 21(1):78-83. Abstract only.

Database UniProt [Online]. Feb. 10, 2009. XP-002674095. Database accession No. B7DM51, 1 page.

Extended Supplementary European Search Report for EP 09 75 5307, dated Apr. 18, 2012, 4 pages.

GenBank: AJ252161.1 *Alicyclobacillus acidocaldarius* maltose/maltodextrine transport gene region(maIEFGR genese, cdaA gene and glcA gene), NCBI, Hulsmann, A. http://www.ncbi.nlm.nih.gov/nuccore/AJ252161 (Jan. 6, 2000).

Barany, F., 1911, PNAS. USA, 88: 189-193.

Bertoldo et al., 2004, Eng. Life Sci., 4, No. 6.

BLAST Search of Seq. ID. 36, accessed Apr. 22, 2009, 54 pages.

BLAST Search of Seq. ID. 456, accessed Apr. 22, 2009, 48 pages.

BLAST Search of Seq. ID. 458, accessed Apr. 22, 2009, 59 pages.

BLAST Search of Seq. ID. 460, accessed Apr. 22, 2009, 37 pages.

BLAST Search of Seq. ID. 462, accessed Apr. 22, 2009, 35 pages.

BLAST Search of Seq. ID. 464, accessed Apr. 22, 2009, 45 pages.

Borman, S., 2006, Glycosylation Engineering. Chem. Eng. News, 84(36): 13-22.

Broun et al. "Catalytic Plasticity of Fatty Acid Modification Enzymes Underlying Chemical Diversity of Plant Lipids" Science vol. 282 Nov. 13, 1998 pp. 1315-1317 (4 pages).

Buckholz, R. G., 1993, Yeast systems for the expression of heterologous gene products. Curr. Op. Biotechnology 4: 538-542.

Burg, J. L. et al., 1996, Mol. and Cell. Probes, 10: 257-271.

Chu, B. C. F. et al., 1986, NAR, 14: 5591-5603.

Collins et al., "Xylanaes, Xylanase Families and Extremophilic Xylanses," FEMS Microbiology Review, 2005, pp. 3-23.

Devos et al. "Practical Limits of Functiona Prediction" Proteins: Structure, Function, and Genetics 41 (2000) pp. 98-107 (10 pages).

Duck, P. et al., 1990, Biotechniques, 9: 142-147.

Eckert et al., "A Thermoacidophilic Endoglucanase (CeIB), etc.," Eur. J. Biochem. 270, 2003, pp. 3593-3602.

Eckert et al., "Gene cloning, sequencing, and characterization of a family 9 endoglucanase (CeIA) with an unusual pattern of activity from the theremoacidophile *Alicyclobacillus acidocaldarius* ATCC27009," Applied Microbiology and Biotechnology, vol. 60, N.

Eckert, Kelvin, "Dissertation, Cloning and Characterization of two glycosidases from the acidothermophile *Alicyclobacillus acidocaldarius* ATCC27009," Berlin, Dec. 18, 1971, 113 pages.

Edwards, C. P., and Aruffo, A., 1993, Current applications of COS cell based transient expression systems. Curr. Op. Biotechnology 4: 558-563.

Erlich, H.A., J Clin. Immunol., Nov. 1989; 9(6):437-47.

Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.

GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2 &tool=Entr.

Guateli, J. C. et al., 1990, PNAS. USA, 87: 1874-1878.

Hamelinck, CN, G van Hooijdonk, and APC Faaij, 2005, Ethanol from lignocellulosic biomass: techno-economic performance in short-, middle-, and long-term, Biomass Bioenergy, 28:384-410.

Hulsmann et al., "Maltose and maltodextrin transport in the thermoacidophilic gram-positive bacterium *Alicyclobacillus acidocaldarius* is mediated by a high-affinity transport system that includes a maltose binding protein tolerant to low pH," J. Bacterio.

Huygen, K. et al., 1996, Nature Medicine, 2(8): 893-898.

International Application Published Under the Patent Cooperation Treaty, WO 2005/066339, Wilting et al, published Jul. 21, 2005.

International Preliminary Report on Patentability and Written Opinion of the International Searching Authority for PCT/US06/42566 dated Apr. 23, 2009 (7 pages).

International Search Report and Written Opinion of the International Search Authority for PCT/US09/32333, mailed Jun. 19, 2009, 9 pages.

Ito et al., "Purification and properties of acid stable xylanases from *Aspergillus kawachii*," Bioscience Biotechnology and Biochemistry 56 (4):547-550, Apr. 1992.

Jeffries, 1996, Curr. Op. in Biotech., 7:337-342.

Jones et al., "Cloning and transcriptional analysis of the *Thermoanaerobacter ethanolicus* strain 39E maltose ABC transport system," Extremophiles 2002, 6:291-299.

Kievitis, T. et al., 1991, J. Virol. Methods, 35: 273-286.

Kohler, G. et al., 1975, Nature, 256(5517): 495497.

Kwoh, D. Y. et al., 1989, PNAS. USA, 86: 1173-1177.

Lauro et al., "Isolation and characterization of a new family 42 beta-galactosidase from the *Thermoacidophilic bacterium Alicyclobacillus acidocaldarius*: Identification of the active site residues," Biochimica et Biophysica Acta 1784 (2008) 292-301.

Lavarack et al., "The acid hydrolysis of sugarcane begasse hemicellulose to produce xylose, arabinose, glucose and other products," Biomass and Bioenergy 23 (2002) 367-380.

Liu C, and CE Wyman, 2003, The effect of flow rate of compressed hot water on xylan, lignin, and total mass removal from corn stover, Ind. Eng. Chem. Res., 42:5409-5416.

Lucas et al., C4-Dicarboxylate Transporter/Malic Acid Transport Protein [*Alicyclobacillus acidocaldarius* LAA1], GenBank Direct Submission, Accession Number: EED06059, Dec. 17, 2008 (Retrieved from the Internet Dec. 15, 2009: <URL:http://www.ncbl.nlm.nlh.gov/.

Luckow, V. A., 1993, Baculovirus systems for the expression of human gene products. Curr. Op. Biotechnology 4: 564-572.

Lynd et al., 2002, Micro. and Mol. Biol. Rev., vol. 66, No. 3, p. 506-577.

Malherbe and Cloete, 2002, Re/View in Environmental Science and Bio/Technology, 1: 105-114.

Matthews, J. A. et al., 1988, Anal. Biochem., 169: 1-25.

Merrifield, R. D., 1966, J. Am. Chem. Soc., 88(21): 5051-5052.

Miele, E. A. et al., 1983, J. Mol. Biol., 171: 281-295.

Mielenz, 2001, Curr. Op. in Micro., 4:324-329.

Neddleman and Wunsch, J. Mol. Biol. 48: 443 (1970).

Olins, P. O., and Lee, S. C., 1993, Recent advances in heterologous gene expression in *E. coli*. Curr. Op. Biotechnology 4: 520-525.

PCT International Search Report and Written Opinion of the International Searching Authority for PCT/US09/00442, dated May 18, 2009, 8 pages.

PCT International Search Report and Written Opinion of the International Searching Authority for PCT/US09/34701, dated Jan. 12, 2010, 10 pages.

PCT International Search Report and Written Opinion of the International Searching Authority for PCT/US09/35275, dated Feb. 25, 2010, 13 pages.

PCT International Search Report and Written Opinion of the International Searching Authority for PCT/US09/35331, dated Feb. 23, 2010, 10 pages.

PCT International Search Report and Written Opinion of the International Search Authority for PCT/US09/35307, dated Jun. 10, 2010, 10 pages.

PCT International Search Report and Written Opinion of the International Search Authority for PCT/US10/25521, dated Jul. 14, 2010, 12 pages.

Pearson and Lipman, Proc. Natl. Acad. Sci. (U.S.A.) 85: 2444 (1988).

Sanchez-Pescador, R., 1988, J. Clin. Microbiol., 26(10): 1934-1938.

Schafer et al., "X-ray Structures of the Maltose-Maltodextrin-binding Protein of the *Thermoacidophilic Bacterium Alicyclobacillus acidocaldarius* Provide Insight into Acid Stability of Proteins," J. Mol. Biol. 2004, 335:261-274.

Schäffer, C. et al., 2001, Prokaryotic glycosylation. Proteomics, 1: 248-261.

Scheffel et al., "Functional reconstitution of a maltrose ATP-binding cassette transporter from the thermoacidophilic gram-positive bacterium *Alicyclobacillus acidocaldarius*," Biochem Biophy Acta, 2004, 1656(1):57-65.

Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.

Schwermann, B. et al., 1994, Purification, properties and structural aspects of a thermoacidophilic a-amylase from *Alicyclobacillus acidocaldarius* ATCC 27009, insight into acidostability of proteins. Eur. J. Biochem. 226: 981-991.

Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).

Shallom et al., "Microbial hemicellulases," Current Opinion in Microbiology, Current Biology Ltd, GB, vol. 6, No. 3, Jun. 1, 2003, pp. 219-228.

Supplemental European Search Report for EP 06 82 7231, dated Nov. 12, 2009, 6 pages.

Tsao, GT, MR Ladisch, and HR Bungay, 1987. Biomass Refining, In Advanced Biochemical Engineering, Wiley Interscience, N.Y., 79-101.

Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].

UniProtKB/TrEMBL Q9JRQ1 [online]. Oct. 1, 2000. Available on the internet at <<URL://http://www.uniprot.org/uniprot/Q9JRQ1>>.

Upreti et al., 2003, Bacterial glycoproteins: Functions, biosynthesis and applications. Proteomics, 3: 363-379.

Urdea, M. S., 1988, Nucleic Acids Research, II: 4937-4957.

Vieille and Zeikus, 2001, Micro. and Mol. Biol. Rev., vol. 65, No. 1, p. 1-43.

Walker, G. T. et al., 1992, NAR 20: 1691-1696.

Walker, G.T. et al., 1992, PNAS. USA, 89:392-396.

Whisstock et al. "Prediction of Protein Function from Protein Sequence and Structure" Quarlty Reviews of Biophysics 36, 3 (2003) pp. 307-340 (35 pages).

Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).

Bork, Peer, "Powers and Pitfalls in Sequence Analysis: The 70% Hurdle," Genome Research, 2000, 10:398-400.

Bowie et al., "Deciphering the Message in Protein Sequences: Tolerance to Amino Acid Substitutions," Science, 1990, 247:1306-1310.

Lau et al., "PCR ligation mutagenesis in transformable streptococci: application and efficiency," Journal of Microbiological Methods 49 (2002) 193-205.

Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.

Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).

Badger, P.C., "Ethanol from cellulose: A general review," In: J. Janick and A. Whipkey (eds.), Trands in new crops and new uses. ASHA Press, Alexandria, VA, 2002, pp. 17-21.

Bailey et al., "Interlaboratory testing of methods for assay of xylanase activity," Journal of Biotechnology, 23 (1992) 257-270.

Bergquist et al., "Molecular diversity of thermophilic cellulolytic and hemicellulolytic bacteria," FEMS Microbiology Ecology 28 (1999) 99-110.

Cowling, Ellis B., "Physical and Chemical Constrains in the Hydrolysis of Cellulose and Lignocellulosic Materials," Biotechnol. & Bioeng. Symposium No. 5, 163-181 (1975).

Crout et al., "Glycosidases and glycosyl transferases in glycoside and oligosaccharide synthesis," Current Opinion in Chemical Biology, Current Biology LTD, London, GB, vol. 2, No. 1, Feb. 1, 1998, pp. 98-111.

Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.

Database UniProt [Online]. Feb. 10, 2009. XP-000002659383. Database accession No. B7DT70, 1 page.

Ehrman, Tina, "Standard Method for Determination of Total Solids in Biomass," Chemical Analysis and Testing Task, Laboratory Analytical Procedure, Oct. 28, 1994, 242 total pages.

EMBL Submission CP001728, Sep. 2009. [Retrieved from the internet: URL:http://www.ebi.ac.uk/Tools/dbfetch/embifetch?style=html&id=CP001728&Submit=Go], 51 pages.

Extended Supplementary European Search Report for EP 09 82 3952, dated Sep. 20, 2011, 7 pages.

Fan et al., "The Nature of Lignocellulosics and Their Pretreatments for Enzymatic Hydrolysis," Advances in Biochemical Engineering/Biotechnology, 1982, vol. 23/1982, 157-187.

Flanagan, et al., "Development of gas phase bioreactors for the removal of nitrogen oxides from synthetic flue gas streams," Fuel 81 (2002) 1953-1961.

Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.

Gessesse, Amare, "Purification and Properties of Two Thermostable Alkaline Xylanases from an *Alkaliphilic bacillus* sp.," Applied and Environmental Microbiology, Sept. 1998, pp. 3533-3535.

Glenn et al., "Transformation of Acidiphilium by electroporation and conjugation," Can J Microbiol. May 1992;38 (5):387-93.

Goldstein et al., "The Hydrolysis of Cellulose with Superconcentrated Hydrochloric Acid," Biotechnology and Bioengineering Symp. No. 13, pp. 17-25 (1983).

Grassin et al., "Chapter 2.13, Fruit Juices," (T. Godfrey and S. West, eds.), Industrial Enzymology, 2nd Ed., pp. 227-264 (1996).

Grethlein, H. E., "Pretreatment for enhanced hydrolysis of cellulosic biomass," Biotechnol. Adv. 1984. 2:43-62.

Grethlein, Hans E., "Comparison of the Economics of Acid and Enzymatic Hydrolysis of Newsprint," Biotechnology and Bioengineering, vol. XX, pp. 503-525 (1978).

Hanselmann, K.W., "Lignochemicals," Experientia 38 (1982) pp. 176-189.

Houghton et al., "Fungal Upgrading of Wheat Straw for Straw-Thermoplastics Production," Applied Biochemistry and Biotechnology, vol. 113-116, 2004, pp. 71-93.

Keller et al., "Microbial Pretreatment of Biomass: Potential for Reducing the Severity of Thermochemical Biomass Pretreatment," Applied Biochemistry and Biotechnology, vol. 105-108, 2003.

Kenealy et al., "Rapid 2,2-bicinchoninic-based xylanase assay compatible with high throughput screening," Biotechnology Letters 25: 1619-1623, 2003.

Knappert et al., "Partial Acid Hydrolysis of Cellulosic Materials as a Pretreatment for Enzymatic Hydrolysis," Biotechnology and Bioengineering, vol. XXII, pp. 1449-1463 (1980).

Kulkarni et al., "Molecular and biotechnological aspects of xylanases," FEMS Microbiology Reviews 23 (1999) 411-456.

Lauro et al., "Characterization of a β-glycosidase from the thermoacidophilic bacterium *Alicyclobacillus acidocaldarius*," Extremophiles (2006) 10:301-310.

Lee et al., "Oxygen Effects on Thermophilic Microbial Populations in Biofilters Treating Nitric Oxide Containing Off-Gas Streams," Environmental Progress, vol. 20, No. 3, Oct. 2001.

Lynd, Lee R., "Overview and Evaluation of Fuel Ethanol from Cellulosic Biomass: Technology, Economics, the Environment, and Policy," Annu. Rev. Energy Environ. 1996, 21:403-65.

MacKenzie et al., "Multiple Chromosomes in Bacteria: The Yin and Yang of trp Gene Localization in *Rhodobacter sphaeroides* 2.4.1," Genetics 153: 525-538 (Oct. 1999).

Manchenko, Gennady P., "Handbook of Detection of Enzymes on Electrophoretic Gels," CRC Press, Inc. 1994, pp. 220-240.

McCoy, Michael, "Chemical Makers Try Biotech Paths," Chemical Engineering News, Jun. 22, 1998, pp. 13-19.

Michel et al., "Specificity of the protein secretory apparatus: secretion of the heat-labile enterotoxin B subunit pentamers by different species of Gram bacteria," Gene 152 (1995) pp. 41-45.

Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.

Ng et al., 1981, Applied and Environmental Microbiology, 41(6):1337-1343.

Ohta et al., "Purification and Characterization of an Acidophilic Xylanase from *Aureobasidium pullulans* var. melanigenum and Sequence Analysis of the Encoding Gene," Journal of Bioscience and Bioengineering, vol. 92, No. 3, 262-270, 2001.

Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.

Pajunen et al., Microbiology (2005) 151, 1209-1218.

Patel et al., (2006), "Medium and long-term opportunities and risks of the biotechnological production of bulk chemicals from renewable resources: The potential of white biotechnology". The BREW Project. Final Report prepared under the European Commission's GROWTH Programme (DG Research), (publica.fraunhofer.de/eprints/N-48834.pdf).

PCT International Search Report and Written Opinion of the International Searching Authority for PCT/US10/51095, dated Dec. 2, 2010, 11 pages.

PCT International Search Report and Written Opinion of the International Search Authority for PCT/US11/34852, dated Oct. 21, 2011, 12 pages.

Perlack et al., "Biomass as Feedstock for a Bioenergy and Bioproducts Industry: The Technical Feasibility of a Billion-Ton Annual Supply," USDA and DOE, Apr. 2005, 78 pages.

Peyton et al., "Biotransformation of Toxic Organic and Inorganic Contaminants by Halophilic Bacteria," Halophilic Microorganisms, Antionio Ventosa (Ed.), Springer, 2004, pp. 315-331.

Ragauskas et al., "The Path Forward for Biofuels and Biomaterials," Science, Jan. 27, 2006, vol. 311, pp. 484-4589.

Ramos et al., "Biomechanical and Biochemical Pulping of Sugarcane Bagasse with *Ceriporiopsis subvermispora* Fungal and Xylanase Pretreatments," J. Agric. Food Chem. 2001, 49, 1180-1186.

Saeman et al., "Quantitative Saccharification of Wood and Cellulose," Industrial and Engineering Chemistry, Jan. 1945, vol. 17, No. 1, pp. 35-37.

Saha et al., "Dilute Acid Pretreatment, Enzymatic Saccharification, and Fermentation of Rice Hulls to Ethanol," Biotechnol. Prog. 2005, 21, 816-822.

Sa-Pereira et al., "Rapid production of thermostable cellulose-free xylanase by a strain of *Bacillus subtilis* and its properties," Enzyme and Microbial Technology, 30 (2002) 924-933.

Schell et al., "Dilute-Sulfuric Acid Pretreatment of Corn Stover in Pilot-Scale Reactor," Applied Biochemistry and Biotechnology, vol. 105-108, 2003, pp. 69-85.

Lin et al., "Purification, Characterization, and Gene Cloning of Thermopsin, a Thermostable Acid Protease from *Sulfolobus acidocaldarius*," The Journal of Biological Chemistry, 1990, vol. 265, No. 3, pp. 1490-1495.

Bhatia et al., "Microbial beta-Glucosidases: Cloning, Properties, and Applications," Critical Reviews in Biotechnology, 22(4):375-407, Jan. 1, 2002.

Breves et al., "Genes Encoding Two Different beta-Glucosidases of *Thermoanaerobacter brockii* Are Clustered in a Common Operon," Applied and Environmental Microbiology, vol. 63, No. 10, Oct. 1997, pp. 3902-3910.

Database EMBL [Online]. Mar. 16, 2007. XP-002627757. Database accession No. ER073884, 1 page.

Database Geneseq [Online]. May 21, 1998. XP-002627734. Database accession No. AAW35004, 1 page.

Database UniProt [Online]. May 1, 1997. XP-002630045. Database accession No. P96090, 1 page.

Database UniProt [Online]. Oct. 1, 2001. XP-002627736. Database accession No. Q97UI4, 1 page.

Database UniProt [Online]. Jun. 26, 2007. XP-002627735. Database accession No. A5IKZ4, 1 page.

Database UniProt [Online]. Nov. 3, 2009. XP-002627733. Database accession No. C8WTP2, 1 page.

Extended Supplementary European Search Report for EP 09 70 3173, dated Apr. 20, 2011, 7 pages.

Extended Supplementary European Search Report for EP 10 74 6882, dated Aug. 27, 2012, 9 pages.

FIG. 1A

```
148269983    1                      MELYRDPSQPIEVRVRDLLSRMT
15642851     1                      MELYRDPSQPIEVRVRDLLSRMT
RAAC00307    1   MNVKAASAPDEQRRLPVTPVYLDPAQSIEARVDALLADMT
76795911     1                  MTPLYLDSTQSVEKRVEDLLQQMT
15899739     1                            MTAIKSLLNQMS
116621797    1         MPRPAKIEPYRNPALPPAKRAKDLLSHMT 148269983   24   LEEKAAQLGSVW...GYELIDERGKFSREKAKELLK..NG
15642851    24   LEEKVAQLGSVW...GYELIDERGKFSREKAKELLK..NG
RAAC00307   41   LEEKVAQLTSIW...AFEVLDEL.EFSAEKAAAVLG..QG
76795911    25   IEEKVAQLNSIW...VYEILDDM.KFSFDKAKRLMS..YG
15899739    13   IEEKIAQLQAIP...IDALMEGK.EFSEEKARKYLK..LG
116621797   30   LEEKAAQMMCVWQQKADTLVDADGRFDPEKARKAFKDRRG 148269983   59   IGQVTRPGGS.TNLEPQEAAELVNEIQRFLVEETRLGIPA
15642851    59   IGQITRPGGS.TNLEPQEAAELVNEIQRFLVEETRLGIPA
RAAC00307   75   IGQVTRIGGA.TNLDPPDVARLANQIQRYLRDHTRLGIPA
76795911    59   IGQITRLGGA.SNLSPRETVRIANQIQKFLIENTRLGIPA
15899739    47   IGQITRVAGSRLGLKPKEVVKLVNKVQKFLVENTRLKIPA
116621797   70   LGQVGRPSDAGKGQDARGMAELTNAIQKFFIENSRLGIPV 148269983   98   MIHEECLTGYMGLGGTNFPQAIAMASTWDPDLIEKMTTAI
15642851    98   MIHEECLTGYMGLGGTNFPQAIAMASTWDPDLIEKMTTAV
RAAC00307  114   LIHEESCSGYMAKGATCFPQTIGIASTWDVDLARRIGAII
76795911    98   LIHEESCSGYMAKGATIFPQTIGVASTWNNEIVEKMASVI
15899739    87   IIHEECLSGLMGYSSTAFPQAIGLASTWNPELLTNVASTI
116621797  110   IFHEECLHGHAAIGGTSFPQPIGLGATFDPELVESLFAMT 148269983  138   REDMRKIGAHQGLAPVLDVARDPRWGRTEETFGESPYLVA
15642851   138   REDMRKIGAHQGLAPVLDVARDPRWGRTEETFGESPYLVA
RAAC00307  154   RDQMRAVGARQALAPLLDVARDPRWGRVEETFGEDPYLVA
76795911   138   REQMKAVGARQALAPLLDITRDPRWGRTEETFGEDPYLVM
15899739   127   RSQGRLIGVNQCLSPVLDVCRDPRWGRCEETYGEDPYLVA
116621797  150   AAEARARGTHQALTPVVDVAREPRWGRVEETYGEDPFLVS 148269983  178   RMGVSYVKGLQGED...IKKGVVATVKHFAGYSASEGGKN
15642851   178   RMGVSYVKGLQGED...IKKGVVATVKHFAGYSASEGGKN
RAAC00307  194   QMGIAYVRGLQGDD...LSQGVMATGKHFVGYGASEGGMN
76795911   178   RMGVSYIRGLQTES...LKEGIVATGKHFVGYGNSEGGMN
15899739   167   SMGLAYITGLQG......ETQLVATAKHFAAHGFPEGGRN
116621797  190   RMGIAAVRGFQGDATFRDKTRVIATLKHFAAHGQPESGTN 148269983  215   WAPTNIPEREFKEVFLFPFEAAVKEANVLSVMNSYSEIDG
15642851   215   WAPTNIPEREFKEVFLFPFEAAVKEANVLSVMNSYSEIDG
RAAC00307  231   WAPAHIPERELREVYLFPFEAAVREAGLGAIMPGYHELDG
76795911   215   WAPAHIPERELREVFLYPFEAAVKEAKLSSIMPGYHELDG
15899739   201   IAQVHVGNRELRETFLFPPFEVAVKIGKVMSIMPAYHEIDG
116621797  230   CAPVNVSMRVLRETFLFPFKEALDKGCAISVMASYNEIDG
```

FIG. 1B

```
148269983   255 VPCAANRKLLTDILRKDWGFKGIVVSDYFAVKVLEDY...
15642851    255 VPCAANRKLLTDILRKDWGFEGIVVSDYFAVKVLEDY...
RAAC00307   271 VPCHDNPGLLRETLRGRWGFQGLVVSDYFAVNQLFEY...
76795911    255 VPCHKSKKLLNDILRKDWGFEGIVVSDYFAISQLYEY...
15899739    241 VPCHGNPQLLTNILRQEWGFDGIVVSDYDGIRQLEAI...
116621797   270 VPSHASRWLLRDVLRKEWGFKGFVVSDYYAIYELSYRPES 148269983   292 ..HRIARDKSEAARLALEAGIDVELPKTECY.QYLKDLVE
15642851    292 ..HRIARDKSEAARLALEAGIDVELPKTECY.QYLKDLVE
RAAC00307   308 ..HQVARDKAEAAALAVRAGVDVELPTRDVYGKPLIEAVA
76795911    292 ..HHVTSDKKGAAKLALEAGVDVELPSTDYYGLPLRELIE
15899739    278 ..HKVASNKMEAAILALESGVDIEFPTIDCYGEPLVTAIK
116621797   310 HGHFVAKDKREACALAVQAGVNIELPEPDCY.LHLVDLVH 148269983   329 KGIISEALIDEAVARVLRLKFMLGLFENPYVEVEKAK...
15642851    329 KGIISEALIDEAVTRVLRLKFMLGLFENPYVEVEKAK...
RAAC00307   346 RGLVSPAEIDELVRRVLTWKFRLGLFDHPFVDEGAAIAVF
76795911    330 SGEIDIDFVNEAVKRVLKIKFELGLFENPYINEEKAVEIF
15899739    316 EGLVSEAIIDRAVERVLRIKERLGLLDNPFVDESAVPERL
116621797   349 KGVLQESQLDELVEPMLRWKFQMGLFDDPYVDPAEAERIA 148269983   366 .IESHKDIALDIARKSIILLKNDG.ILPLQK..NKKVALI
15642851    366 .IESHRDIALEIARKSIILLKNDG.ILPLQK..NKKVALI
RAAC00307   386 DNAEQRQVAREAAEKSMVLLKNDG.LLPLAP..RGTIAVI
76795911    370 DTNEQRELAYKIAQESIVLLKNENNLLPLKKD.LKSIAVI
15899739    356 DDRKSRELALKAARESIVLLKNENNMLPLSKN.INKIAVI
116621797   389 GCDAHRELAMQAARETITLLKNDGPVVPLDLSAIKTIAVI 148269983   402 GPNAGEVRNLLGDYMYLAHIRALLDNID..DVFGNPQIPR
15642851    402 GPNAGEVRNLLGDYMYLAHIRALLDNID..DVFGNPQIPR
RAAC00307   423 GPNAHTTRNLVGDYAYPCHIESLLEQSE.DNVFQTP.LPS
76795911    409 GPNADSIRNMIGDYAYPCHIESLLEMRETDNVFNTP.LPE
15899739    395 GPNANDPRNMLGDYTYTGHLN...................
116621797   429 GPNAN..RSLLGGYS.........................

148269983   440 ENYERLKKSIEEHMKSIPSVLDAFKEEGIEFEYAKGCEVT
15642851    440 ENYERLKKSIEEHMKSIPSVLDAFKEEGIEFEYAKGCEVT
RAAC00307   461 G...VKHVDEFILMRTILEAIRHRVGSEAQVVYAKGCDIL
76795911    448 S...LEAKDIYVPIVTVLQGIKAKVSSNTEVLYAKGCDVL
15899739    416 .......IDSGIEIVTVLQGIAKKVGE.GKVLYAKGCDIA
116621797   442 ........GVPKHDVTVLDGIRERVGSRAKVVYAEGCKIT 148269983   480 G..............EDRSGFEEAIEIAKKSDVAIVVVG
15642851    480 G..............EDRSGFEEAIEIAKKSDVAIVVVG
RAAC00307   498 G..............GEDAELEEAVALAAKADVAVVVVG
76795911    485 N..............NSKDGFKEAVEIAKQADVAVVVVG
15899739    448 G..............ESKEGFSEAIEIAKQADVIIAVMG
116621797   474 IGGSWVQDEVTPSDPAEDRRQIAEAVKVAKRADVIVLAIG
```

FIG. 1C

```
148269983  505  DKSGLTLDCT...............TGESRDMANLKLPGVQ
15642851   505  DKSGLTLDCT...............TGESRDMANLKLPGVQ
RAAC00307  523  DRAGLTDACT...............TGESRDRATLSLIGRQ
76795911   510  DKSGLTDGCT...............SGESRDRADLNLPGVQ
15899739   473  EKSGLPLSWTDIPSEEEFKKYQAVTGEGNDRASLRLLGVQ
116621797  514  GNEQTSREAWS..............PKHLGDRPSLDLVGRQ 148269983  531  EELVLEVAKTGKPVVLVLITGRPYSLKNVVDKVNAILQVW
15642851   531  EELVLEVAKTGKPVVLVLITGRPYSLKNVVDKVNAILQVW
RAAC00307  549  EELVRRVIATGTKTVVVLVSGRPLAIPDIAERANAVLEAW
76795911   536  EELIKAIYETGTPVIVVLINGRPMSISWIAEKIPAIIEAW
15899739   513  EELLKELYKTGKPIILVLINGRPLVLSPIINYVKAIIEAW
116621797  541  EELVRAMVATGKPVIAFLFNGRPISINYLAQSVPAIFECW 148269983  571  LPGEAGGRAIVDIIYGKVNPSGKLPISFPRSAGQIPVFHY
15642851   571  LPGEAGGRAIVDIIYGKVNPSGKLPISFPRSAGQIPVFHY
RAAC00307  589  LPGEEGAEAVAAVLFGDVNPSGKLPITIPRSVGQVPIYYG
76795911   576  LPGEEGGRAVADVIFGDYNPGGKLPISIPQSVGQLPVYYY
15899739   553  FPGEEGGNAIADIIFGDYNPSGRLPITFPMDTGQIPLYYS
116621797  581  YLGQETGRAVAEVLFGDTNPGGKLPITIPRSAGHLPAFYN 148269983  611  VKPSGGRSHWHGDYVDESTKPLFPFGHGLSYTKFEYSNLR
15642851   611  VKPSGGRSHWHGDYVDESTKPLFPFGHGLSYTKFEYSNLR
RAAC00307  629  HKPSGGRSHWKGAYVDESNLPLYPFGHGLSYTAFAYRDLA
76795911   616  HKPSGGRSHWKGDYVELSTKPLYPFGYGLSYTEFSYTNLN
15899739   593  RKPSSFR.....PYVMLHSSPLFTFGYGLSYTQFEYSNLE
116621797  621  HKPSARR.....GYLFDEVGPLYAFGYGLSYTTFAFQNLR 148269983  651  IEPKEVPPAG.EVVIKVDVENTGDRDGDEVVQLYIGREFA
15642851   651  IEPKEVPPAG.EVVIKVDVENIGDRDGDEVVQLYIGREFA
RAAC00307  669  LSPSVLGVHG.EVEVSCVIENVGARAGEEVVQLYARDVAA
76795911   656  ISNRKVSLRDRMVEISVDIKNTGTLKGDEVVQLYIHQEAL
15899739   628  VTPKEVGPLS.YITILLDVKNVGNMEGDEVVQLYISKSFS
116621797  656  LAKKKMHRES.TARVLVDVTNTGAREGREVVQLYIRDLVS 148269983  690  SVTRPVKELKGFKRVSLKAKEKKTVVFRLHMDVLAYYDRD
15642851   690  SVTRPVKELKGFKRVSLKAKEKKTVVFRLHMDVLAYYNRD
RAAC00307  708  DVTRPVKALCGFARVALAPGEKARVRFRVSAHQFGFYNRE
76795911   696  SVTRPVKELKGFKRITLDAGEEKTVIFKLSIEQLGFYDEN
15899739   667  SVARPVKELKGFAKVHLKPGEKRRVKFALPMEALAFYDNF
116621797  695  SVTRPIKELKGFRKITLQPGQTQTVEFEITPDLLAFYNVD 148269983  730  MKLVVEPGEFKVMVGSSSEDIRLTGSFTVVGEKREVVGMR
15642851   730  MKLVVEPGEFKVMVGSSSEDIRLTGSFSVVGEKREVVGMR
RAAC00307  748  MRYVVEPGEIEFMVGASSEDIRLRGAVRMDGAVTEIEHEK
76795911   736  MEYVVEPGRVDVMIGSSSEDIRLRDYFEIVGEKEKVAKKF
15899739   707  MRLVVEKGEYQILIGNSSENIILKDTFRIK.ETKPIMERR
116621797  735  MKFVVEPGDFEIMVGSSSRDADLQKVILRVE
```

FIG. 1D

```
148269983   770  KFFTEACEE
15642851    770  KFFTEACEE
RAAC00307   788  VYQSAVDVERM
76795911    776  ITEVRVENK
15899739    746  IFLSNVQIE
116621797
```

THERMAL AND ACID TOLERANT BETA XYLOSIDASES, ARABINOFURANOSIDASES, GENES ENCODING, RELATED ORGANISMS, AND METHODS

CROSS-REFERENCE TO RELATED APPLICATIONS

This application is a continuation-in-part of U.S. patent application Ser. No. 12/321,636, filed Jan. 23, 2009, now U.S. Pat. No. 7,923,234, issued Apr. 12, 2011, which application claims the benefit of the filing date of U.S. Provisional Patent Application Ser. No. 61/023,639, filed Jan. 25, 2008, for "THERMAL AND ACID TOLERANT BETA-XYLOSIDASES, GENES ENCODING, RELATED ORGANISMS, AND METHODS," the disclosure of each of which is incorporated herein in its entirety by this reference.

GOVERNMENT RIGHTS

This invention was made with government support under Contract No. DE-ACO7-991D 13727 and Contract No. DE-ACO7-051D 14517 awarded by the United States Department of Energy. The government has certain rights in the invention.

STATEMENT ACCORDING TO 37 C.F.R. §1.52(E)(5)- SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing as submitted.txt" which is 92 KB and created on Jun. 15, 2010.

TECHNICAL FIELD

The present invention relates generally to biotechnology. More specifically, the present invention relates to isolated and/or purified polypeptides and nucleic acid sequences encoding polypeptides from *Alicyclobacillus acidocaldarius* and methods for their use.

BACKGROUND

Dilute acid hydrolysis to remove hemicellulose from lignocellulosic materials is one of the most developed pretreatment techniques for lignocellulose and is currently favored (Hamelinck et al., 2005) because it results in fairly high yields of xylose (75% to 90%). Conditions that are typically used range from 0.5% to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Low temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80° C. to 100° C. It has also been demonstrated that the sugars produced in low temperature acid hydrolysis are stable under those same conditions for at least 24 hours with no detectable degradation to furfurals and related decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second lower severity acid hydrolysis step (Garrote et al., 2001).

Other acidic pretreatment methods include autohydrolysis and hot water washing. In autohydrolysis, biomass is treated with steam at high temperatures (~200° C.), which cleaves acetyl side chains associated with hemicellulose to produce acetic acid that functions as the acid catalyst in an acid hydrolysis. Because acetic acid is a much weaker acid than sulfuric acid, at temperatures below 240° C. the hemicellulose is not completely hydrolyzed to sugar monomers and has high levels of oligomers (Garrote et al., 2001). In hot water washing, biomass is contacted with water (under pressure) at elevated temperatures of 160° C. to 230° C. This process can effectively hydrolyze greater than 90% of the hemicellulose present and the solubilized hemicellulose is typically over 95% in the form of oligomers (Liu and Wyman, 2003). Following these pretreatments, it is often necessary to effect further depolymerization of the oligomeric hemicelluloses to monomer sugars, which can be accomplished using a variety of catalysts including, liquids, solids, vaporous acids and alkalis, and enzymes.

BRIEF SUMMARY

Embodiments of the invention relate to purified and/or isolated nucleotide sequences of the genome of *Alicyclobacillus acidocaldarius*, or a homologue or fragment thereof. In one embodiment of the invention, the nucleotide sequence is SEQ ID NO:1 or a homologue or fragment thereof. In another embodiment of the invention, the homologue has at least 80% sequence identity to SEQ ID NO:1.

Embodiments of the invention may further relate to an isolated and/or purified nucleic acid sequence comprising a nucleic acid sequence encoding a polypeptide having at least 90% sequence identity to the polypeptide of SEQ ID NO:2.

Embodiments of the invention also relate to isolated and/or purified polypeptides encoded by a nucleotide sequence of the genome of *Alicyclobacillus acidocaldarius*, or a homologue or fragment thereof. In one embodiment, the nucleotide sequence has at least 80% sequence identity to SEQ ID NO:1. In another embodiment of the invention, the nucleotide sequence is SEQ ID NO:1 or a homologue or fragment thereof. In still another embodiment, the polypeptide has the amino acid sequence of SEQ ID NO:2. In yet another embodiment, the polypeptide has at least 80% sequence identity to SEQ ID NO:2.

In embodiments of the invention, the polypeptides may be acidophilic and/or thermophilic. In further embodiments, the polypeptides may be glycosylated, pegylated, or otherwise post-translationally modified.

Embodiments of the invention include methods of at least partially degrading or cleaving xylotriose and/or xylobiose to release xylose. Such methods may comprise placing a polypeptide having at least 90% sequence identity to the polypeptide of SEQ ID NO:2 in fluid contacting xylotriose and/or xylobiose.

Embodiments of the invention include methods of at least partially degrading or cleaving a terminal arabinose from arabinofuranose-substituted xylan. Such methods may comprise placing a polypeptide having at least 90% sequence identity to the polypeptide of SEQ ID NO:2 in fluid contacting arabinofuranose-substituted xylan.

These and other aspects of the invention will become apparent to the skilled artisan in view of the teachings contained herein.

BRIEF DESCRIPTION OF THE DRAWINGS

FIGS. 1A through 1D depict a sequence alignment between SEQ ID NO:2 (RAAC00307), a beta-xylosidase, and gi|76795911, gi|15642851, gi|148269983, gi|15899739, and gi|116621797 (SEQ ID NOs:3-7 respectively) which are all beta-xylosidases. Amino acids common to three or more of the sequences aligned are indicated in bold.

DETAILED DESCRIPTION

Figure 2:
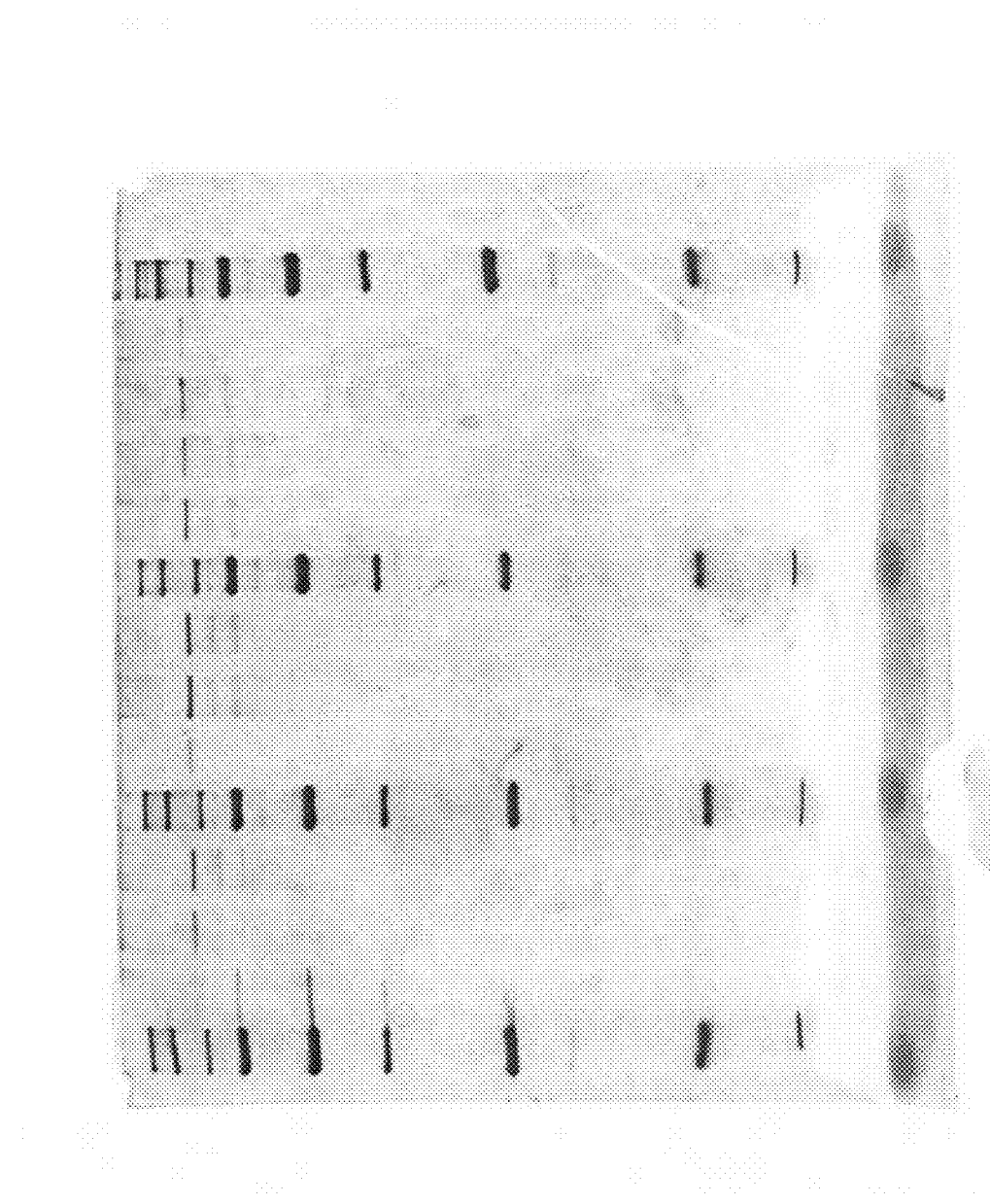
FIG. 2 depicts a silver stained SDS-PAGE gel of crude extracellular extract from *Alicyclobacillus acidocaldarius* grown to stationary phase on a mineral salt medium with 0.5 g/L wheat arabinoxylan as the carbon source.

It is desirable to utilize the sugars contained in the cellulose and hemicellulose of lignocellulosic residues for production of fuels and value-added chemicals in a Biorefinery concept. Lignocellulosic residues including corn stover consist of a heterogeneous three-dimensional matrix comprised primarily of cellulose, hemicellulose and lignin. Because of the heterogeneous nature of lignocellulose, the cellulose and hemicellulose are not directly accessible. Many fuels and chemicals can be made from these lignocellulosic materials. To utilize lignocellulosic biomass for production of fuels and chemicals via fermentative processes, it is necessary to convert the plant polysaccharides to sugar monomers, which are then fermented to products using a variety of microorganisms. Direct hydrolysis of lignocellulose by mineral acids to monomers is possible at high temperatures and pressures; however, with unavoidable yield losses due to thermal decomposition of the sugars. One strategy to reduce these yield losses is to use cellulases and potentially other enzymes to depolymerize the polysaccharides at moderate temperatures.

Acid pretreatments have been developed to hydrolyze and remove hemicellulose and thereby increase the susceptibility of the cellulose in the matrix to cellulolytic attack. However, these acid pretreatments have high capital and operating costs due to high temperatures and pressures, the need for expensive alloys that can withstand the high temperature corrosive environment, and they produce significant amounts of thermal decomposition products of the sugars depending on pretreatment severity. These thermal decomposition products represent a loss of potential sugars that could be utilized for subsequent fermentations and are also toxic to fermenting organisms. Because of these issues, a desired direction for fermentative biorefinery development is to integrate various elements of pretreatment, enzymatic hydrolysis, and fermentation processes. There are various ways to integrate the enzymatic polysaccharide hydrolysis and fermentation processes. For commercially available enzymes to be used for this purpose, the pretreatment slurry must be neutralized by overliming or another method and cooled to 40° C. to 50° C., adding significant cost to the process. In contrast, acid stable thermotolerant hemicellulases can be used together with or following reduced severity acid pretreatments to lower the energy and capital costs. This would allow maximum yields of hemicellulose-derived sugars and minimize the formation of toxic byproducts. This strategy also necessarily results in the accumulation of hemicellulose oligomers in the pretreatment liquor, requiring further hydrolysis of the oligomers to monomers before most microbes can utilize them. Addition of acid stable thermotolerant hydrolytic enzymes such as cellulases, xylanases, and xylosidases to the biomass slurry during the pretreatment allows the use of lower temperatures and pressures, as well as cheaper materials of construction, reducing both the capital and energy, and perhaps greatly reducing or eliminating the need for high pressure steam for the pretreatment.

Embodiments of the invention relate in part to gene sequences and protein sequences encoded by genes of *Alicyclobacillus acidocaldarius*. Genes included are those encoding proteins capable of breaking down xylotriose and xylobiose into xylose (beta-xylosidases) and those capable of breaking down arabinofuranose-substituted xylan (arabinofuranosidases).

The present invention relates to isolated and/or purified nucleotide sequences of the genome of *Alicyclobacillus acidocaldarius* wherein the nucleotide sequence comprises SEQ ID NO:1 or one of its fragments.

The present invention likewise relates to isolated and/or purified nucleotide sequences, characterized in that they are selected from: a) a nucleotide sequence of a specific fragment of the sequence SEQ ID NO:1 or one of its fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of the DNAs.

Embodiments of the present invention relate to sequences that it has been possible to isolate, purify, or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences of the invention to be carried by vectors.

An isolated and/or purified nucleotide sequence fragment according to the invention will be understood as designating any nucleotide fragment of the genome of *Alicyclobacillus acidocaldarius*, and may include, by way of non-limiting examples, a length of at least 8, 12, 20 25, 50, 75, 100, 200, 300, 400, 500, 1000, or more, consecutive nucleotides of the sequence from which it originates.

A specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

A homologous isolated and/or purified nucleotide sequence in the sense of the present invention is understood as meaning having isolated and/or purified a nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

A specific homologous nucleotide sequence in the sense of the present invention is understood as meaning a homologous nucleotide sequence having at least one nucleotide sequence of a specific fragment, such as defined above. The "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as, defined in the present application.

Two amino acids or nucleotidic sequences are said to be "identical" if the sequence of amino acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence," software that is available at the web site located on the world wide web ncbi.nlm.nih.gov/gorf/b12.html, and habitually used by the inventors and in general by a skilled person for comparing and determining the identity between two sequences, gap cost, which depends on the sequence length to be compared is directly selected by the software (i.e., 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antiparallel sequence). In embodiments of the invention a nucleotide sequence of the invention and/or a complementary nucleotide sequence of a sequence of the invention may be used to alter the expression of a gene. Examples of techniques which may be used to alter the expression of a gene include, but are not limited to, RNAi, siRNA, and antisense technologies.

Hybridization under conditions of stringency with a nucleotide sequence according to the invention is understood as meaning a hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following, described herein below.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at a temperature of 65° C.; 2×0.5×SSC, 0.5% SDS; at a temperature of 65° C. for ten minutes each.

The conditions of intermediate stringency, using, for example, a temperature of 42° C. in the presence of a 2×SSC buffer, or of less stringency, for example, a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by a person skilled in the art for oligonucleotides of greater or smaller size, according to the teachings of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to a person skilled in the art.

Among the isolated and/or purified nucleotide sequences according to the invention, those are again preferred that can be used as a primer or probe in methods allowing the presence of a sequence comprising SEQ ID NO:1, one of its fragments, or one of its variants, such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to a person skilled in the art, and containing modifications with respect to the normal sequences according to the invention, for example, mutations in the regulatory and/or promoter sequences of polypeptide expression, especially leading to a modification of the rate of expression of the polypeptide or to a modulation of the replicative cycle.

Modified nucleotide sequence will likewise be understood as meaning any nucleotide sequence coding for a modified polypeptide such as defined below.

The present invention relates to isolated and/or purified nucleotide sequences of *Alicyclobacillus acidocaldarius*, characterized in that they are selected from the sequence SEQ ID NO:1 or one of its fragments.

Embodiments of the invention likewise relate to isolated and/or purified nucleotide sequences characterized in that they comprise a nucleotide sequence selected from: a) a nucleotide sequence SEQ ID NO:1 or one of its fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOs:8-12 or fragments thereof and any other isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID NO:1 or fragments thereof. The homologous sequences can comprise, for example, the sequences corresponding to the genomic sequences of *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide.

Embodiments of the invention comprise the isolated and/or purified polypeptides encoded by a nucleotide sequence according to the invention, or fragments thereof, whose sequence is represented by a fragment. Amino acid sequences corresponding to the isolated and/or purified polypeptides which can be encoded according to one of the three possible reading frames of the sequence SEQ ID NO:1.

Embodiments of the invention likewise relate to the isolated and/or purified polypeptides, characterized in that they comprise a polypeptide selected from the amino acid sequences SEQ ID NO:2 or one of its fragments.

Further embodiments of the invention relate to the isolated and/or purified polypeptides, characterized in that they comprise a polypeptide selected from the amino acid sequences SEQ ID NO:2 or one of its fragments, wherein the polypeptides have beta-xylosidase and/or arabinofuranosidase activity.

Among the isolated and/or purified polypeptides, according to embodiments of the invention, are the isolated and/or purified polypeptides comprising any one or more of amino acid sequence SEQ ID NOs:13-17, or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID NO:2 or fragments thereof.

Embodiments of the invention also relate to the polypeptides, characterized in that they comprise a polypeptide selected from: a) a specific fragment of at least five amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide, and protein are interchangeable.

In embodiments of the invention, the isolated and/or purified polypeptides according to the invention may be glycosylated, pegylated, or otherwise post-translationally modified. In further embodiments, glycosylation may occur in vivo or in vitro and may be performed enzymatically or using chemical glycosylation techniques. In additional embodiments, any glycosylation, pegylation and/or other post-translational modifications may be N-linked or O-linked.

In embodiments of the invention any one of the isolated and/or purified polypeptides according to the invention may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5.5, 5, 4, 3, 2, 1, and/or 0. In further embodiments of the invention, glycosylation, pegylation, or other post-translational modification may be required for the isolated and/or purified polypeptides according to the invention to be soluble and/or enzymatically active at a pH at or below 7, 6, 5.5, 5, 4, 3, 2, 1, and/or 0 or at a temperature at or above about 25, 30, 35, 40, 45, 50, 55, 60, 65, 70, 75, 80, 85, 90, and/or 95 degrees Celsius. In further embodiments, the enzymatic activity may be beta-xylosidase and/or arabinofuranosidase activity.

Embodiments of the invention relate to polypeptides which are isolated or obtained by purification from natural sources, or else obtained by genetic recombination, or alternatively by chemical synthesis and that they may thus contain amino acids that do not normally occur in living systems, as will be described below.

A "polypeptide fragment" according to the embodiments of the invention is understood as designating a polypeptide containing at least five consecutive amino acids, preferably ten consecutive amino acids or fifteen consecutive amino acids. Non-limiting examples of polypeptide fragments according to the invention include polypeptides containing 5, 10, 15, 25, 50, 75, 100, 200, 300, 400, 500, 1000, or more, consecutive residues. In further embodiments, the polypeptide fragment may comprise beta-xylosidase and/or arabinofuranosidase activity.

In the present invention, a specific polypeptide fragment is understood as designating the consecutive polypeptide fragment encoded by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 90%, homology with the sequences of amino acids of polypeptides according to the invention. In further embodiments, a homologous polypeptide may comprise beta-xylosidase and/or arabinofuranosidase activity.

"Specific homologous polypeptide" will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. Examples of such substitutions in the amino acid sequence SEQ ID NO:2 may include those isolated and/or purified polypeptides of amino acid sequence SEQ ID NOs:13-17.

These equivalent amino acids can be determined either by depending on their structural homology with the amino acids which they substitute, or on results of comparative tests of biological activity between the different polypeptides, which are capable of being carried out.

By way of non-limiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins which have similar identified enzymatic activity. For example, FIG. 1 herein provides a sequence alignment between a certain polypeptide of the invention (SEQ ID NO:2) and other polypeptides identified as having similar enzymatic activity, with amino acids common to three or more of the sequences aligned as indicated in bold. Thus, according to one embodiment of the invention, substitutions or mutations may be made at positions that are not indicated as in bold in the figures. Examples of such polypeptides may include, but are not limited to, those found in amino acid sequence SEQ ID NOs:13-17. In a further embodiment, nucleic acid sequences may be mutated or substituted such that the amino acid they encode is unchanged (degenerate substitutions and/mutations) and/or mutated or substituted such that any resulting amino acid substitutions or mutations are made at positions that are not indicated as in bold in the figures. Examples of such nucleic acid sequences may include, but are not limited to, those found in the nucleotide sequences of SEQ ID NOs:8-12 or fragments thereof.

The specific homologous polypeptides likewise correspond to polypeptides encoded by the specific homologous nucleotide sequences such as defined above and thus comprise in the present definition the polypeptides, which are mutated or correspond to variants that can exist in *Alicyclobacillus acidocaldarius*, and which especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of acting as beta-xylosidase and/or as an arabinofuranosidase.

The polypeptide fragments according to embodiments of the invention can correspond to isolated or purified fragments naturally present in a *Alicyclobacillus acidocaldarius* or correspond to fragments which can be obtained by cleavage of the polypeptide by a proteolytic enzyme, such as trypsin, chymotrypsin, or collagenase, or by a chemical reagent, such as cyanogen bromide (CNBr). Such polypeptide fragments can likewise easily be prepared by chemical synthesis and/or from hosts transformed by an expression vector according to the invention containing a nucleic acid allowing the expression of the polypeptide fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of a specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Examples of modified polypeptides include, but are not limited to, those in which up to 5, 10, 15, 20, 25, 30, 35, 40, 45, 50, 55, 60, 65, 70, 75, 80, 85, 90, 95, 100, 125, 150, 175, 200, 250, 300, 350, 400, 450, or 500 amino acids can be modified, truncated at the N- or C-terminal end, or even deleted or added.

The methods allowing the modulations on eukaryotic or prokaryotic cells to be demonstrated are well known to a person of ordinary skill in the art. It is likewise well understood that it will be possible to use the nucleotide sequences coding for the modified polypeptides for the modulations, for example through vectors according to the invention and described below.

The preceding modified polypeptides can be obtained by using combinatorial chemistry, in which it is possible to systematically vary parts of the polypeptide before testing them on models, cell cultures or microorganisms, for example, to select the compounds that are most active or have the properties sought.

Chemical synthesis likewise has the advantage of being able to use unnatural amino acids, or nonpeptide bonds.

Thus, in order to improve the duration of life of the polypeptides according to the invention, it may be of interest to use unnatural amino acids, for example in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by proteases.

The nucleotide sequences coding for a polypeptide according to the invention are likewise part of the invention.

The invention likewise relates to nucleotide sequences utilizable as a primer or probe, characterized in that the sequences are selected from the nucleotide sequences according to the invention.

It is well understood that the present invention, in various embodiments, likewise relates to specific polypeptides of *Alicyclobacillus acidocaldarius*, encoded by nucleotide sequences, capable of being obtained by purification from natural polypeptides, by genetic recombination or by chemical synthesis by procedures well known to a person skilled in the art and such as described in particular below. In the same manner, the labeled or unlabeled mono- or polyclonal antibodies directed against the specific polypeptides encoded by the nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least eight nucleotides, preferably of at least twelve nucleotides, and even more preferentially at least twenty nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievits et al. in 1991; the SDA technique (Strand Displacement Amplification) (Walker et al., 1992); and the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive element ($^{32}$P, $^{35}$S, $^{3}$H, $^{125}$I) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 7810975 or by Urdea et al. or by Sanchez-Pescador et al., both in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between a capture probe and the target nucleic acid is then detected with the aid of a second probe, a so-called "detection probe," labeled with an easily detectable element.

Another aspect of the present invention is a vector for the cloning and/or expression of a sequence, characterized in that it contains a nucleotide sequence according to the invention.

The vectors according to the invention, characterized in that they contain the elements allowing the expression and/or the secretion of the nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by a person skilled in the art, and it will be possible to introduce the clones resulting therefrom into an appropriate host by standard methods, such as, for example, transfection, lipofection, electroporation, and thermal shock.

As used herein "transformed" and "transforming" refer to a cell comprising, or the process of providing to a cell, a vector. Transformed cells may or may not be immortalized. Immortalization of a transformed cell may or may not be due to the presence of particular nucleic acid sequences in a vector. In embodiments of the invention, a vector or a portion of a vector may be stably integrated into the genome of a cell. In embodiments, integration of a vector or a portion of a vector does not alter the status of the cell as having been "transformed" according to the present invention.

The vectors according to the invention are, for example, vectors of plasmid or viral origin. One example of a vector for the expression of polypeptides of the invention is baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), plant cells (such as, but not limited to, *Arabidopsis* sp.), as well as animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the invention likewise relate to organisms comprising one of the transformed cells according to the invention.

The obtainment of transgenic organisms according to the invention over-expressing one or more of the genes of *Alicyclobacillus acidocaldarius* or part of the genes may be carried out in, for example, rats, mice, or rabbits according to methods well known to a person skilled in the art, such as by viral or nonviral transfections. It will be possible to obtain the transgenic organisms over-expressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells as well as the transgenic organisms according to the invention are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of the transformed cells according to the invention, are themselves comprised in the present invention.

Among the procedures for preparation of a polypeptide of the invention in recombinant form, the preparation procedures employing a vector, and/or a cell transformed by the vector and/or a transgenic organism, comprising one of the transformed cells, containing a nucleotide sequence according to the invention coding for a polypeptide of the invention.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of nucleotide sequences according to the invention; b) if need be, recovery of the recombinant polypeptide.

When the procedure for preparation of a polypeptide of the invention employs a transgenic organism according to the invention, the recombinant polypeptide is then extracted from the organism.

The invention also relates to a polypeptide which is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive function carried by these amino acids or fragments, with the exception of amine functions of one and carboxyls of the other or vice versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

The hybrid nucleotide sequences coding for a hybrid polypeptide as well as the hybrid polypeptides according to the invention characterized in that they are recombinant polypeptides obtained by the expression of the hybrid nucleotide sequences are likewise part of the invention.

The invention likewise comprises the vectors characterized in that they contain one of the hybrid nucleotide sequences. The host cells transformed by the vectors, the transgenic organisms comprising one of the transformed cells as well as the procedures for preparation of recombinant polypeptides using the vectors, the transformed cells and/or the transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius* or proteins therefrom, in a sample capable of containing them. These procedures, according to the specificity of the polypeptides, the antibodies and the nucleotide sequences according to the invention which will be used, will in particular be able to detect and/or to identify a *Alicyclobacillus acidocaldarius* or proteins therefrom.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between the polypeptide and the antibodies possibly present in the biological sample); b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA (Enzyme-linked immunosorbent assay) technique, by immunofluorescence, or radioimmunological processes (RIA) or their equivalent.

Thus, the invention likewise relates to the polypeptides according to the invention, labeled with the aid of an adequate label such as of the enzymatic, fluorescent or radioactive type.

Such methods comprise, for example, the following steps: deposition of determined quantities of a polypeptide composition according to the invention in the wells of a microtiter plate, introduction into the wells of increasing dilutions of serum, or of a biological sample other than that defined previously, having to be analyzed, incubation of the wells of a microtiter plate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm, detection, by comparison with a control test, of the quantity of hydrolyzed substrate.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Köhler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide which has served as an antigen has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* or proteins therefrom in a sample, characterized in that it comprises the following steps: a) contacting of the sample with a mono- or polyclonal antibody according to the invention (under conditions allowing an immunological reaction between the antibodies and the polypeptides of *Alicyclobacillus acidocaldarius* possibly present in the biological sample); b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* or proteins therefrom in a sample, characterized in that it contains the following steps: a) if need be, isolation of the DNA from the sample to be analyzed; b) specific amplification of the DNA of the sample with the aid of at least one primer, or a pair of primers, according to the invention; c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in the biological sample.

A further embodiment of the invention comprises a method, characterized in that it comprises the following steps: a) contacting of a nucleotide probe according to the invention with a biological sample, the DNA contained in the biological sample having, if need be, previously been made accessible to hybridization under conditions allowing the hybridization of the nucleotide probe with the DNA of the sample; b) demonstration of the hybrid formed between the nucleotide probe and the DNA of the biological sample.

The present invention also relates to a procedure according to the invention, characterized in that it comprises the following steps: a) contacting of a nucleotide probe immobilized on a support according to the invention with a biological sample, the DNA of the sample having, if need be, previously been made accessible to hybridization, under conditions allowing the hybridization of the nucleotide probe with the DNA of the sample; b) contacting of the hybrid formed between the nucleotide probe immobilized on a support and the DNA contained in the biological sample, if need be after elimination of the DNA of the biological sample that has not hybridized with the nucleotide probe, with a nucleotide probe labeled according to the invention; c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

Further embodiments of the invention comprise methods of at least partially degrading xylotriose into xylobiose and xylose and/or the cleavage of xylobiose into two units of xylose. Degrading these structures have art recognized utility such as those described in Mielenz 2001; Jeffries 1996; Shallom and Shoham 2003; Lynd et al. 2002; Vieille and Zeikus 2001; Bertoldo et al. 2004; and/or Malherbe and Cloete 2002. Embodiments of the invention comprise methods of degrading arabinofuranose-substituted xylans.

Embodiments of methods include placing a recombinant, purified, and/or isolated polypeptide having at least 90% sequence identity to the polypeptide of SEQ ID NO:2 in fluid contact with arabinofuranose-substituted xylan, xylotriose and/or xylobiose or in an environment where arabinofuranose-substituted xylan, xylotriose and/or xylobiose is to be produced.

Further embodiments of methods include placing a cell producing or encoding a recombinant, purified, and/or isolated polypeptide having at least 90% sequence identity to the polypeptide of SEQ ID NO:2 in fluid contact with arabinofuranose-substituted xylan, xylotriose and/or xylobiose or in an environment where arabinofuranose-substituted xylan, xylotriose and/or xylobiose is to be produced.

As used herein, "partially degrading" relates to the rearrangement or cleavage of chemical bonds in the target structure. In additional embodiments, "partially degrading" includes the cleavage of xylotriose into xylobiose and xylose and/or the cleavage of xylobiose into two units of xylose.

In additional embodiments, methods of at least partially degrading arabinofuranose-substituted xylan, xylotriose and/or xylobiose may take place at temperatures at or above about 25, 30, 35, 40, 45, 50, 55, 60, 65, 70, 75, 80, 85, 90, and/or 95 degrees Celsius and/or at a pH at, below, and/or above 7, 6, 5.5, 5, 4, 3, 2, 1, and/or 0.

Further embodiments of the invention may comprise a kit for at least partially degrading arabinofuranose-substituted xylan, xylotriose and/or xylobiose, the kit comprising a cell producing or encoding a recombinant, purified, and/or isolated polypeptide having at least 90% sequence identity the polypeptide of SEQ ID NO:2 and/or a recombinant, purified, and/or isolated polypeptide having at least 90% sequence identity to the polypeptide of SEQ ID NO:2.

In embodiments of the invention the any one of the isolated and/or purified polypeptides according to the invention may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5.5, 5, 4, 3, 2, 1, and/or 0. In further embodiments of the invention, glycosylation, pegylation, or other post-translational modification may be required for the isolated and/or purified polypeptides according to the invention to be soluble and/or enzymatically active at a pH at or below 7, 6, 5.5, 5, 4, 3, 2, 1, and/or 0 or at a temperature at or above about 25, 30, 35, 40, 45, 50, 55, 60, 65, 70, 75, 80, 85, 90, and/or 95 degrees Celsius.

The invention is described in additional detail in the following illustrative examples. Although the examples may represent only selected embodiments of the invention, it should be understood that the following examples are illustrative and not limiting.

EXAMPLES

Example 1

Isolation of Xylanase and Beta-Xylosidase from *Alicyclobacillus acidocaldarius*

Figure 3:
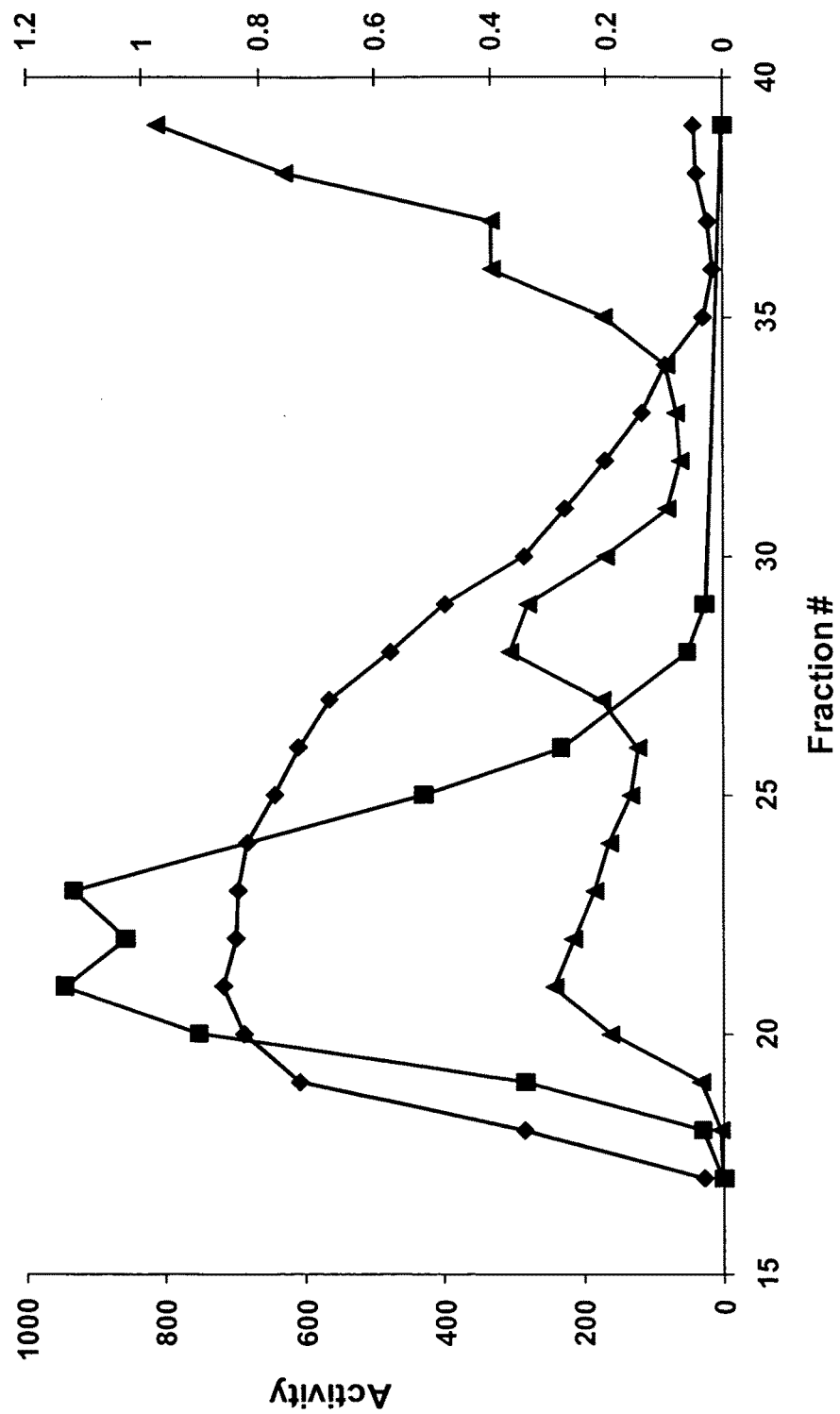
FIG. 3 is a graph depicting an elution of proteins from a cation exchange chromatography column used to concentrate and nominally purify the proteins. The proteins were produced in the extracellular fluid of *Alicyclobacillus acidocaldarius* grown on wheat arabionoxylan at a temperature of 60° C. and at a pH of 3.5. Total protein is depicted as triangles (right-hand y-axis); endoxylanase activity is depicted by squares (left-hand y-axis); and endoglucanase activity is depicted by diamonds (left-hand y-axis).

*Alicyclobacillus acidocaldarius* produces extracellular xylanase(s) when grown on a medium that contains xylan as its sole carbon source. This organism has an optimum temperature range of 55° C. to 60° C. and an optimum pH of 3.5 for growth. Thirty liters of *Alicyclobacillus acidocaldarius* were grown on a minimal salt medium at a pH of 3.5 and at a temperature of 60° C. containing 0.5 g/L wheat arabinoxylan as the sole carbon source. The culture was grown to stationary phase and harvested by centrifugation to remove cells. The resulting supernatant was filtered through a 0.22 µm filter to remove any remaining cells. This supernatant was then loaded onto a cation exchange column (Poros HS, Applied Biosystems) at a flow rate of 7.75 mL/minute at room temperature. Bound proteins were then eluted off with a sodium chloride salt gradient from 0 to 1 M over five minutes and collected as a single fraction. This fraction was desalted, concentrated and reloaded onto the cation exchange column. A wash was performed to remove unbound material. Bound proteins were eluted with another sodium chloride salt gradient from 0 to 1 M over five minutes at a flow rate of 10 ml/minute and fractions were collected every six seconds. The levels of protein (triangles), endoxylanase (squares), and endoglucanase (diamonds) activities in fractions 17 through 39 are shown in FIG. 3. One of the resulting peaks appears to be two overlapping peaks. Overlaying the xylanase (squares) and cellulase (diamonds) activities of each fraction shows that the two activities overlap, which demonstrates the presence of two or more enzymes (FIG. 3). Fractions 15 through 34 were pooled (hereafter referred to as pooled concentrate chromatography fractions, PCCF)) and subjected to SDS-PAGE electrophoresis. The SDS-PAGE gel of PCCF contains five major protein bands and several minor bands as well (FIG. 2). The multiple bands in the SDS-PAGE gel of PCCF in FIG. 2 support the presence of multiple enzymes.

Example 2

Demonstration of Endoxylanase and Beta-Xylosidase Activities from *Alicyclobacillus acidocaldarius*

The endoxylanase and beta-xylosidase activities of the PCCF were tested at a temperature of 60° C. and at a pH of 2.0 with 3.95 g/L insoluble oat spelt xylan as the substrate. The results were compared to those from a parallel test of the endoxylanase activity of the endo-β -1,4-xylanase from *Thermomyces lanuginosus* (available from the Sigma-Aldrich Co., St. Louis, Mo., product number X2753), using insoluble oat spelt xylan at 4.19 g/L as the substrate and operated at a temperature of 50° C. and at a pH of 4.7. The appearance of carbohydrate oligosaccharides and monomers in the aqueous phase was monitored for 72 hours by HPLC. The products arising from enzymatic activity were identified by comparison with HPLC data from enzyme-free controls operated under the same conditions.

Figure 4:
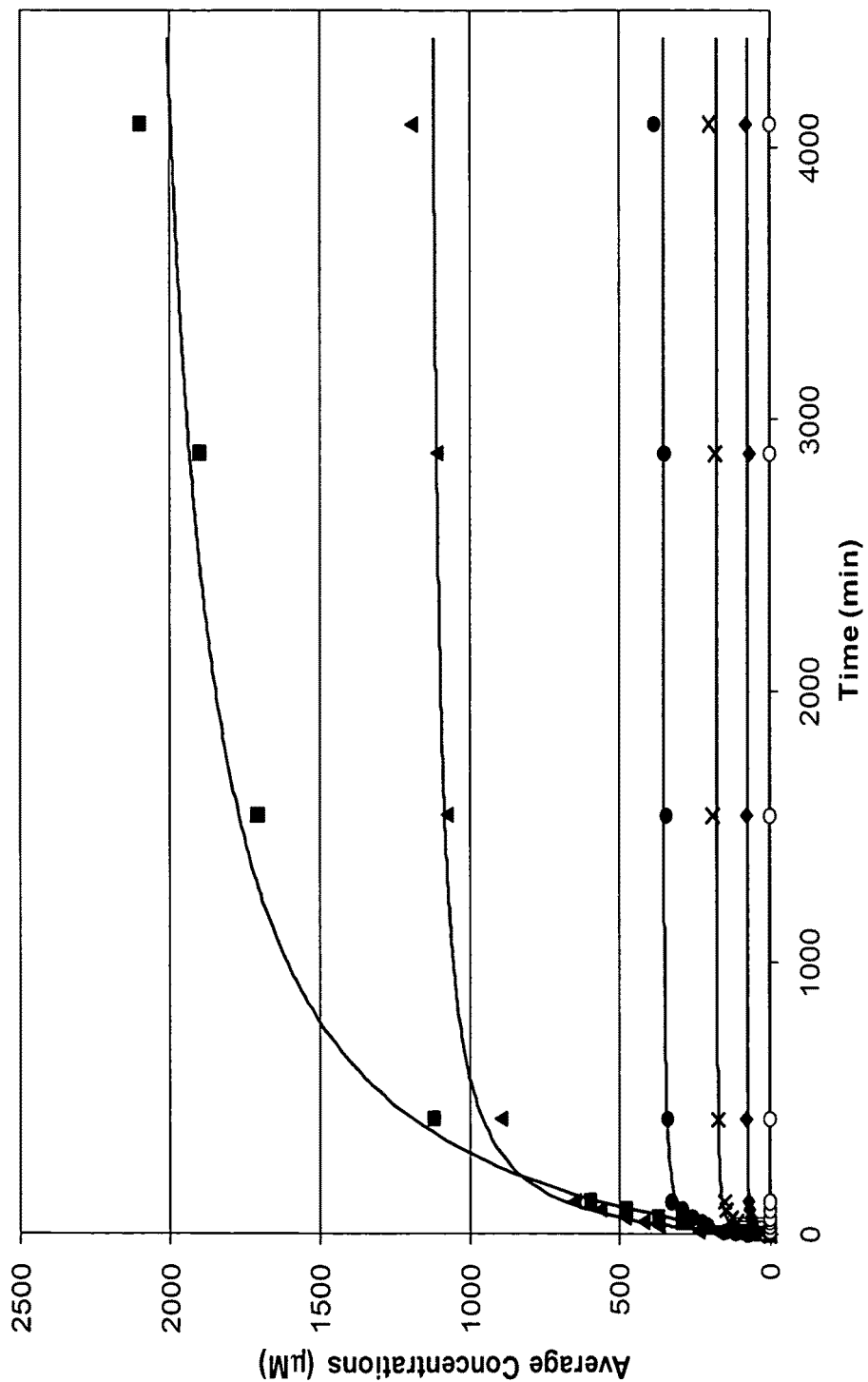
FIG. 4 is a graph depicting the xylanase activity at a temperature of 50° C. and at a pH of 4.7 of a commercial endoxylanase from *Thermomyces lanuginosus* challenged with 4.19 g/L insoluble oat spelt xylan and monitored via HPLC (high performance liquid chromatography). Levels of xylohexaose are depicted as diamonds; levels of xylopentaose are depicted as Xs; levels of xylotetraose are depicted as closed circles; levels of xylotriose are depicted as triangles; levels of xylobiose are depicted as squares; and levels of xylose are depicted as open circles. The curved lines represent a nonlinear regression of the data points presented.

As expected, the *Thermomyces lanuginosus* enzyme exhibited endoxylanase activity, which acts by cleaving the β-1-1,4-xylan backbone internally, and oligomers of 13-1,4-xylan were produced. These oligomers included xylohexaose, xylopentaose, xylotetraose, xylotriose, and xylobiose (FIG. 4). The primary end products were xylobiose and xylotriose, by definition the end products of an endo-β-1,4-xylanase. Therein, it can be seen that the levels of xylose (open circles) remain at zero while the levels of xylobiose (squares) and xylotriose (triangles) show the greatest increase during the experimental period. Levels of xylohexaose (diamonds), xylopentaose (Xs), and xylotetraose (closed circles) are also detectable with the prevalence being inversely correlated to the length of the xylan polymer.

Figure 5:
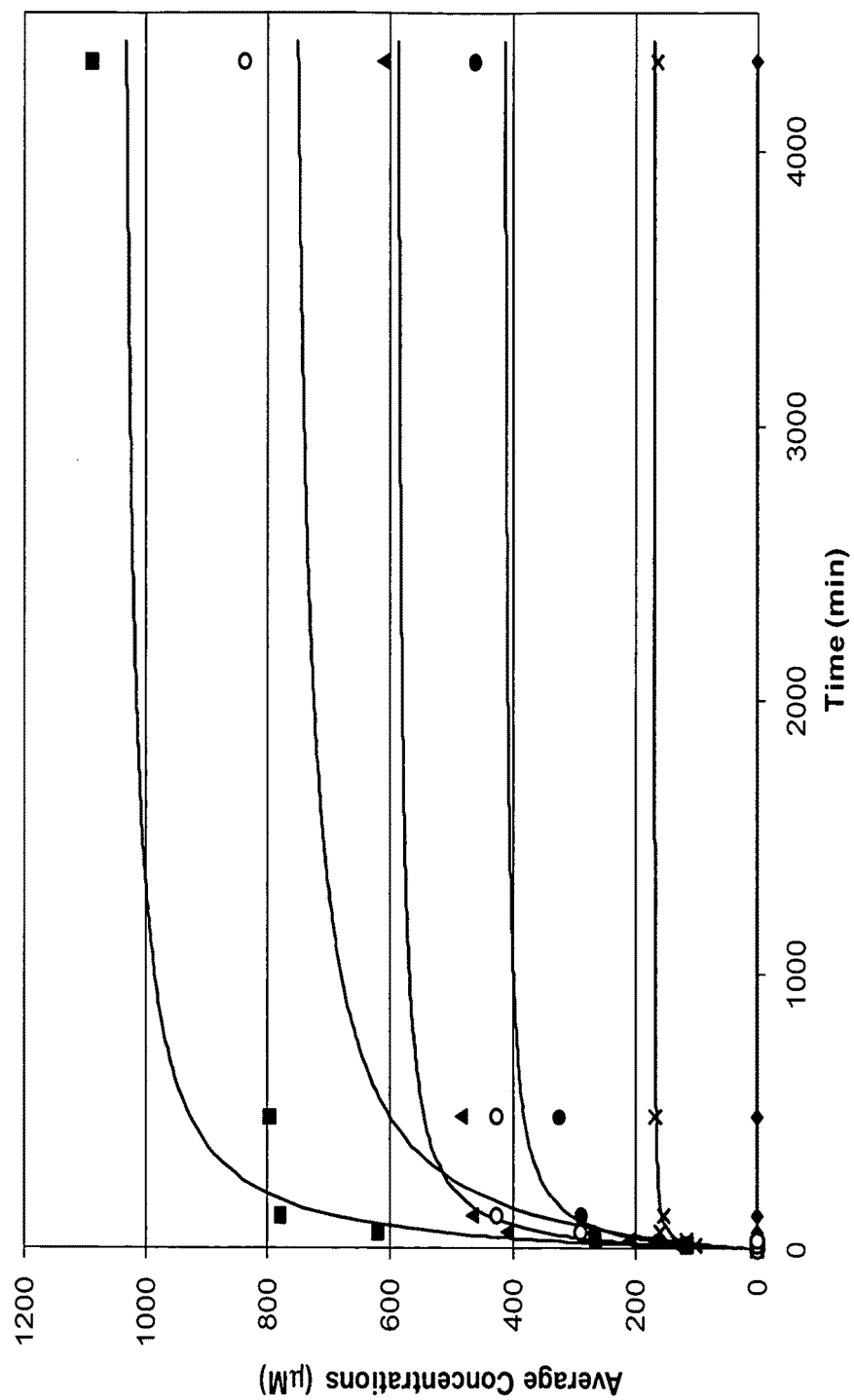
FIG. 5 is a graph depicting the combined activities of endoxylanase and beta-xylosidase at a temperature of 60° C. and at a pH of 2.0 in crude extracellular concentrations from *Alicyclobacillus acidocaldarius* challenged with 3.95 g/L insoluble oat spelt xylan and monitored via HPLC. Levels of xylohexaose are depicted as diamonds; levels of xylopentaose are depicted as Xs; levels of xylotetraose are depicted as closed circles; levels of xylotriose are depicted as triangles; levels of xylobiose are depicted as squares; and levels of xylose are depicted as open circles. The curved lines represent a nonlinear regression of the data points presented.

With regard to the activity of the PCCF, both endoxylanase and beta-xylosidase activities are demonstrably present (FIG. 5). Therein, it can be seen that the levels of xylobiose (squares) and xylotriose (triangles) show the substantial increase during the experimental period. This correlates with the xylanse activity seen for the xylanase from *Thermomyces lanuginosus* as shown in FIG. 4. Levels of xylohexaose (diamonds) remain at zero, while xylopentaose (Xs), and xylotetraose (closed circles) are also detectable. However, in addition to the clear presence of endoxylanase activity seen with the *Thermomyces lanuginosus* enzyme, the PCCF experiments reveal significant xylose production (open circles). As no known endoxylanase to date is able to produce xylose, this indicates the presence of another enzymatic activity, namely beta-xylosidase activity, which is able to convert xylotriose into xylobiose and xylose, as well as convert xylobiose into two units of xylose.

Example 3

Demonstration of Beta-Xylosidase Activity in Concentrate Chromatography Fractions from *Alicyclobacillus acidocaldarius*

Figure 6:
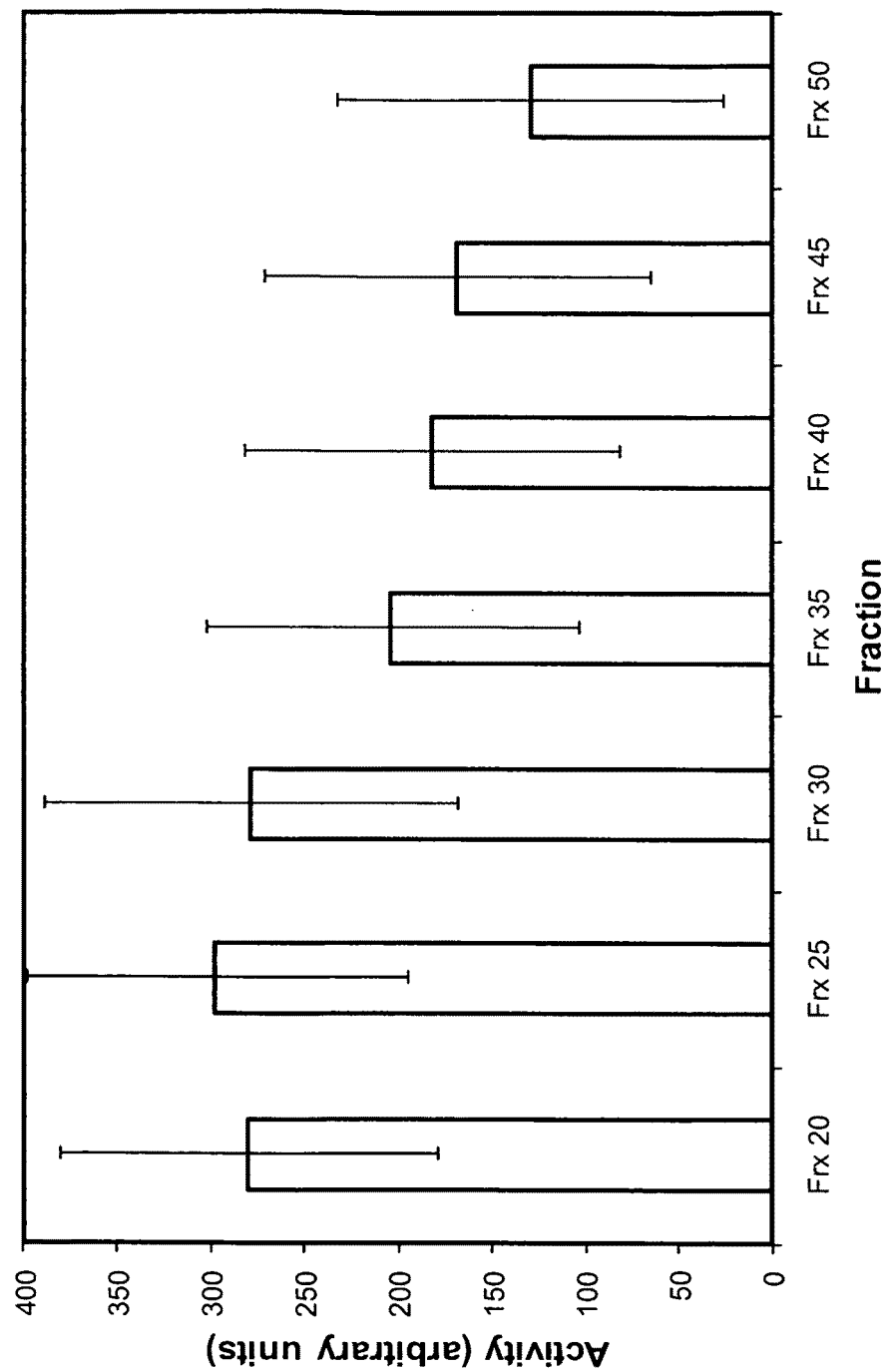
FIG. 6 is a graph depicting β-xylosidase activity distributed throughout fractions 20 through 50 with the highest activity occurring around fraction 25 and then tapering off from fraction 30 through fraction 50. Activity assays were conducted in duplicate and the error bars indicate the standard deviation.

Thirty liters of *Alicyclobacillus acidocaldarius* were grown on a minimal salt medium at a pH of 3.5 and at a temperature of 60° C. containing 0.5 g/L wheat arabinoxylan as the sole carbon source. The culture was grown to stationary phase and harvested by centrifugation to remove cells. The resulting supernatant was filtered through a 0.22 µM filter to remove any remaining cells, and loaded onto a cation exchange column (Poros HS, Applied Biosystems) at a flow rate of 7.75 mL/minute at room temperature. One liter of the supernatant (pre-column) was reserved for testing of β-xylosidase activity prior to purification. One liter of the flow through (post-column) was reserved to test β-xylosidase activity that did not bind to the column. Bound proteins were then eluted off with a sodium chloride salt gradient from 0 to 1 M over five minutes and collected as a single fraction. This fraction was desalted, concentrated and reloaded onto the cation exchange column. A wash was performed to remove unbound material. Bound proteins were eluted with another sodium chloride salt gradient from 0 to 1 M over five minutes at a flow rate of 10 ml/minute and fractions were collected every six seconds. The pre- and post-column liquids were concentrated 125-fold and tested for β-xylosidase. The individual fractions were also tested for activity. The β-xylosidase activity was tested in the concentrated chromatography fractions ranging from fraction 20 through fraction 50 using an analog substrate, p-methylumbelliferyl-β-D-xylopyranoside, at a pH of 3.5 and at a temperature of 60° C. This compound has a bond similar to the xylose-xylose bond found in xylobiose and xylotriose and when cleaved yields a fluorescent product. Enzyme-free controls were also conducted to account for abiotic hydrolysis of the substrate. Beta-xylosidase activity was found in both the pre- and post-column fractions as well as distributed throughout the eluted fractions although there does appear to be a broad peak around fraction 25 (FIG. 6). This may indicate that the column did not have enough binding capacity for the activity or that it did not bind very strongly.

Given the demonstrated beta-xylosidase activity of the PCCF and of multiple separate concentrate chromatography fractions, the entire genome of *Alicyclobacillus acidocaldarius* was sequenced using techniques standard in the art. Open reading frames were analyzed for encoding a beta-xylosidase. One gene encoding a protein having high homology to other beta-xylosidases was identified, namely RAAC00307 (SEQ ID NO:1).

Example 4

RAAC00307: a Beta-Xylosidase

Provided in SEQ ID NO:1 is a nucleotide sequence isolated from Alicyclobacillus acidocaldarius and encoding the polypeptide of SEQ ID NO:2. As can be seen in FIGS. 1A through 1D, SEQ ID NO:2 aligns well with other proteins identified as beta-xylosidases. Of particular importance, it is noted that where amino acids are conserved in other beta-xylosidases, those amino acids are generally conserved in SEQ ID NO:2. Thus, the polypeptide provided in SEQ ID NO:2 is properly classified as a beta-xylosidase.

The polypeptides of SEQ ID NOs:13-17 are representative examples of conservative substitutions in the polypeptide of SEQ ID NO:2 and are encoded by nucleotide sequences of SEQ ID NOs:8-12, respectively.

The nucleotide sequences of SEQ ID NOs:1 and 8-12 are placed into expression vectors using techniques standard in the art. The vectors are then provided to cells such as bacteria cells or eukaryotic cells such as Sf9 cells or CHO (Chinese Hamster Ovary)cells. In conjunction with the normal machinery present in the cells, the vectors comprising SEQ ID NOs:1 and 8-12 produce the polypeptides of SEQ ID NOS:2 and 13-17. The polypeptides of SEQ ID NOs:2 and 13-17 are then isolated and/or purified. The isolated and/or purified polypeptides of SEQ ID NOs:2 and 13-17 are then demonstrated to have activity as beta-xylosidases.

The isolated and/or purified polypeptides of SEQ ID NOs:2 and 13-17 are challenged with xylotriose and/or xylobiose. The isolated and/or purified polypeptides of SEQ ID NOs:2 and 13-17 are demonstrated to have activity in at least partially degrading xylotriose into xylobiose and xylose and/or the cleavage of xylobiose into two units of xylose. Such activity can be unambiguously demonstrated by monitoring the levels of xylotriose, xylobiose, and xylose in the reaction.

Example 5

Production and Purification of RAAC00307: a Beta-Xylosidase

The nucleotide sequence of SEQ ID NO:1 was cloned from *Alicyclobacillus acidocaldarius*. SEQ ID NO:1 encodes the polypeptide of SEQ ID NO:2. SEQ ID NO:1 was cloned into the pBAD/His A expression vector for *E. coli* and the pPIC6α A expression vector for *P. pastoris* and provided to *E. coli* and *P. pastoris* via electroporation and heat shock into competent cells, respectively. Expression of SEQ ID NO:2 was detected from both transformed *E. coli* and *P. pastoris* comprising SEQ ID NO:1 and RAAC00307 was affinity purified using a cobalt resin from these sources for activity testing.

Example 6

Beta-Xylosidase Activity of RAAC00307: a Beta-Xylosidase

RAAC00307 purified from both *E. coli* and *P. pastoris* was tested for beta-xylosidase activity using a fluorescent assay and summarized as follows:

A solution of MUXy1 (4-methylumbelliferyl β-D-xylopyranoside) (Sigma, M7008-1G CAS# 6734-33-4) was created by diluting 10 mg (0.01 g) MUXy1 in 1 mL dimethyl sulfoxide (DMSO). Individual aliquots of the DMSO solution were then diluted 1:100 with 50 mM sodium acetate buffer of pH 2.0, 3.5 and 5.5.

Samples of purified RAAC00307 generated in Example 5 were diluted 1:10; 1:20 and 1:50 in 50 mM sodium acetate buffer of pH 2.0, 3.5 and 5.5. Beta-xylosidase from *A niger* (Sigma, X3501-5UN-CAS# 9025-530) was diluted 1:100 in 50 mM sodium acetate buffer of pH 2.0, 3.5 and 5.5 as positive controls. Samples (RAAC00307 samples and positive controls) were placed in the wells of a 96-well plate in 50 μL aliquots. Blanks of buffer only were placed in some wells. The plate was then preheated to temperatures of 60° C. to 80° C. for five minutes. Ten μL of MUXy1 solution was then added to each cell and the plate was further incubated at a temperature of 60° C. or 80° C. for an additional ten minutes. One hundred μL of 0.5 M sodium carbonate was then added to each well and the β-xylosidase activity was measured in a 96-well plate reader (SPECTRAMAX® Gemini) 355 nm excitation and 460 nm emission.

Specific activity for RAAC00307 as determined appears in Table 1.

TABLE 1

| ASSAY | SPECIFIC ACTIVITY P. pastoris | SPECIFIC ACTIVITY E. coli |
|---|---|---|
| pH 3.5, 60° C. | 1.63 nmol/minute mg | 988 nmol/minute mg |
| pH 5.5, 60° C. | 1.46 nmol/minute mg | 2205 nmol/minute mg |

TABLE 1-continued

| ASSAY | SPECIFIC ACTIVITY P. pastoris | SPECIFIC ACTIVITY E. coli |
|---|---|---|
| pH 3.5, 80° C. | 0.983 nmol/minute mg | 710 nmol/minute mg |
| pH 2.0, 60° C. | 0.566 nmol/minute mg | undetectable |
| pH 2.0, 80° C. | undetectable | undetectable |

Example 7

Beta-Xylosidase Activity of RAAC00307 at Various pH and Temperature

RAAC00307 purified from both E. coli and P. pastoris was tested for beta-xylosidase activity using a fluorescent assay and summarized as follows:

A solution of β-D-xylopyranoside p-nitrophenol (Sigma Cat. No. N2132) was created by diluting 271.2 mg of β-D-xylopyranoside p-nitrophenol in 10 mL methanol. Individual aliquots of this solution were then diluted 1:50 with a 50 mM buffer appropriate for one of pH 1, 2, 3, 4, 5, 6, 7, 8, or 9. Glycine HCl buffer was used for pH 1, 2 and 3; sodium acetate buffer was used for pH 4 and 5; phosphate buffer was used for pH 6 and 7; and Tris buffer was used for pH 8 and 9.

Samples of purified RAAC00307 generated in Example 5 were diluted 1:5, 1:10, 1:20, 1:50 and 1:100 in a 50 mM buffer appropriate for one of pH 1, 2, 3, 4, 5, 6, 7, 8, or 9. Glycine HCl buffer was used for pH 1, 2 and 3; sodium acetate buffer was used for pH 4 and 5; phosphate buffer was used for pH 6 and 7; and Tris buffer was used for pH 8 and 9. Samples (RAAC00307 samples and positive controls) were placed the wells of a 96-well plate in 10 μL aliquots. Blanks of buffer only were placed in some wells. One hundred ninety μL of β-D-xylopyranoside p-nitrophenol solution, preheated to 50, 60, 70, 80, or 90 degrees Celsius, was then added to each cell and the plate further incubated at to 50, 60, 70, 80, or 90 degrees Celsius for an additional 10 minutes. One hundred μL of 2.0 M sodium carbonate was then added to each well and the β-xylosidase activity measured in a 96-well plate reader (Molecular Devices UV-Vis) at a wavelength of 405 nm.

Figure 7:
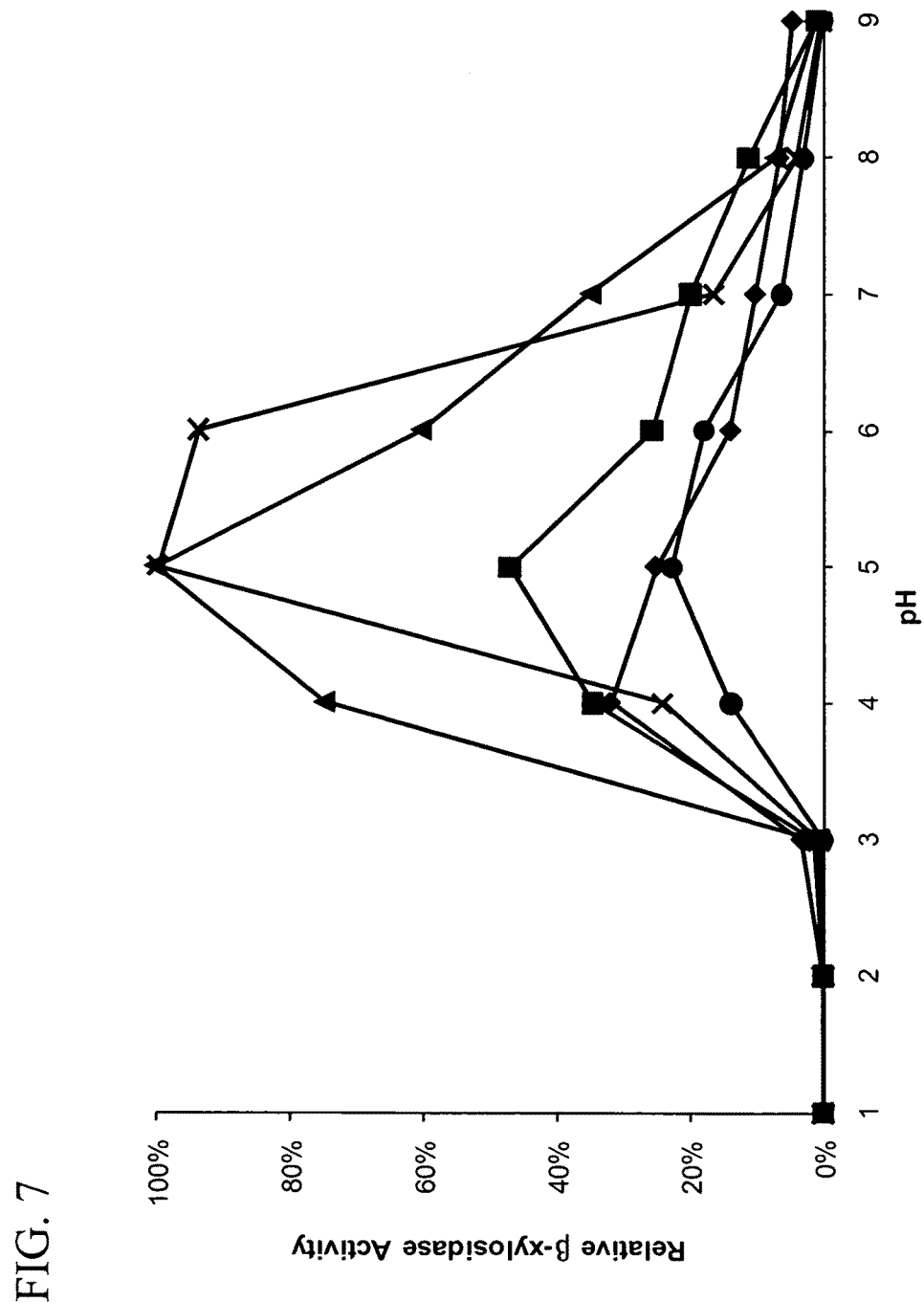
FIG. 7 is a graph depicting the β-xylosidase activity of purified SEQ ID NO:1 (RAAC00307), produced in *E. coli*, at various combinations of temperature and pH. Data are presented relative to the maximum (highest) measured activity. Diamonds indicate a temperature of 50° C.; squares, 60° C.; triangles, 70° C.; Xs, 80° C.; and circles, 90° C. Activity assays were conducted for a minimum of six replicates for each data point shown.
Figure 9:
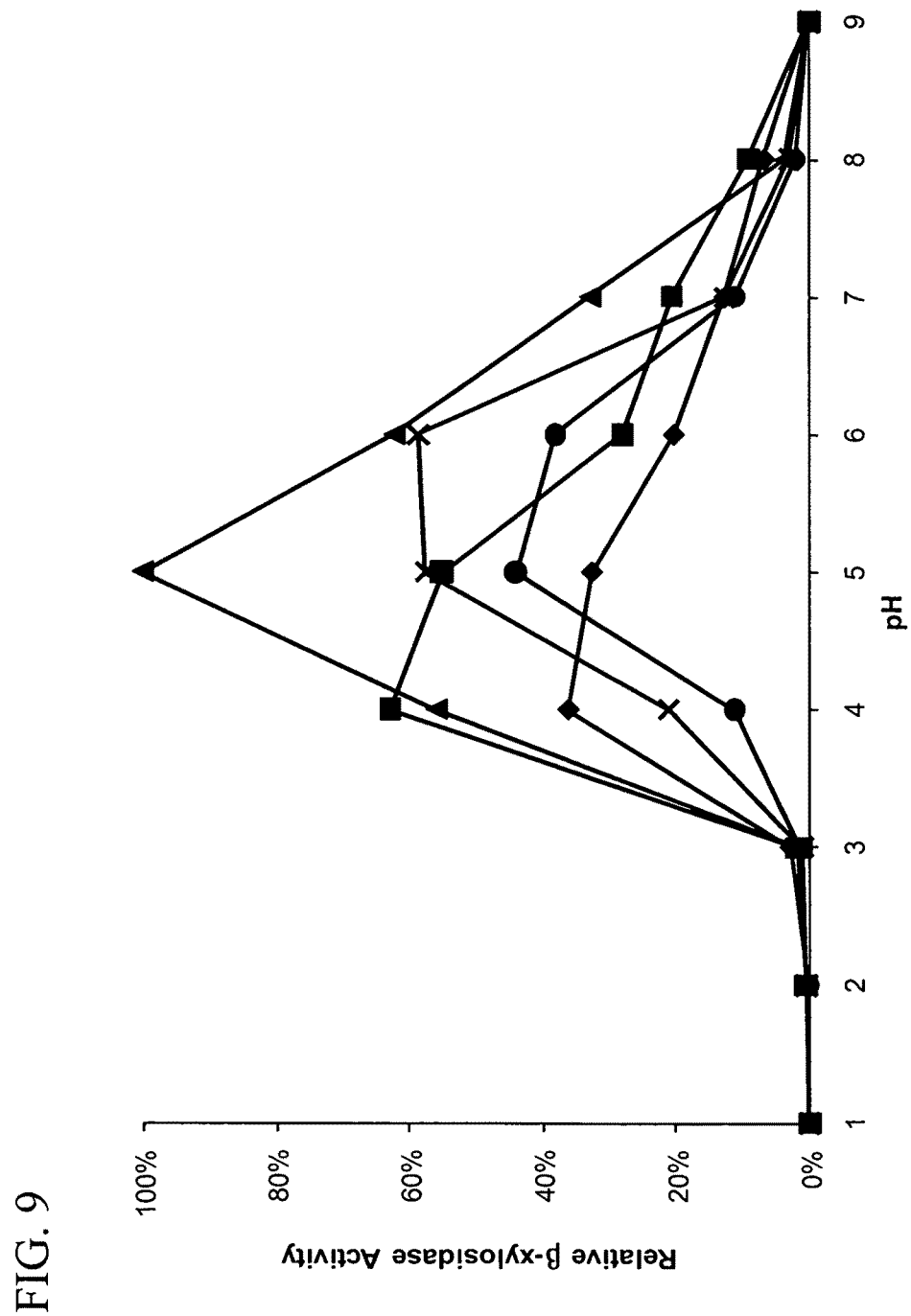
FIG. 9 is a graph depicting β-xylosidase activity of purified SEQ ID NO:1 (RAAC00307), produced in *P. pastoris*, at various combinations of temperature and pH. Data are presented relative to the maximum (highest) measured activity. Diamonds indicate a temperature of 50° C.; squares, 60° C.; triangles, 70° C.; Xs, 80° C.; and circles, 90° C.

The results for purified RAAC00307 expressed in E. coli are depicted in FIG. 7, while the results for purified RAAC00307 expressed in P. pastoris are depicted in FIG. 9.

Example 8

Alpha-L-Arabinofuranosidase Activity of RAAC00307

RAAC00307 purified from E. coli and P. pastoris was tested for alpha-L-arabinofuranosidase activity using an assay summarized as follows:

A solution of α-arabinofuranoside p-nitrophenol (Sigma Cat. No. N3641) was created by diluting 271.2 mg of α-arabinofuranoside p-nitrophenol in 10 mL methanol. Individual aliquots of this solution were then diluted 1:50 with a 50 mM buffer appropriate for one of pH 1, 2, 3, 4, 5, 6, 7, 8, or 9. Glycine HCl buffer was used for pH 1, 2 and 3; sodium acetate buffer was used for pH 4 and 5; phosphate buffer was used for pH 6 and 7; and Tris buffer was used for pH 8 and 9.

Samples of purified RAAC00307 generated in Example 5 were diluted 1:5, 1:10, 1:20, 1:50 and 1:100 in a 50 mM buffer appropriate for one of pH 1, 2, 3, 4, 5, 6, 7, 8, or 9. Glycine HCl buffer was used for pH 1, 2 and 3; sodium acetate buffer was used for pH 4 and 5; phosphate buffer was used for pH 6 and 7; and Tris buffer was used for pH 8 and 9. Samples (RAAC00307 samples and positive controls) were placed the wells of a 96-well plate in 10 μL aliquots. Blanks of buffer only were placed in some wells. One hundred ninety μL of α-arabinofuranoside p-nitrophenol solution, preheated to 50, 60, 70, 80, or 90 degrees Celsius, was then added to each cell and the plate further incubated at to 50, 60, 70, 80, or 90 degrees Celsius for an additional 10 minutes. One hundred μL of 2.0 M sodium carbonate was then added to each well and the α-arabinofuranosidase activity was measured in a 96-well plate reader (Molecular Devices UV-Vis) at a wavelength of 405 nm.

Figure 8:
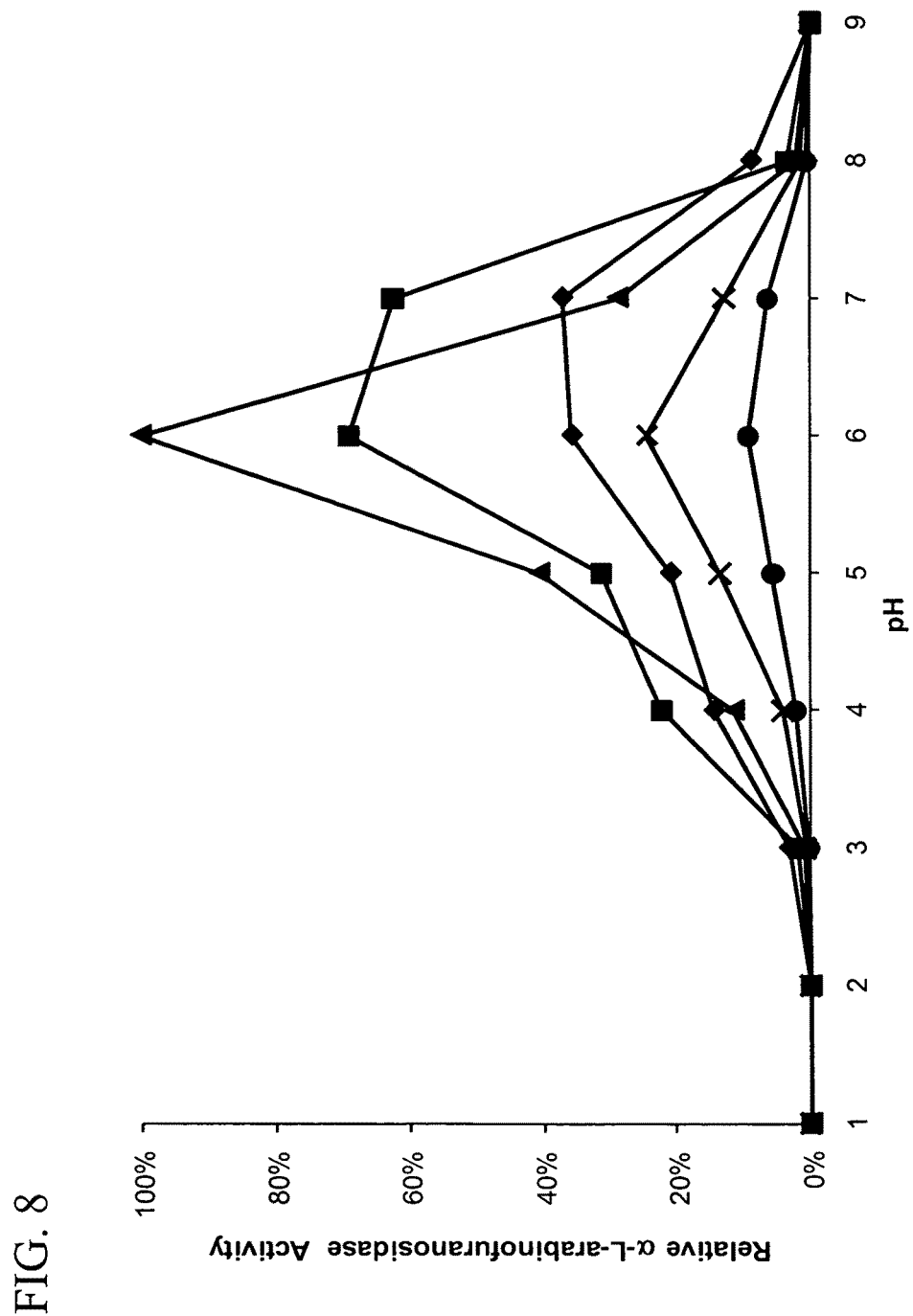
FIG. 8 is a graph depicting the α-L-arabinofuranosidase activity of purified SEQ ID NO:1 (RAAC00307), produced in *E. coli*, at various combinations of temperature and pH. Data are presented relative to the maximum (highest) measured activity. Diamonds indicate a temperature of 50° C.; squares, 60° C.; triangles, 70° C.; Xs, 80° C.; and circles, 90° C.
Figure 10:
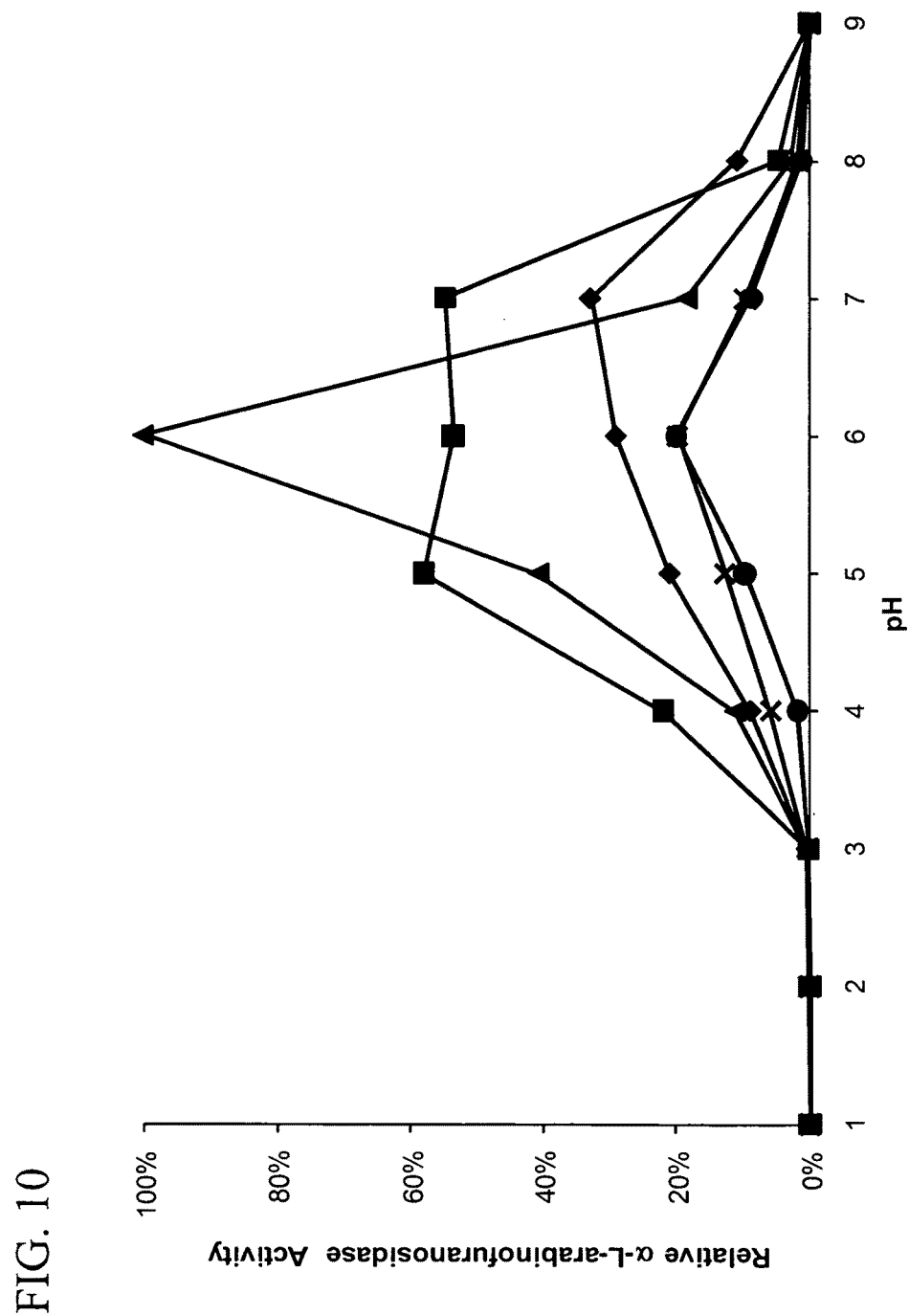
FIG. 10 is a graph depicting α-L-arabinofluranosidase activity of purified SEQ ID NO:1 (RAAC00307), produced in *P. pastoris*, at various combinations of temperature and pH. Data are presented relative to the maximum (highest) measured activity. Diamonds indicate a temperature of 50° C.; squares, 60° C.; triangles, 70° C.; Xs, 80° C.; and circles, 90° C.

The results for purified RAAC00307 expressed in E. coli are depicted in FIG. 8, while the results for purified RAAC00307 expressed in P. pastoris are depicted in FIG. 10.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains and which fall within the limits of the appended claims and their legal equivalents.

Bibliographic References

1. Barany, F., 1991, *PNAS*, USA 88:189-193.
2. Bertoldo et al., 2004, Eng. Life Sci. 4, No. 6.
3. Buckholz, R. G., 1993, Yeast Systems for the Expression of Heterologous Gene Products, *Curr. Op. Biotechnology* 4:538-542.
4. Burg, J. L. et al., 1996, *Mol. and Cell. Probes* 10:257-271.
5. Chu, B. C. F. et al., 1986, *NAR* 14:5591-5603.
6. Duck, P. et al., 1990, *Biotechniques* 9:142-147.
7. Edwards, C. P., and A. Aruffo, 1993, Current Applications of COS Cell-Based Transient Expression Systems, *Curr. Op. Biotechnology* 4:558-563.
8. Garrote, G., H. Dominguez, and J. C. Parajo, 2001, Manufacture of Xylose-Based Fermentation Media from Corncobs by Post-Hydrolysis of Autohydrolysis Liquors, *Appl. Biochem. Biotechnol.* 95:195-207.
9. Guateli, J. C. et al., 1990, *PNAS, USA* 87:1874-1878.
10. Hamelinck C. N., G. van Hooijdonk, and A. P. C. Faaij, 2005, Ethanol from Lignocellulosic Biomass: Techno-Economic Performance in Short-, Middle-, and Long-Term, *Biomass Bioenergy* 28:384-410.
11. Houben-Weyl, 1974, *Methoden der Organischen Chemie*, E. Wunsch ed., Vols. 15-I and 15-II, Thieme, Stuttgart.
12. Huygen, K. et al., 1996, *Nature Medicine* 2(8):893-898.
13. Innis, M.A. et al., 1990, in: *PCR Protocols, A Guide to Methods and Applications*, San Diego, Academic Press.
14. Jeffries, J. W., 1996, *Curr. Op. in Biotech.* 7:337-342.
15. Kievitis, T. et al., 1991, *J. Virol. Methods* 35:273-286.
16. Köhler G. et al., 1975, *Nature* 256(5517):495-497.
17. Kwoh, D.Y. et al., 1989, *PNAS*, USA 86:1173-1177.
18. Liu, C. and C. E. Wyman, 2003, The Effect of Flow Rate of Compressed Hot Water on Xylan, Lignin, and Total Mass Removal from Corn Stover, *Ind. Eng. Chem. Res.* 42:5409-5416.
19. Loontiens, F. G. and C. K. DeBruyne, 1965, *Naturwissenschaften* 52:661.

20. Luckow, V. A., 1993, Baculovirus Systems for the Expression of Human Gene Products, *Curr. Op. Biotechnology* 4:564-572.
21. Lynd et al., 2002, *Micro. and Mol. Biol. Rev.*, Vol. 66, No. 3, pp. 506-577.
22. Malherbe and Cloete, 2002, *Reviews in Environmental Science and Bio/Technology* 1:105-114.
23. Matthews, J. A. et al., 1988, *Analy. Biochem.* 169:1-25.
24. Merrifield, R. D., 1966, *J. Am. Chem. Soc.* 88(21):5051-5052.
25. Miele, E. A. et al., 1983, *J. Mol. Biol.* 171:281-295.
26. Mielenz, 2001, *Curr. Op. in Micro.* 4:324-329.
27. Olins, P. O., and S. C. Lee, 1993, Recent Advances in Heterologous Gene Expression in *E. coli, Curr. Op. Biotechnology* 4:520-525.
28. Rolfs, A. et al., 1991, *in PCR Topics*. Usage of Polymerase Chain Reaction in Genetic and Infectious Disease, Berlin: Springer-Verlag.
29. Sambrook, J. et al., 1989, *Molecular Cloning: A Laboratory Manual*, Cold Spring Harbor, N.Y.: Cold Spring Harbor Laboratory Press.
30. Sanchez-Pescador R., 1988, *J. Clin. Microbiol.* 26(10): 1934-1938.
31. Segev, D., 1992, in *"Non-radioactive Labeling and Detection of Biomolecules,"* C. Kessler, ed., Springer-Verlag, Berlin, New York pp. 197-205.
32. Shallom and Shoham, 2003, *Curr. Op. in Micro.* 6:219-228.
33. Tsao, G. T., M. R. Ladisch, and H. R. Bungay, 1987, Biomass Refining, *in: Advanced Biochemical Engineering*, Wiley Interscience, N.Y., pp. 79-101.
34. Urdea, M. S., 1988, *Nucleic Acids Research*, II:4937-4957.
35. Vieille and Zeikus, 2001, *Micro. and Mol. Biol. Rev., Vol.* 65, No. 1, pp. 1-43.
36. Walker, G. T. et al., 1992, *NAR* 20:1691-1696.
37. Walker, G. T. et al., 1992, *PNAS*, USA 89:392-396.
38. White, B. A. et al., 1997, *Methods in Molecular Biology*, 67, Humana Press, Totowa, N.J.

What is claimed is:

1. An isolated polypeptide comprising a polypeptide having at least 95% sequence identity to the polypeptide of SEQ ID NO:2;
   wherein the polypeptide exhibits beta-xylosidase enzyme activity.

2. The isolated polypeptide of claim 1, wherein the polypeptide exhibits enzymatic activity at or below about a pH of 8.

3. The isolated polypeptide of claim 1, wherein the polypeptide exhibits enzymatic activity at a temperature at or above about 50degrees Celsius.

4. The isolated polypeptide of claim 1, wherein the polypeptide is glycosylated, pegylated, or otherwise post-translationally modified.

5. The isolated polypeptide of claim 1, wherein the polypeptide further exhibits arabinofuranosidase enzyme activity.

6. A method of at least partially degrading xylotriose or xylobiose, the method comprising:
   providing the isolated polypeptide of claim 1 and placing the polypeptide in fluid contact with xylotriose or xylobiose.

7. A method of at least partially degrading arabinofuranose-substituted xylan, the method comprising:

providing the isolated polypeptide of claim 1 and placing the polypeptide in fluid contact with arabinofuranose-substituted xylan.

8. The method according to claim 7, wherein the polypeptide exhibits arabinofuranosidase activity.

9. The isolated polypeptide of claim 5, wherein the polypeptide exhibits enzymatic activity at or below about a pH of 8.

10. The isolated polypeptide of claim 5, wherein the polypeptide exhibits enzymatic activity at a temperature at or above about 50 degrees Celsius.

11. The isolated polypeptide of claim 5, wherein the polypeptide is glycosylated, pegylated, or otherwise post-translationally modified.

\* \* \* \* \*

UNITED STATES PATENT AND TRADEMARK OFFICE
CERTIFICATE OF CORRECTION

PATENT NO.      : 8,431,379 B2
APPLICATION NO. : 12/802911
DATED           : April 30, 2013
INVENTOR(S)     : David N. Thompson et al.

It is certified that error appears in the above-identified patent and that said Letters Patent is hereby corrected as shown below:

On the title page:
In ITEM (54) the Title:
  LINES 1-2,   change "BETA XYLOSIDASES," to --BETA-XYLOSIDASES,--

In ITEM (56) References Cited:
  OTHER PUBLICATIONS
  Page 2, 2nd column, 1st line of the
    9th entry (line 16),   change "(CeIB)," to --(CelB),--
  Page 2, 2nd column, 2nd line of the
    10th entry (line 19),  change "(CeIA)" to --(CelA)--
  Page 4, 1st column, 1st line of the
    10th entry (line 24),  change "2,2-bicinchoninic-based" to --2,2'-bicinchoninic-based--

In the specification:
  COLUMN 1,  LINES 1-2,  change "BETA XYLOSIDASES," to --BETA-XYLOSIDASES,--
  COLUMN 1,  LINE 22,    change "DE-ACO7-991D" to --DE-AC07-99ID--
  COLUMN 1,  LINE 23,    change "DE-ACO7-051D" to --DE-AC07-05ID--
  COLUMN 4,  LINE 17,    change "α-L-arabinofluranosidase" to --α-L-arabinofuranosidase--
  COLUMN 21, LINE 65,    change "SEQ ID NOS:2" to --SEQ ID NOs:2--
  COLUMN 22, LINE 44,    change "from *A niger*" to --from *A. niger*--
  COLUMN 22, LINE 56,    change "355 nm" to --at 355 nm--
  COLUMN 23, LINE 32,    change "placed the" to --placed in the--
  COLUMN 23, LINE 36,    change "each cell" to --each well--
  COLUMN 24, LINE 59,    change "15. Kievitis," to --15. Kievits,--

Signed and Sealed this
Twenty-first Day of June, 2016

Michelle K. Lee
*Director of the United States Patent and Trademark Office*

CERTIFICATE OF CORRECTION (continued)
U.S. Pat. No. 8,431,379 B2

In the claims:

CLAIM 3, COLUMN 81, LINE 67,          change "50degrees" to --50 degrees--

SEQUENCE LISTING

<160> NUMBER OF SEQ ID NOS: 17

<210> SEQ ID NO 1
<211> LENGTH: 2397
<212> TYPE: DNA
<213> ORGANISM: Alicyclobacillus acidocaldarius

<400> SEQUENCE: 1

```
ttgaatgtga aggcggcgtc agcgcctgat gagcagagga ggcttcccgt gacaccgtg      60 tatctcgatc ccgcacagtc cattgaagcg cgcgtcgacg cgctcctggc cgatatgacg     120
cttgaagaaa aggtcgctca actcacgtcc atctgggcgt tcgaagtcct ggatgagctc     180
gagttctccg ccgagaaggc cgccgccgtg ctcgggcagg gcatcggaca ggtgacccga     240
attggcggcg ccaccaatct ggacccgccg gatgtggccc gcctcgccaa ccagattcag     300
cgctacctgc gcgatcacac gcgcctcggc attccggcgc tgatccacga ggagtcgtgc     360
agcggctaca tggccaaggg cgccacctgc tttccgcaaa ccattggcat cgcgagcacg     420
tgggatgtcg atctcgcccg ccgtattggc gccatcatcc gcgatcagat gcgggccgtc     480
ggggcgcgcc aggcgctcgc cccgctcctg gatgtggcac gagatccgcg ctggggccgg     540
gtggaggaga cgttcggcga agatccgtac ctcgtggcgc agatgggcat cgcgtacgtc     600
cgcgggctgc agggagacga cctgagccag ggcgtgatgg cgacgggcaa gcacttcgtg     660
ggctacgggg cgtccgaggg cggcatgaac tgggcgccgg cgcacatccc ggagcgcgag     720
ctgcgcgagg tgtacctgtt cccgttcgag gcggcggtgc gcgaggcggg gctcggcgcc     780
atcatgccgg ggtaccacga gctcgacggc gtgccctgcc acgacaatcc agggcttttg     840
cgcgagaccc tccgcgggcg ctggggcttt caggggctcg tggtgtcgga ctatttcgcc     900
gtgaatcagc tgttcgaata tcatcaggtg gcccgggaca aggcggaggc cgcggcgctc     960
gccgtgcgcg ccggggtgga cgtggagctg ccgacgcgcg acgtgtacgg caagccgctc    1020
atcgaggccg ttgcacgagg gctcgtcagc ccggccgaga tcgacgaact cgtgcgccgg    1080
gtgctcacgt ggaagttccg gctcggcctc ttcgatcacc cgtttgtcga cgagggcgcg    1140
gccatcgccg tcttcgacaa cgcggagcag cgtcaggtgg cgcgggaggc ggcggagaag    1200
tcgatggtcc tcctcaaaaa cgacgggctt ctgccctcg cgccccgcgg caccatcgcc    1260
```

```
gtgatcggcc caaacgcgca cacgacgcgc aatttggtag gcgattacgc ctacccgtgc    1320
cacatcgagt cgctcctcga gcagtccgag acaacgtgt ttcagacccc gcttccgagc    1380
ggcgtgaaac acgtggacga gttcatcctc atgcggacca tcctcgaggc catccgccat    1440
cgcgtcgggt cggaggcgca ggtcgtctac gcgaaggggt gcgacatcct cggcggtgag    1500
gatgcggagc tcgaggaggc ggtggcgctt ccgcgaagg cggacgtggc ggttgtggtg    1560
gtgggcgatc gcgccgggct cacggacgcg tgcacgacag gggaatcgcg agacagagcc    1620
acgctctcgc tcatcgggcg gcaggaggaa ctcgtgcggc gcgtaatcgc cacgggcacg    1680
aagacggtcg tggtgctcgt gagcgggcgg ccgctcgcca tcccggacat cgcggagcgg    1740
gcgaacgccg ttctcgaggc gtggctgccg gcgaggaag gcgcggaggc ggtggccgcg    1800
gtcctgtttg gcgacgtgaa tccgtccggg aagctgccca tcacgattcc gcgcagcgtg    1860
ggccaggtgc caatttacta cgggcacaag ccgtcgggcg gccgctcgca ctggaagggc    1920
gcgtatgtgg acgagagcaa tctgccgctc tatccgtttg gcacgggct gtcctacacg    1980 gcgttcgcgt accgggatct ggcgctgtct ccgagcgtcc tgggcgtgca cggcgaggtc    2040
gaggtgtcgt gcgtgatcga aaacgtcggg gctcgcgcgg gcgaagaggt ggtgcaactg    2100
tacgcacgcg acgtggcggc ggacgtgacg cggccggtga aggcgctctg cggctttgcg    2160
cgggtggcgc tcgcgccggg agagaaggcg cgagtgcggt tccgggtttc agcgcaccag    2220
ttcggcttct acaaccggga gatgcggtat gtcgtggagc cgggcgagat cgagttcatg    2280 gtggggcgt cgtccgagga catccgcctg cgcggggcgg tgcggatgga cggcgcggtg    2340
acggagatcg agcacgagaa ggtataccag agcgcggtgg acgtcgagcg gatgtga      2397
```

<210> SEQ ID NO 2
<211> LENGTH: 798
<212> TYPE: PRT
<213> ORGANISM: Alicyclobacillus acidocaldarius

<400> SEQUENCE: 2

```
Met Asn Val Lys Ala Ala Ser Ala Pro Asp Glu Gln Arg Arg Leu Pro
  1               5                  10                  15

Val Thr Pro Val Tyr Leu Asp Pro Ala Gln Ser Ile Glu Ala Arg Val
                 20                  25                  30

Asp Ala Leu Leu Ala Asp Met Thr Leu Glu Glu Lys Val Ala Gln Leu
             35                  40                  45

Thr Ser Ile Trp Ala Phe Glu Val Leu Asp Glu Leu Glu Phe Ser Ala
         50                  55                  60

Glu Lys Ala Ala Ala Val Leu Gly Gln Gly Ile Gly Gln Val Thr Arg
 65                  70                  75                  80

Ile Gly Gly Ala Thr Asn Leu Asp Pro Asp Val Ala Arg Leu Ala
                 85                  90                  95

Asn Gln Ile Gln Arg Tyr Leu Arg Asp His Thr Arg Leu Gly Ile Pro
                100                 105                 110

Ala Leu Ile His Glu Glu Ser Cys Ser Gly Tyr Met Ala Lys Gly Ala
            115                 120                 125

Thr Cys Phe Pro Gln Thr Ile Gly Ile Ala Ser Thr Trp Asp Val Asp
        130                 135                 140

Leu Ala Arg Arg Ile Gly Ala Ile Ile Arg Asp Gln Met Arg Ala Val
145                 150                 155                 160

Gly Ala Arg Gln Ala Leu Ala Pro Leu Leu Asp Val Ala Arg Asp Pro
                165                 170                 175

Arg Trp Gly Arg Val Glu Glu Thr Phe Gly Glu Asp Pro Tyr Leu Val
```

```
                    180                 185                 190
Ala Gln Met Gly Ile Ala Tyr Val Arg Gly Leu Gln Gly Asp Asp Leu
            195                 200                 205

Ser Gln Gly Val Met Ala Thr Gly Lys His Phe Val Gly Tyr Gly Ala
            210                 215                 220

Ser Glu Gly Gly Met Asn Trp Ala Pro Ala His Ile Pro Glu Arg Glu
225                 230                 235                 240

Leu Arg Glu Val Tyr Leu Phe Pro Phe Glu Ala Val Arg Glu Ala
            245                 250                 255

Gly Leu Gly Ala Ile Met Pro Gly Tyr His Glu Leu Asp Gly Val Pro
            260                 265                 270

Cys His Asp Asn Pro Gly Leu Leu Arg Glu Thr Leu Arg Gly Arg Trp
            275                 280                 285

Gly Phe Gln Gly Leu Val Val Ser Asp Tyr Phe Ala Val Asn Gln Leu
            290                 295                 300

Phe Glu Tyr His Gln Val Ala Arg Asp Lys Ala Glu Ala Ala Leu
305                 310                 315                 320

Ala Val Arg Ala Gly Val Asp Val Glu Leu Pro Thr Arg Asp Val Tyr
            325                 330                 335

Gly Lys Pro Leu Ile Glu Ala Val Ala Arg Gly Leu Val Ser Pro Ala
            340                 345                 350

Glu Ile Asp Glu Leu Val Arg Arg Val Leu Thr Trp Lys Phe Arg Leu
            355                 360                 365

Gly Leu Phe Asp His Pro Phe Val Asp Glu Gly Ala Ala Ile Ala Val
            370                 375                 380

Phe Asp Asn Ala Glu Gln Arg Gln Val Ala Arg Glu Ala Ala Glu Lys
385                 390                 395                 400

Ser Met Val Leu Leu Lys Asn Asp Gly Leu Leu Pro Leu Ala Pro Arg
            405                 410                 415

Gly Thr Ile Ala Val Ile Gly Pro Asn Ala His Thr Thr Arg Asn Leu
            420                 425                 430

Val Gly Asp Tyr Ala Tyr Pro Cys His Ile Glu Ser Leu Leu Glu Gln
            435                 440                 445

Ser Glu Asp Asn Val Phe Gln Thr Pro Leu Pro Ser Gly Val Lys His
            450                 455                 460

Val Asp Glu Phe Ile Leu Met Arg Thr Ile Leu Glu Ala Ile Arg His
465                 470                 475                 480

Arg Val Gly Ser Glu Ala Gln Val Val Tyr Ala Lys Gly Cys Asp Ile
            485                 490                 495

Leu Gly Gly Glu Asp Ala Glu Leu Glu Glu Ala Val Ala Leu Ala Ala
            500                 505                 510

Lys Ala Asp Val Ala Val Val Val Gly Asp Arg Ala Gly Leu Thr
            515                 520                 525

Asp Ala Cys Thr Thr Gly Glu Ser Arg Asp Arg Ala Thr Leu Ser Leu
            530                 535                 540

Ile Gly Arg Gln Glu Glu Leu Val Arg Val Ile Ala Thr Gly Thr
545                 550                 555                 560

Lys Thr Val Val Val Leu Val Ser Gly Arg Pro Leu Ala Ile Pro Asp
            565                 570                 575

Ile Ala Glu Arg Ala Asn Ala Val Leu Glu Ala Trp Leu Pro Gly Glu
            580                 585                 590

Glu Gly Ala Glu Ala Val Ala Ala Val Leu Phe Gly Asp Val Asn Pro
            595                 600                 605
```

```
Ser Gly Lys Leu Pro Ile Thr Ile Pro Arg Ser Val Gly Gln Val Pro
        610                 615                 620

Ile Tyr Tyr Gly His Lys Pro Ser Gly Gly Arg Ser His Trp Lys Gly
625                 630                 635                 640

Ala Tyr Val Asp Glu Ser Asn Leu Pro Leu Tyr Pro Phe Gly His Gly
                645                 650                 655

Leu Ser Tyr Thr Ala Phe Ala Tyr Arg Asp Leu Ala Leu Ser Pro Ser
            660                 665                 670

Val Leu Gly Val His Gly Glu Val Glu Val Ser Cys Val Ile Glu Asn
        675                 680                 685

Val Gly Ala Arg Ala Gly Glu Glu Val Val Gln Leu Tyr Ala Arg Asp
    690                 695                 700

Val Ala Ala Asp Val Thr Arg Pro Val Lys Ala Leu Cys Gly Phe Ala
705                 710                 715                 720

Arg Val Ala Leu Ala Pro Gly Glu Lys Ala Arg Val Arg Phe Arg Val
                725                 730                 735

Ser Ala His Gln Phe Gly Phe Tyr Asn Arg Glu Met Arg Tyr Val Val
            740                 745                 750

Glu Pro Gly Glu Ile Glu Phe Met Val Gly Ala Ser Ser Glu Asp Ile
        755                 760                 765

Arg Leu Arg Gly Ala Val Arg Met Asp Gly Ala Val Thr Glu Ile Glu
    770                 775                 780

His Glu Lys Val Tyr Gln Ser Ala Val Asp Val Glu Arg Met
785                 790                 795

<210> SEQ ID NO 3
<211> LENGTH: 784
<212> TYPE: PRT
<213> ORGANISM: Thermoanaerobacter ethanolicus ATCC 33223

<400> SEQUENCE: 3

Met Thr Pro Leu Tyr Leu Asp Ser Thr Gln Ser Val Glu Lys Arg Val
1               5                   10                  15

Glu Asp Leu Leu Gln Gln Met Thr Ile Glu Glu Lys Val Ala Gln Leu
            20                  25                  30

Asn Ser Ile Trp Val Tyr Glu Ile Leu Asp Asp Met Lys Phe Ser Phe
        35                  40                  45

Asp Lys Ala Lys Arg Leu Met Ser Tyr Gly Ile Gly Gln Ile Thr Arg
    50                  55                  60

Leu Gly Gly Ala Ser Asn Leu Ser Pro Arg Glu Thr Val Arg Ile Ala
65                  70                  75                  80

Asn Gln Ile Gln Lys Phe Leu Ile Glu Asn Thr Arg Leu Gly Ile Pro
                85                  90                  95

Ala Leu Ile His Glu Glu Ser Cys Ser Gly Tyr Met Ala Lys Gly Ala
            100                 105                 110

Thr Ile Phe Pro Gln Thr Ile Gly Val Ala Ser Thr Trp Asn Asn Glu
        115                 120                 125

Ile Val Glu Lys Met Ala Ser Val Ile Arg Glu Gln Met Lys Ala Val
    130                 135                 140

Gly Ala Arg Gln Ala Leu Ala Pro Leu Leu Asp Ile Thr Arg Asp Pro
145                 150                 155                 160

Arg Trp Gly Arg Thr Glu Glu Thr Phe Gly Glu Asp Pro Tyr Leu Val
                165                 170                 175

Met Arg Met Gly Val Ser Tyr Ile Arg Gly Leu Gln Thr Glu Ser Leu
            180                 185                 190
```

-continued

```
Lys Glu Gly Ile Val Ala Thr Gly Lys His Phe Val Gly Tyr Gly Asn
            195                 200                 205

Ser Glu Gly Gly Met Asn Trp Ala Pro Ala His Ile Pro Glu Arg Glu
        210                 215                 220

Leu Arg Glu Val Phe Leu Tyr Pro Phe Glu Ala Val Lys Glu Ala
225                 230                 235                 240

Lys Leu Ser Ser Ile Met Pro Gly Tyr His Glu Leu Asp Gly Val Pro
                245                 250                 255

Cys His Lys Ser Lys Lys Leu Leu Asn Asp Ile Leu Arg Lys Asp Trp
                    260                 265                 270

Gly Phe Glu Gly Ile Val Val Ser Asp Tyr Phe Ala Ile Ser Gln Leu
            275                 280                 285

Tyr Glu Tyr His His Val Thr Ser Asp Lys Lys Gly Ala Ala Lys Leu
        290                 295                 300

Ala Leu Glu Ala Gly Val Asp Val Glu Leu Pro Ser Thr Asp Tyr Tyr
305                 310                 315                 320

Gly Leu Pro Leu Arg Glu Leu Ile Glu Ser Gly Glu Ile Asp Ile Asp
                325                 330                 335

Phe Val Asn Glu Ala Val Lys Arg Val Leu Lys Ile Lys Phe Glu Leu
                    340                 345                 350

Gly Leu Phe Glu Asn Pro Tyr Ile Asn Glu Glu Lys Ala Val Glu Ile
            355                 360                 365

Phe Asp Thr Asn Glu Gln Arg Glu Leu Ala Tyr Lys Ile Ala Gln Glu
        370                 375                 380

Ser Ile Val Leu Leu Lys Asn Glu Asn Asn Leu Leu Pro Leu Lys Lys
385                 390                 395                 400

Asp Leu Lys Ser Ile Ala Val Ile Gly Pro Asn Ala Asp Ser Ile Arg
                405                 410                 415

Asn Met Ile Gly Asp Tyr Ala Tyr Pro Cys His Ile Glu Ser Leu Leu
                    420                 425                 430

Glu Met Arg Glu Thr Asp Asn Val Phe Asn Thr Pro Leu Pro Glu Ser
            435                 440                 445

Leu Glu Ala Lys Asp Ile Tyr Val Pro Ile Val Thr Val Leu Gln Gly
        450                 455                 460

Ile Lys Ala Lys Val Ser Ser Asn Thr Glu Val Leu Tyr Ala Lys Gly
465                 470                 475                 480

Cys Asp Val Leu Asn Asn Ser Lys Asp Gly Phe Lys Glu Ala Val Glu
                485                 490                 495

Ile Ala Lys Gln Ala Asp Val Ala Val Val Val Gly Asp Lys Ser
                    500                 505                 510

Gly Leu Thr Asp Gly Cys Thr Ser Gly Glu Ser Arg Asp Arg Ala Asp
            515                 520                 525

Leu Asn Leu Pro Gly Val Gln Glu Glu Leu Ile Lys Ala Ile Tyr Glu
        530                 535                 540

Thr Gly Thr Pro Val Ile Val Val Leu Ile Asn Gly Arg Pro Met Ser
545                 550                 555                 560

Ile Ser Trp Ile Ala Glu Lys Ile Pro Ala Ile Glu Ala Trp Leu
                565                 570                 575

Pro Gly Glu Glu Gly Gly Arg Ala Val Ala Asp Val Ile Phe Gly Asp
                    580                 585                 590

Tyr Asn Pro Gly Gly Lys Leu Pro Ile Ser Ile Pro Gln Ser Val Gly
            595                 600                 605

Gln Leu Pro Val Tyr Tyr Tyr His Lys Pro Ser Gly Gly Arg Ser His
        610                 615                 620
```

-continued

```
Trp Lys Gly Asp Tyr Val Glu Leu Ser Thr Lys Pro Leu Tyr Pro Phe
625                 630                 635                 640

Gly Tyr Gly Leu Ser Tyr Thr Glu Phe Ser Tyr Thr Asn Leu Asn Ile
            645                 650                 655

Ser Asn Arg Lys Val Ser Leu Arg Asp Arg Met Val Glu Ile Ser Val
                660                 665                 670

Asp Ile Lys Asn Thr Gly Thr Leu Lys Gly Asp Glu Val Val Gln Leu
            675                 680                 685

Tyr Ile His Gln Glu Ala Leu Ser Val Thr Arg Pro Val Lys Glu Leu
        690                 695                 700

Lys Gly Phe Lys Arg Ile Thr Leu Asp Ala Gly Glu Lys Thr Val
705                 710                 715                 720

Ile Phe Lys Leu Ser Ile Glu Gln Leu Gly Phe Tyr Asp Glu Asn Met
                725                 730                 735

Glu Tyr Val Val Glu Pro Gly Arg Val Asp Val Met Ile Gly Ser Ser
            740                 745                 750

Ser Glu Asp Ile Arg Leu Arg Asp Tyr Phe Glu Ile Val Gly Glu Lys
        755                 760                 765

Glu Lys Val Ala Lys Lys Phe Ile Thr Glu Val Arg Val Glu Asn Lys
770                 775                 780

<210> SEQ ID NO 4
<211> LENGTH: 778
<212> TYPE: PRT
<213> ORGANISM: Thermotoga maritima MSB8

<400> SEQUENCE: 4

Met Glu Leu Tyr Arg Asp Pro Ser Gln Pro Ile Glu Val Arg Val Arg
1               5                   10                  15

Asp Leu Leu Ser Arg Met Thr Leu Glu Glu Lys Val Ala Gln Leu Gly
            20                  25                  30

Ser Val Trp Gly Tyr Glu Leu Ile Asp Glu Arg Gly Lys Phe Ser Arg
        35                  40                  45

Glu Lys Ala Lys Glu Leu Leu Lys Asn Gly Ile Gly Gln Ile Thr Arg
50                  55                  60

Pro Gly Gly Ser Thr Asn Leu Glu Pro Gln Glu Ala Ala Glu Leu Val
65                  70                  75                  80

Asn Glu Ile Gln Arg Phe Leu Val Glu Thr Arg Leu Gly Ile Pro
                85                  90                  95

Ala Met Ile His Glu Glu Cys Leu Thr Gly Tyr Met Gly Leu Gly Gly
            100                 105                 110

Thr Asn Phe Pro Gln Ala Ile Ala Met Ala Ser Thr Trp Asp Pro Asp
        115                 120                 125

Leu Ile Glu Lys Met Thr Thr Ala Val Arg Glu Asp Met Arg Lys Ile
130                 135                 140

Gly Ala His Gln Gly Leu Ala Pro Val Leu Asp Val Ala Arg Asp Pro
145                 150                 155                 160

Arg Trp Gly Arg Thr Glu Glu Thr Phe Gly Glu Ser Pro Tyr Leu Val
                165                 170                 175

Ala Arg Met Gly Val Ser Tyr Val Lys Gly Leu Gln Gly Glu Asp Ile
            180                 185                 190

Lys Lys Gly Val Val Ala Thr Val Lys His Phe Ala Gly Tyr Ser Ala
        195                 200                 205

Ser Glu Gly Gly Lys Asn Trp Ala Pro Thr Asn Ile Pro Glu Arg Glu
210                 215                 220
```

```
Phe Lys Glu Val Phe Leu Phe Pro Phe Glu Ala Ala Val Lys Glu Ala
225                 230                 235                 240

Asn Val Leu Ser Val Met Asn Ser Tyr Ser Glu Ile Asp Gly Val Pro
            245                 250                 255

Cys Ala Ala Asn Arg Lys Leu Leu Thr Asp Ile Leu Arg Lys Asp Trp
                260                 265                 270

Gly Phe Glu Gly Ile Val Val Ser Asp Tyr Phe Ala Val Lys Val Leu
            275                 280                 285

Glu Asp Tyr His Arg Ile Ala Arg Asp Lys Ser Glu Ala Ala Arg Leu
        290                 295                 300

Ala Leu Glu Ala Gly Ile Asp Val Glu Leu Pro Lys Thr Glu Cys Tyr
305                 310                 315                 320

Gln Tyr Leu Lys Asp Leu Val Glu Lys Gly Ile Ile Ser Glu Ala Leu
                325                 330                 335

Ile Asp Glu Ala Val Thr Arg Val Leu Arg Leu Lys Phe Met Leu Gly
                340                 345                 350

Leu Phe Glu Asn Pro Tyr Val Glu Val Glu Lys Ala Lys Ile Glu Ser
            355                 360                 365

His Arg Asp Ile Ala Leu Glu Ile Ala Arg Lys Ser Ile Ile Leu Leu
        370                 375                 380

Lys Asn Asp Gly Ile Leu Pro Leu Gln Lys Asn Lys Lys Val Ala Leu
385                 390                 395                 400

Ile Gly Pro Asn Ala Gly Glu Val Arg Asn Leu Leu Gly Asp Tyr Met
                405                 410                 415

Tyr Leu Ala His Ile Arg Ala Leu Leu Asp Asn Ile Asp Asp Val Phe
                420                 425                 430

Gly Asn Pro Gln Ile Pro Arg Glu Asn Tyr Glu Arg Leu Lys Lys Ser
            435                 440                 445

Ile Glu Glu His Met Lys Ser Ile Pro Ser Val Leu Asp Ala Phe Lys
450                 455                 460

Glu Gly Ile Glu Phe Glu Tyr Ala Lys Gly Cys Glu Val Thr Gly
465                 470                 475                 480

Glu Asp Arg Ser Gly Phe Glu Ala Ile Glu Ile Ala Lys Lys Ser
                485                 490                 495

Asp Val Ala Ile Val Val Gly Asp Lys Ser Gly Leu Thr Leu Asp
                500                 505                 510

Cys Thr Thr Gly Glu Ser Arg Asp Met Ala Asn Leu Lys Leu Pro Gly
            515                 520                 525

Val Gln Glu Glu Leu Val Leu Glu Val Ala Lys Thr Gly Lys Pro Val
    530                 535                 540

Val Leu Val Leu Ile Thr Gly Arg Pro Tyr Ser Leu Lys Asn Val Val
545                 550                 555                 560

Asp Lys Val Asn Ala Ile Leu Gln Val Trp Leu Pro Gly Glu Ala Gly
                565                 570                 575

Gly Arg Ala Ile Val Asp Ile Ile Tyr Gly Lys Val Asn Pro Ser Gly
            580                 585                 590

Lys Leu Pro Ile Ser Phe Pro Arg Ser Ala Gly Gln Ile Pro Val Phe
        595                 600                 605

His Tyr Val Lys Pro Ser Gly Gly Arg Ser His Trp His Gly Asp Tyr
        610                 615                 620

Val Asp Glu Ser Thr Lys Pro Leu Phe Pro Phe Gly His Gly Leu Ser
625                 630                 635                 640

Tyr Thr Lys Phe Glu Tyr Ser Asn Leu Arg Ile Glu Pro Lys Glu Val
```

```
                      645                 650                 655
Pro Pro Ala Gly Glu Val Val Ile Lys Val Asp Val Glu Asn Ile Gly
            660                 665                 670

Asp Arg Asp Gly Asp Glu Val Val Gln Leu Tyr Ile Gly Arg Glu Phe
            675                 680                 685

Ala Ser Val Thr Arg Pro Val Lys Glu Leu Lys Gly Phe Lys Arg Val
            690                 695                 700

Ser Leu Lys Ala Lys Glu Lys Lys Thr Val Val Phe Arg Leu His Met
705                 710                 715                 720

Asp Val Leu Ala Tyr Tyr Asn Arg Asp Met Lys Leu Val Val Glu Pro
                725                 730                 735

Gly Glu Phe Lys Val Met Val Gly Ser Ser Ser Glu Asp Ile Arg Leu
            740                 745                 750

Thr Gly Ser Phe Ser Val Val Gly Glu Lys Arg Glu Val Val Gly Met
            755                 760                 765

Arg Lys Phe Phe Thr Glu Ala Cys Glu Glu
            770                 775

<210> SEQ ID NO 5
<211> LENGTH: 778
<212> TYPE: PRT
<213> ORGANISM: Thermotoga petrophila RKU-1

<400> SEQUENCE: 5

Met Glu Leu Tyr Arg Asp Pro Ser Gln Pro Ile Glu Val Arg Val Arg
1               5                   10                  15

Asp Leu Leu Ser Arg Met Thr Leu Glu Glu Lys Ala Ala Gln Leu Gly
            20                  25                  30

Ser Val Trp Gly Tyr Glu Leu Ile Asp Glu Arg Gly Lys Phe Ser Arg
        35                  40                  45

Glu Lys Ala Lys Glu Leu Leu Lys Asn Gly Ile Gly Gln Val Thr Arg
50                  55                  60

Pro Gly Gly Ser Thr Asn Leu Glu Pro Gln Glu Ala Ala Glu Leu Val
65                  70                  75                  80

Asn Glu Ile Gln Arg Phe Leu Val Glu Thr Arg Leu Gly Ile Pro
            85                  90                  95

Ala Met Ile His Glu Glu Cys Leu Thr Gly Tyr Met Gly Leu Gly Gly
            100                 105                 110

Thr Asn Phe Pro Gln Ala Ile Ala Met Ala Ser Thr Trp Asp Pro Asp
            115                 120                 125

Leu Ile Glu Lys Met Thr Thr Ala Ile Arg Glu Asp Met Arg Lys Ile
130                 135                 140

Gly Ala His Gln Gly Leu Ala Pro Val Leu Asp Val Ala Arg Asp Pro
145                 150                 155                 160

Arg Trp Gly Arg Thr Glu Glu Thr Phe Gly Glu Ser Pro Tyr Leu Val
            165                 170                 175

Ala Arg Met Gly Val Ser Tyr Val Lys Gly Leu Gln Gly Glu Asp Ile
            180                 185                 190

Lys Lys Gly Val Val Ala Thr Val Lys His Phe Ala Gly Tyr Ser Ala
            195                 200                 205

Ser Glu Gly Gly Lys Asn Trp Ala Pro Thr Asn Ile Pro Glu Arg Glu
            210                 215                 220

Phe Lys Glu Val Phe Leu Phe Pro Glu Ala Ala Val Lys Glu Ala
225                 230                 235                 240

Asn Val Leu Ser Val Met Asn Ser Tyr Ser Glu Ile Asp Gly Val Pro
```

```
                    245                 250                 255
Cys Ala Ala Asn Arg Lys Leu Leu Thr Asp Ile Leu Arg Lys Asp Trp
                260                 265                 270
Gly Phe Lys Gly Ile Val Val Ser Asp Tyr Phe Ala Val Lys Val Leu
            275                 280                 285
Glu Asp Tyr His Arg Ile Ala Arg Asp Lys Ser Glu Ala Ala Arg Leu
        290                 295                 300
Ala Leu Glu Ala Gly Ile Asp Val Glu Leu Pro Lys Thr Glu Cys Tyr
305                 310                 315                 320
Gln Tyr Leu Lys Asp Leu Val Glu Lys Gly Ile Ile Ser Glu Ala Leu
                325                 330                 335
Ile Asp Glu Ala Val Ala Arg Val Leu Arg Leu Lys Phe Met Leu Gly
                340                 345                 350
Leu Phe Glu Asn Pro Tyr Val Glu Val Glu Lys Ala Lys Ile Glu Ser
            355                 360                 365
His Lys Asp Ile Ala Leu Asp Ile Ala Arg Lys Ser Ile Ile Leu Leu
        370                 375                 380
Lys Asn Asp Gly Ile Leu Pro Leu Gln Lys Asn Lys Lys Val Ala Leu
385                 390                 395                 400
Ile Gly Pro Asn Ala Gly Glu Val Arg Asn Leu Leu Gly Asp Tyr Met
                405                 410                 415
Tyr Leu Ala His Ile Arg Ala Leu Leu Asp Asn Ile Asp Val Phe
                420                 425                 430
Gly Asn Pro Gln Ile Pro Arg Glu Asn Tyr Glu Arg Leu Lys Lys Ser
            435                 440                 445
Ile Glu Glu His Met Lys Ser Ile Pro Ser Val Leu Asp Ala Phe Lys
        450                 455                 460
Glu Glu Gly Ile Glu Phe Glu Tyr Ala Lys Gly Cys Glu Val Thr Gly
465                 470                 475                 480
Glu Asp Arg Ser Gly Phe Glu Ala Ile Glu Ile Ala Lys Lys Ser
                485                 490                 495
Asp Val Ala Ile Val Val Gly Asp Lys Ser Gly Leu Thr Leu Asp
            500                 505                 510
Cys Thr Thr Gly Glu Ser Arg Asp Met Ala Asn Leu Lys Leu Pro Gly
        515                 520                 525
Val Gln Glu Glu Leu Val Leu Glu Val Ala Lys Thr Gly Lys Pro Val
        530                 535                 540
Val Leu Val Leu Ile Thr Gly Arg Pro Tyr Ser Leu Lys Asn Val Val
545                 550                 555                 560
Asp Lys Val Asn Ala Ile Leu Gln Val Trp Leu Pro Gly Glu Ala Gly
                565                 570                 575
Gly Arg Ala Ile Val Asp Ile Ile Tyr Gly Lys Val Asn Pro Ser Gly
            580                 585                 590
Lys Leu Pro Ile Ser Phe Pro Arg Ser Ala Gly Gln Ile Pro Val Phe
        595                 600                 605
His Tyr Val Lys Pro Ser Gly Gly Arg Ser His Trp His Gly Asp Tyr
        610                 615                 620
Val Asp Glu Ser Thr Lys Pro Leu Phe Pro Phe Gly His Gly Leu Ser
625                 630                 635                 640
Tyr Thr Lys Phe Glu Tyr Ser Asn Leu Arg Ile Glu Pro Lys Glu Val
                645                 650                 655
Pro Pro Ala Gly Glu Val Ile Lys Val Asp Val Glu Asn Thr Gly
            660                 665                 670
```

-continued

Asp Arg Asp Gly Asp Glu Val Gln Leu Tyr Ile Gly Arg Glu Phe
        675             680             685

Ala Ser Val Thr Arg Pro Val Lys Glu Leu Lys Gly Phe Lys Arg Val
690             695             700

Ser Leu Lys Ala Lys Glu Lys Lys Thr Val Val Phe Arg Leu His Met
705             710             715             720

Asp Val Leu Ala Tyr Tyr Asp Arg Asp Met Lys Leu Val Val Glu Pro
            725             730             735

Gly Glu Phe Lys Val Met Val Gly Ser Ser Glu Asp Ile Arg Leu
            740             745             750

Thr Gly Ser Phe Thr Val Val Gly Glu Lys Arg Glu Val Val Gly Met
        755             760             765

Arg Lys Phe Phe Thr Glu Ala Cys Glu Glu
        770             775

<210> SEQ ID NO 6
<211> LENGTH: 754
<212> TYPE: PRT
<213> ORGANISM: Sulfolobus solfataricus P2

<400> SEQUENCE: 6

Met Thr Ala Ile Lys Ser Leu Leu Asn Gln Met Ser Ile Glu Glu Lys
1               5                   10                  15

Ile Ala Gln Leu Gln Ala Ile Pro Ile Asp Ala Leu Met Glu Gly Lys
            20                  25                  30

Glu Phe Ser Glu Glu Lys Ala Arg Lys Tyr Leu Lys Leu Gly Ile Gly
        35                  40                  45

Gln Ile Thr Arg Val Ala Gly Ser Arg Leu Gly Leu Lys Pro Lys Glu
    50                  55                  60

Val Val Lys Leu Val Asn Lys Val Gln Lys Phe Leu Val Glu Asn Thr
65                  70                  75                  80

Arg Leu Lys Ile Pro Ala Ile Ile His Glu Cys Leu Ser Gly Leu
                85                  90                  95

Met Gly Tyr Ser Ser Thr Ala Phe Pro Gln Ala Ile Gly Leu Ala Ser
            100                 105                 110

Thr Trp Asn Pro Glu Leu Leu Thr Asn Val Ala Ser Thr Ile Arg Ser
        115                 120                 125

Gln Gly Arg Leu Ile Gly Val Asn Gln Cys Leu Ser Pro Val Leu Asp
    130                 135                 140

Val Cys Arg Asp Pro Arg Trp Gly Arg Cys Glu Glu Thr Tyr Gly Glu
145                 150                 155                 160

Asp Pro Tyr Leu Val Ala Ser Met Gly Leu Ala Tyr Ile Thr Gly Leu
                165                 170                 175

Gln Gly Glu Thr Gln Leu Val Ala Thr Ala Lys His Phe Ala Ala His
            180                 185                 190

Gly Phe Pro Glu Gly Gly Arg Asn Ile Ala Gln Val His Val Gly Asn
        195                 200                 205

Arg Glu Leu Arg Glu Thr Phe Leu Phe Pro Phe Glu Val Ala Val Lys
    210                 215                 220

Ile Gly Lys Val Met Ser Ile Met Pro Ala Tyr His Glu Ile Asp Gly
225                 230                 235                 240

Val Pro Cys His Gly Asn Pro Gln Leu Leu Thr Asn Ile Leu Arg Gln
                245                 250                 255

Glu Trp Gly Phe Asp Gly Ile Val Val Ser Asp Tyr Asp Gly Ile Arg
            260                 265                 270

```
Gln Leu Glu Ala Ile His Lys Val Ala Ser Asn Lys Met Glu Ala Ala
        275                 280                 285

Ile Leu Ala Leu Glu Ser Gly Val Asp Ile Glu Phe Pro Thr Ile Asp
290                 295                 300

Cys Tyr Gly Glu Pro Leu Val Thr Ala Ile Lys Glu Gly Leu Val Ser
305                 310                 315                 320

Glu Ala Ile Ile Asp Arg Ala Val Glu Arg Val Leu Arg Ile Lys Glu
                325                 330                 335

Arg Leu Gly Leu Leu Asp Asn Pro Phe Val Asp Glu Ser Ala Val Pro
                340                 345                 350

Glu Arg Leu Asp Asp Arg Lys Ser Arg Glu Leu Ala Leu Lys Ala Ala
            355                 360                 365

Arg Glu Ser Ile Val Leu Leu Lys Asn Glu Asn Asn Met Leu Pro Leu
        370                 375                 380

Ser Lys Asn Ile Asn Lys Ile Ala Val Ile Gly Pro Asn Ala Asn Asp
385                 390                 395                 400

Pro Arg Asn Met Leu Gly Asp Tyr Thr Tyr Thr Gly His Leu Asn Ile
                405                 410                 415

Asp Ser Gly Ile Glu Ile Val Thr Val Leu Gln Gly Ile Ala Lys Lys
                420                 425                 430

Val Gly Glu Gly Lys Val Leu Tyr Ala Lys Gly Cys Asp Ile Ala Gly
            435                 440                 445

Glu Ser Lys Glu Gly Phe Ser Glu Ala Ile Glu Ile Ala Lys Gln Ala
        450                 455                 460

Asp Val Ile Ile Ala Val Met Gly Glu Lys Ser Gly Leu Pro Leu Ser
465                 470                 475                 480

Trp Thr Asp Ile Pro Ser Glu Glu Glu Phe Lys Lys Tyr Gln Ala Val
                485                 490                 495

Thr Gly Glu Gly Asn Asp Arg Ala Ser Leu Arg Leu Leu Gly Val Gln
                500                 505                 510

Glu Glu Leu Leu Lys Glu Leu Tyr Lys Thr Gly Lys Pro Ile Ile Leu
            515                 520                 525

Val Leu Ile Asn Gly Arg Pro Leu Val Leu Ser Pro Ile Ile Asn Tyr
        530                 535                 540

Val Lys Ala Ile Ile Glu Ala Trp Phe Pro Gly Glu Glu Gly Gly Asn
545                 550                 555                 560

Ala Ile Ala Asp Ile Ile Phe Gly Asp Tyr Asn Pro Ser Gly Arg Leu
                565                 570                 575

Pro Ile Thr Phe Pro Met Asp Thr Gly Gln Ile Pro Leu Tyr Tyr Ser
                580                 585                 590

Arg Lys Pro Ser Ser Phe Arg Pro Tyr Val Met Leu His Ser Ser Pro
            595                 600                 605

Leu Phe Thr Phe Gly Tyr Gly Leu Ser Tyr Thr Gln Phe Glu Tyr Ser
        610                 615                 620

Asn Leu Glu Val Thr Pro Lys Glu Val Gly Pro Leu Ser Tyr Ile Thr
625                 630                 635                 640

Ile Leu Leu Asp Val Lys Asn Val Gly Asn Met Glu Gly Asp Glu Val
                645                 650                 655

Val Gln Leu Tyr Ile Ser Lys Ser Phe Ser Ser Val Ala Arg Pro Val
                660                 665                 670

Lys Glu Leu Lys Gly Phe Ala Lys Val His Leu Lys Pro Gly Glu Lys
            675                 680                 685

Arg Arg Val Lys Phe Ala Leu Pro Met Glu Ala Leu Ala Phe Tyr Asp
        690                 695                 700
```

-continued

```
Asn Phe Met Arg Leu Val Val Glu Lys Gly Glu Tyr Gln Ile Leu Ile
705                 710                 715                 720

Gly Asn Ser Ser Glu Asn Ile Ile Leu Lys Asp Thr Phe Arg Ile Lys
                725                 730                 735

Glu Thr Lys Pro Ile Met Glu Arg Arg Ile Phe Leu Ser Asn Val Gln
            740                 745                 750

Ile Glu

<210> SEQ ID NO 7
<211> LENGTH: 765
<212> TYPE: PRT
<213> ORGANISM: Solibacter usitatus Ellin6076

<400> SEQUENCE: 7

Met Pro Arg Pro Ala Lys Ile Glu Pro Tyr Arg Asn Pro Ala Leu Pro
1               5                   10                  15

Pro Ala Lys Arg Ala Lys Asp Leu Leu Ser His Met Thr Leu Glu Glu
                20                  25                  30

Lys Ala Ala Gln Met Met Cys Val Trp Gln Gln Lys Ala Asp Thr Leu
            35                  40                  45

Val Asp Ala Asp Gly Arg Phe Asp Pro Glu Lys Ala Arg Lys Ala Phe
50                  55                  60

Lys Asp Arg Arg Gly Leu Gly Gln Val Gly Arg Pro Ser Asp Ala Gly
65                  70                  75                  80

Lys Gly Gln Asp Ala Arg Gly Met Ala Glu Leu Thr Asn Ala Ile Gln
                85                  90                  95

Lys Phe Phe Ile Glu Asn Ser Arg Leu Gly Ile Pro Val Ile Phe His
            100                 105                 110

Glu Glu Cys Leu His Gly His Ala Ala Ile Gly Gly Thr Ser Phe Pro
        115                 120                 125

Gln Pro Ile Gly Leu Gly Ala Thr Phe Asp Pro Glu Leu Val Glu Ser
    130                 135                 140

Leu Phe Ala Met Thr Ala Ala Glu Ala Arg Ala Arg Gly Thr His Gln
145                 150                 155                 160

Ala Leu Thr Pro Val Val Asp Val Ala Arg Glu Pro Arg Trp Gly Arg
                165                 170                 175

Val Glu Glu Thr Tyr Gly Glu Asp Pro Phe Leu Val Ser Arg Met Gly
            180                 185                 190

Ile Ala Ala Val Arg Gly Phe Gln Gly Asp Ala Thr Phe Arg Asp Lys
        195                 200                 205

Thr Arg Val Ile Ala Thr Leu Lys His Phe Ala Ala His Gly Gln Pro
    210                 215                 220

Glu Ser Gly Thr Asn Cys Ala Pro Val Asn Val Ser Met Arg Val Leu
225                 230                 235                 240

Arg Glu Thr Phe Leu Phe Pro Phe Lys Glu Ala Leu Asp Lys Gly Cys
                245                 250                 255

Ala Ile Ser Val Met Ala Ser Tyr Asn Glu Ile Asp Gly Val Pro Ser
            260                 265                 270

His Ala Ser Arg Trp Leu Leu Arg Asp Val Leu Arg Lys Glu Trp Gly
        275                 280                 285

Phe Lys Gly Phe Val Val Ser Asp Tyr Ala Ile Tyr Glu Leu Ser
    290                 295                 300

Tyr Arg Pro Glu Ser His Gly His Phe Val Ala Lys Asp Lys Arg Glu
305                 310                 315                 320
```

-continued

```
Ala Cys Ala Leu Ala Val Gln Ala Gly Val Asn Ile Glu Leu Pro Glu
            325                 330                 335

Pro Asp Cys Tyr Leu His Leu Val Asp Leu Val His Lys Gly Val Leu
        340                 345                 350

Gln Glu Ser Gln Leu Asp Glu Leu Val Glu Pro Met Leu Arg Trp Lys
    355                 360                 365

Phe Gln Met Gly Leu Phe Asp Asp Pro Tyr Val Asp Pro Ala Glu Ala
370                 375                 380

Glu Arg Ile Ala Gly Cys Asp Ala His Arg Glu Leu Ala Met Gln Ala
385                 390                 395                 400

Ala Arg Glu Thr Ile Thr Leu Leu Lys Asn Asp Gly Pro Val Val Pro
            405                 410                 415

Leu Asp Leu Ser Ala Ile Lys Thr Ile Ala Val Ile Gly Pro Asn Ala
        420                 425                 430

Asn Arg Ser Leu Leu Gly Gly Tyr Ser Gly Val Pro Lys His Asp Val
    435                 440                 445

Thr Val Leu Asp Gly Ile Arg Glu Arg Val Gly Ser Arg Ala Lys Val
450                 455                 460

Val Tyr Ala Glu Gly Cys Lys Ile Thr Ile Gly Gly Ser Trp Val Gln
465                 470                 475                 480

Asp Glu Val Thr Pro Ser Asp Pro Ala Glu Asp Arg Arg Gln Ile Ala
            485                 490                 495

Glu Ala Val Lys Val Ala Lys Arg Ala Asp Val Ile Val Leu Ala Ile
        500                 505                 510

Gly Gly Asn Glu Gln Thr Ser Arg Glu Ala Trp Ser Pro Lys His Leu
    515                 520                 525

Gly Asp Arg Pro Ser Leu Asp Leu Val Gly Arg Gln Glu Glu Leu Val
530                 535                 540

Arg Ala Met Val Ala Thr Gly Lys Pro Val Ile Ala Phe Leu Phe Asn
545                 550                 555                 560

Gly Arg Pro Ile Ser Ile Asn Tyr Leu Ala Gln Ser Val Pro Ala Ile
            565                 570                 575

Phe Glu Cys Trp Tyr Leu Gly Gln Glu Thr Gly Arg Ala Val Ala Glu
        580                 585                 590

Val Leu Phe Gly Asp Thr Asn Pro Gly Gly Lys Leu Pro Ile Thr Ile
    595                 600                 605

Pro Arg Ser Ala Gly His Leu Pro Ala Phe Tyr Asn His Lys Pro Ser
610                 615                 620

Ala Arg Arg Gly Tyr Leu Phe Asp Glu Val Gly Pro Leu Tyr Ala Phe
625                 630                 635                 640

Gly Tyr Gly Leu Ser Tyr Thr Thr Phe Ala Phe Gln Asn Leu Arg Leu
            645                 650                 655

Ala Lys Lys Lys Met His Arg Glu Ser Thr Ala Arg Val Leu Val Asp
        660                 665                 670

Val Thr Asn Thr Gly Ala Arg Glu Gly Arg Glu Val Val Gln Leu Tyr
    675                 680                 685

Ile Arg Asp Leu Val Ser Ser Val Thr Arg Pro Ile Lys Glu Leu Lys
690                 695                 700

Gly Phe Arg Lys Ile Thr Leu Gln Pro Gly Gln Thr Gln Thr Val Glu
705                 710                 715                 720

Phe Glu Ile Thr Pro Asp Leu Leu Ala Phe Tyr Asn Val Asp Met Lys
            725                 730                 735

Phe Val Val Glu Pro Gly Asp Phe Glu Ile Met Val Gly Ser Ser Ser
        740                 745                 750
```

Arg Asp Ala Asp Leu Gln Lys Val Ile Leu Arg Val Glu
        755                 760                 765

<210> SEQ ID NO 8
<211> LENGTH: 2397
<212> TYPE: DNA
<213> ORGANISM: Artificial
<220> FEATURE:
<223> OTHER INFORMATION: Artificial mutant of Alicyclobacillus
      acidocaldarius

<400> SEQUENCE: 8

| | | | | | |
|---|---|---|---|---|---|
| ttgaatataa | aggcggcgtc | agcgcctgat | gagcagagga | ggcttcccgt | gacacccgtg | 60 |
| tatctcgatc | ccgcacagtc | cattgaagcg | cgcgtcgacg | cgctcctggc | cgatatgacg | 120 |
| cttgaagaaa | aggtcgctca | actcacgtcc | atctgggcgt | tcgaagtcct | ggatgagctc | 180 |
| gagttctccg | ccgagaaggc | cgccgccgtg | ctcgggcagg | gcatcggaca | ggtgacccga | 240 |
| attggcggcg | ccaccaatct | ggacccgccg | gatgtggccc | gcctcgccaa | ccagattcag | 300 |
| cgctacctgc | gcgatcacac | gcgcctcggc | attccggcgc | tgatccacga | ggagtcgtgc | 360 |
| agcggctaca | tggccaaggg | cgccacctgc | tttccgcaaa | ccattggcat | cgcgagcacg | 420 |
| tgggatgtcg | atctcgcccg | ccgtattggc | gccatcatcc | gcgatcagat | gcgggccgtc | 480 |
| ggggcgcgcc | aggcgctcgc | cccgctcctg | gatgtgcac | gagatccgcg | ctggggccgg | 540 |
| gtggaggaga | cgttcggcga | agatccgtac | ctcgtggcgc | agatgggcat | cgcgtacgtc | 600 |
| cgcgggctgc | agggagacga | cctgagccag | ggcgtgatgg | cgacgggcaa | gcacttcgtg | 660 |
| ggctacgggg | cgtccgaggg | cggcatgaac | tgggcgccgg | cgcacatccc | ggagcgcgag | 720 |
| ctgcgcgagg | tgtacctgtt | cccgttcgag | gcggcggtgc | gcgaggcggg | gctcggcgcc | 780 |
| atcatgccgg | ggtaccacga | gctcgacggc | gtgccctgcc | acgacaatcc | agggcttttg | 840 |
| cgcgagaccc | tccgcgggcg | ctggggcttt | caggggctcg | tggtgtcgga | ctatttcgcc | 900 |
| gtgaatcagc | tgttcgaata | tcatcaggtg | gcccgggaca | aggcggaggc | cgcggcgctc | 960 |
| gccgtgcgcg | ccggggtgga | cgtggagctg | ccgacgcgcg | acgtgtacgg | caagccgctc | 1020 |
| atcgaggccg | ttgcacgagg | gctcgtcagc | ccggccgaga | tcgacgaact | cgtgcgccgg | 1080 |
| gtgctcacgt | ggaagttccg | gctcggcctc | ttcgatcacc | cgtttgtcga | cgagggcgcg | 1140 |
| gccatcgccg | tcttcgacaa | cgcggagcag | cgtcaggtgg | cgcggggagc | ggcggagaag | 1200 |
| tcgatggtcc | tcctcaaaaa | cgacgggctt | ctgcccctcg | cgccccgcgg | caccatcgcc | 1260 |
| gtgatcggcc | caaacgcgca | cacgacgcgc | aatttggtag | gcgattacgc | ctacccgtgc | 1320 |
| cacatcgagt | cgctcctcga | gcagtccgag | gacaacgtgt | ttcagacccc | gcttccgagc | 1380 |
| ggcgtgaaac | acgtggacga | gttcatcctc | atgcggacca | tcctcgaggc | catccgccat | 1440 |
| cgcgtcgggt | cggaggcgca | ggtcgtctac | gcgaaggggt | gcgacatcct | cggcggtgag | 1500 |
| gatgcggagc | tcgaggaggc | ggtggcgctt | ccgcgcaagg | cggacgtggc | ggttgtggtg | 1560 |
| gtgggcgatc | gcgccgggct | cacggacgcg | tgcacgacag | gggaatcgcg | agacagagcc | 1620 |
| acgctctcgc | tcatcgggcg | gcaggaggaa | ctcgtgcggc | gcgtaatcgc | cacgggcacg | 1680 |
| aagacggtcg | tggtgctcgt | gagcgggcgg | ccgctcgcca | tcccggacat | cgcggagcgg | 1740 |
| gcgaacgccg | ttctcgaggc | gtggctgccg | ggcgaggaag | gcgcggaggc | ggtggccgcg | 1800 |
| gtcctgtttg | gcgacgtgaa | tccgtccggg | aagctgccca | tcacgattcc | gcgcagcgtg | 1860 |
| ggccaggtgc | caatttacta | cgggcacaag | ccgtcgggcg | gccgctcgca | ctggaagggc | 1920 |
| gcgtatgtgg | acgagagcaa | tctgccgctc | tatccgtttg | gcacgggct | gtcctacacg | 1980 |

```
gcgttcgcgt accgggatct ggcgctgtct ccgagcgtcc tgggcgtgca cggcgaggtc    2040
gaggtgtcgt gcgtgatcga aaacgtcggg gctcgcgcgg gcgaagaggt ggtgcaactg    2100
tacgcacgcg acgtggcggc ggacgtgacg cggccggtga aggcgctctg cggctttgcg    2160
cgggtggcgc tcgcgccggg agagaaggcg cgagtgcggt tccgggtttc agcgcaccag    2220
ttcggcttct acaaccggga gatgcggtat gtcgtggagc cgggcgagat cgagttcatg    2280
gtgggggcgt cgtccgagga catccgcctg cgcggggcgg tgcggatgga cggcgcggtg    2340
acggagatcg agcacgagaa ggtataccag agcgcggtgg acgtcgagcg gatgtga       2397
```

<210> SEQ ID NO 9
<211> LENGTH: 2397
<212> TYPE: DNA
<213> ORGANISM: Artificial
<220> FEATURE:
<223> OTHER INFORMATION: Artificial mutant of Alicyclobacillus
      acidocaldarius

<400> SEQUENCE: 9

```
ttgaatctga aggcggcgtc agcgcctgat gagcagagga ggcttcccgt gacacccgtg      60
tatctcgatc ccgcacagtc cattgaagcg cgcgtcgacg cgctcctggc cgatatgacg     120
cttgaagaaa aggtcgctca actcacgtcc atctgggcgt tcgaagtcct ggatgagctc     180
gagttctccg ccgagaaggc cgccgccgtg ctcgggcagg gcatcggaca ggtgacccga     240
attggcggcg ccaccaatct ggacccgccg gatgtggccc gcctcgccaa ccagattcag     300
cgctacctgc gcgatcacac gcgcctcggc attccggcgc tgatccacga ggagtcgtgc     360
agcggctaca tggccaaggg cgccacctgc tttccgcaaa ccattggcat cgcgagcacg     420
tgggatgtcg atctcgcccg ccgtattggc gccatcatcc gcatcagat gcgggccgtc     480 ggggcgcgcc aggcgctcgc cccgctcctg gatgtggcac gagatccgcg ctggggccgg     540
gtggaggaga cgttcggcga agatccgtac ctcgtggcgc agatgggcat cgcgtacgtc     600
cgcgggctgc agggagacga cctgagccag ggcgtgatgg cgacgggcaa gcacttcgtg     660
ggctacgggg cgtccgaggg cggcatgaac tgggcgccgg cgcacatccc ggagcgcgag     720
ctgcgcgagg tgtacctgtt cccgttcgag gcggcggtgc gcgaggcggg gctcggcgcc     780
atcatgccgg ggtaccacga gctcgacggc gtgccctgcc acgacaatcc agggcttttg     840
cgcgagaccc tccgcgggcg ctggggcttt caggggctcg tggtgtcgga ctatttcgcc     900
gtgaatcagc tgttcgaata tcatcaggtg gcccgggaca aggcggaggc cgcggcgctc     960
gccgtgcgcg ccggggtgga cgtggagctg ccgacgcgcg acgtgtacgg caagccgctc    1020
atcgaggccg ttgcacgagg gctcgtcagc ccggccgaga tcgacgaact cgtgcgccgg    1080
gtgctcacgt ggaagttccg gctcggcctc ttcgatcacc cgtttgtcga cgagggcgcg    1140
gccatcgccc tcttcgacaa cgcggagcag cgtcaggtgg cgcgggaggc ggcggagaag    1200
tcgatggtcc tcctcaaaaa cgacgggctt ctgcccctcg cgccccgcgg caccatcgcc    1260
gtgatcggcc caaacgcgca cacgacgcgc aatttggtag gcgattacgc ctacccgtgc    1320
cacatcgagt cgctcctcga gcagtccgag gacaacgtgt ttcagacccc gcttccgagc    1380
ggcgtgaaac acgtggacga gttcatcctc atgcggacca tcctcgaggc catccgccat    1440
cgcgtcgggt cggaggcgca ggtcgtctac gcgaagggt gcgacatcct cggcggtgag    1500
gatgcggagc tcgaggaggc ggtggcgctt ccgcgaagg cggacgtggc ggttgtggtg    1560
gtgggcgatc gcgccgggct cacggacgcg tgcacgacag gggaatcgcg agacagagcc    1620
```

```
acgctctcgc tcatcgggcg gcaggaggaa ctcgtgcggc gcgtaatcgc cacgggcacg    1680
aagacggtcg tggtgctcgt gagcgggcgg ccgctcgcca tcccggacat cgcggagcgg    1740
gcgaacgccg ttctcgaggc gtggctgccg ggcgaggaag gcgcggaggc ggtggccgcg    1800
gtcctgtttg gcgacgtgaa tccgtccggg aagctgccca tcacgattcc gcgcagcgtg    1860
ggccaggtgc caatttacta cgggcacaag ccgtcgggcg gccgctcgca ctggaagggc    1920
gcgtatgtgg acgagagcaa tctgccgctc tatccgtttg gcacgggct gtcctacacg     1980 gcgttcgcgt accgggatct ggcgctgtct ccgagcgtcc tgggcgtgca cggcgaggtc    2040
gaggtgtcgt gcgtgatcga aaacgtcggg gctcgcgcgg gcgaagaggt ggtgcaactg    2100
tacgcacgcg acgtggcggc ggacgtgacg cggccggtga aggcgctctg cggctttgcg    2160
cgggtggcgc tcgcgccggg agagaaggcg cgagtgcggt tccgggtttc agcgcaccag    2220
ttcggcttct acaaccggga gatgcggtat gtcgtggagc cgggcgagat cgagttcatg    2280
gtgggggcgt cgtccgagga catccgcctg cgcggggcgg tgcggatgga cggcgcggtg    2340
acggagatcg agcacgagaa ggtataccag agcgcggtgg acgtcgagcg gatgtga      2397
```

<210> SEQ ID NO 10
<211> LENGTH: 2397
<212> TYPE: DNA
<213> ORGANISM: Artificial
<220> FEATURE:
<223> OTHER INFORMATION: Artificial mutant of Alicyclobacillus
    acidocaldarius

<400> SEQUENCE: 10

```
ttgaatgtga gggcggcgtc agcgcctgat gagcagagga ggcttcccgt gacacccgtg      60
tatctcgatc ccgcacagtc cattgaagcg cgcgtcgacg cgctcctggc cgatatgacg     120
cttgaagaaa aggtcgctca actcacgtcc atctgggcgt tcgaagtcct ggatgagctc     180
gagttctccg ccgagaaggc cgccgccgtg ctcgggcagg gcatcggaca ggtgaccccga    240 attggcggcg ccaccaatct ggacccgccg gatgtggccc gcctcgccaa ccagattcag    300
cgctacctgc gcgatcacac gcgcctcggc attccgcgc tgatccacga ggagtcgtgc     360
agcggctaca tggccaaggg cgccacctgc tttccgcaaa ccattggcat cgcgagcacg    420
tgggatgtcg atctcgcccg ccgtattggc gccatcatcc gcgatcagat gcgggccgtc    480
ggggcgcgcc aggcgctcgc cccgctcctg gatgtggcac gagatccgcg ctggggccgg    540
gtggaggaga cgttcggcga agatccgtac ctcgtggcgc agatgggcat cgcgtacgtc    600
cgcgggctgc agggagacga cctgagccag ggcgtgatgg cgacgggcaa gcacttcgtg    660
ggctacgggg cgtccgaggg cggcatgaac tgggcgccgg cgcacatccc ggagcgcgag    720
ctgcgcgagg tgtacctgtt cccgttcgag gcggcggtgc gcgaggcggg gctcggcgcc    780
atcatgccgg ggtaccacga gctcgacggc gtgccctgcc acgacaatcc agggcttttg    840
cgcgagaccc tccgcgggcg ctgggcgttt caggggctcg tggtgtcgga ctatttcgcc    900
gtgaatcagc tgttcgaata tcatcaggtg gcccgggaca aggcggaggc gcggcgctc     960 gccgtgcgcg ccggggtgga cgtggagctg ccgacgcgcg acgtgtacgg caagccgctc   1020
atcgaggccg ttgcacgagg gctcgtcagc ccggccgaga tcgacgaact cgtgcgccgg   1080
gtgctcacgt ggaagttccg gctcggcctc ttcgatcacc cgtttgtcga cgagggcgcg   1140
gccatcgccg tcttcgacaa cgcggagcag cgtcaggtgg cgcgggaggc ggcggagaag   1200
tcgatggtcc tcctcaaaaa cgacgggctt ctgcccctcg cgccccgcgg caccatcgcc   1260
gtgatcggcc caaacgcgca cacgacgcgc aatttggtag gcgattacgc ctacccgtgc   1320
```

```
cacatcgagt cgctcctcga gcagtccgag acaacgtgt ttcagacccc gcttccgagc   1380
ggcgtgaaac acgtggacga gttcatcctc atgcggacca tcctcgaggc catccgccat   1440
cgcgtcgggt cggaggcgca ggtcgtctac gcgaaggggt gcgacatcct cggcggtgag   1500
gatgcggagc tcgaggaggc ggtggcgctt gccgcgaagg cggacgtggc ggttgtggtg   1560
gtgggcgatc gcgccgggct cacggacgcg tgcacgacag gggaatcgcg agacagagcc   1620
acgctctcgc tcatcgggcg gcaggaggaa ctcgtgcggc gcgtaatcgc cacgggcacg   1680
aagacggtcg tggtgctcgt gagcgggcgg ccgctcgcca tcccggacat cgcggagcgg   1740
gcgaacgccg ttctcgaggc gtggctgccg ggcgaggaag gcgcggaggc ggtggccgcg   1800
gtcctgtttg cgacgtgaa tccgtccggg aagctgccca tcacgattcc gcgcagcgtg   1860
ggccaggtgc caatttacta cgggcacaag ccgtcgggcg gccgctcgca ctggaagggc   1920
gcgtatgtgg acgagagcaa tctgccgctc tatccgtttg gcacgggct gtcctacacg   1980 gcgttcgcgt accgggatct ggcgctgtct ccgagcgtcc tgggcgtgca cggcgaggtc   2040
gaggtgtcgt gcgtgatcga aaacgtcggg gctcgcgcgg gcgaagaggt ggtgcaactg   2100
tacgcacgcg acgtggcggc ggacgtgacg cggccgtga aggcgctctg cggctttgcg   2160
cgggtggcgc tcgcgccggg agagaaggcg cgagtgcggt tccgggtttc agcgcaccag   2220
ttcggcttct acaaccggga gatgcggtat gtcgtggagc cgggcgagat cgagttcatg   2280
gtgggggcgt cgtccgagga catccgcctg cgcggggcgg tgcggatgga cggcgcggtg   2340
acggagatcg agcacgagaa ggtataccag agcgcggtgg acgtcgagcg gatgtga     2397
```

<210> SEQ ID NO 11
<211> LENGTH: 2397
<212> TYPE: DNA
<213> ORGANISM: Artificial
<220> FEATURE:
<223> OTHER INFORMATION: Artificial mutant of Alicyclobacillus
      acidocaldarius

<400> SEQUENCE: 11

```
ttgaatgtga aggcggcgtc agcgcctgag gagcagagga ggcttcccgt gacacccgtg     60
tatctcgatc ccgcacagtc cattgaagcg cgcgtcgacg cgctcctggc cgatatgacg    120
cttgaagaaa aggtcgctca actcacgtcc atctgggcgt tcgaagtcct ggatgagctc    180
gagttctccg ccgagaaggc cgccgccgtg ctcgggcagg gcatcggaca ggtgacccga    240
attggcggcg ccaccaatct ggacccgccg gatgtggccc gctcgccaa ccagattcag    300 cgctacctgc gcgatcacac gcgcctcggc attccggcgc tgatccacga ggagtcgtgc    360
agcggctaca tggccaaggg cgccacctgc tttccgcaaa ccattggcat cgcgagcacg    420
tgggatgtcg atctcgcccg ccgtattggc gccatcatcc gcgatcagat gcgggccgtc    480
ggggcgcgcc aggcgctcgc cccgctcctg gatgtggcac gagatccgcg ctggggccgg    540
gtggaggaga cgttcggcga agatccgtac ctcgtggcgc agatgggcat cgcgtacgtc    600
cgcgggctgc agggagacga cctgagccag ggcgtgatgg cgacgggcaa gcacttcgtg    660
ggctacgggg cgtccgaggg cggcatgaac tgggcgccgg cgcacatccc ggagcgcgag    720
ctgcgcgagg tgtacctgtt cccgttcgag gcggcggtgc gcgaggcggg gctcggcgcc    780
atcatgccgg ggtaccacga gctcgacggc gtgccctgcc acgacaatcc agggcttttg    840
cgcgagaccc tccgcgggcg ctggggcttt caggggctcg tggtgtcgga ctatttcgcc    900
gtgaatcagc tgttcgaata tcatcaggtg gcccgggaca aggcggaggc cgcggcgctc    960
```

```
gccgtgcgcg ccggggtgga cgtggagctg ccgacgcgcg acgtgtacgg caagccgctc    1020
atcgaggccg ttgcacgagg gctcgtcagc ccggccgaga tcgacgaact cgtgcgccgg    1080
gtgctcacgt ggaagttccg gctcggcctc ttcgatcacc cgtttgtcga cgagggcgcg    1140
gccatcgccg tcttcgacaa cgcggagcag cgtcaggtgg cgcgggaggc ggcggagaag    1200
tcgatggtcc tcctcaaaaa cgacgggctt ctgcccctcg cgccccgcgg caccatcgcc    1260
gtgatcggcc caaacgcgca cacgacgcgc aatttggtag gcgattacgc ctacccgtgc    1320
cacatcgagt cgctcctcga gcagtccgag acaacgtgt tcagacccc gcttccgagc    1380 ggcgtgaaac acgtggacga gttcatcctc atgcggacca tcctcgaggc catccgccat    1440
cgcgtcgggt cggaggcgca ggtcgtctac gcgaaggggt gcgacatcct cggcggtgag    1500
gatgcggagc tcgaggaggc ggtggcgctt ccgcgaagg cggacgtggc ggttgtggtg    1560
gtgggcgatc gcgccgggct cacggacgcg tgcacgacag gggaatcgcg agacagagcc    1620
acgctctcgc tcatcgggcg gcaggaggaa ctcgtgcggc gcgtaatcgc cacgggcacg    1680
aagacggtcg tggtgctcgt gagcgggcgg ccgctcgcca tcccggacat cgcggagcgg    1740
gcgaacgccg ttctcgaggc gtggctgccg ggcgaggaag gcgcggaggc ggtggccgcg    1800
gtcctgtttg gcgacgtgaa tccgtccggg aagctgccca tcacgattcc gcgcagcgtg    1860
ggccaggtgc caatttacta cgggcacaag ccgtcgggcg gccgctcgca ctggaagggc    1920
gcgtatgtgg acgagagcaa tctgccgctc tatccgtttg ggcacgggct gtcctacacg    1980
gcgttcgcgt accgggatct ggcgctgtct ccgagcgtcc tgggcgtgca cggcgaggtc    2040
gaggtgtcgt gcgtgatcga aaacgtcggg gctcgcgcgg gcgaagaggt ggtgcaactg    2100
tacgcacgcg acgtggcggc ggacgtgacg cggccggtga aggcgctctg cggctttgcg    2160
cgggtggcgc tcgcgccggg agagaaggcg cgagtgcggt tccgggtttc agcgcaccag    2220
ttcggcttct acaaccggga gatgcggtat gtcgtggagc cgggcgagat cgagttcatg    2280
gtgggggcgt cgtccgagga catccgcctg cgcggggcgg tgcggatgga cggcgcggtg    2340
acggagatcg agcacgagaa ggtataccag agcgcggtgg acgtcgagcg gatgtga      2397
```

<210> SEQ ID NO 12
<211> LENGTH: 2397
<212> TYPE: DNA
<213> ORGANISM: Artificial
<220> FEATURE:
<223> OTHER INFORMATION: Artificial mutant of Alicyclobacillus
      acidocaldarius

<400> SEQUENCE: 12

```
ttgaatgtga aggcggcgtc agcgcctgat gatcagagga ggcttcccgt gacacccgtg      60
tatctcgatc ccgcacagtc cattgaagcg cgcgtcgacg cgctcctggc cgatatgacg     120
cttgaagaaa aggtcgctca actcacgtcc atctgggcgt tcgaagtcct ggatgagctc     180
gagttctccg ccgagaaggc cgccgccgtg ctcgggcagg gcatcggaca ggtgacccga     240
attggcggcg ccaccaatct ggacccgccg gatgtggccc gcctcgccaa ccagattcag     300
cgctacctgc gcgatcacac gcgcctcggc attccgcgc tgatccacga ggagtcgtgc     360
agcggctaca tggccaaggg cgccacctgc tttccgcaaa ccattggcat cgcgagcacg     420
tgggatgtcg atctcgcccg ccgtattggc gccatcatcc gcgatcagat gcgggccgtc     480
ggggcgcgcc aggcgctcgc cccgctcctg gatgtggcac gagatccgcg ctggggccgg     540
gtggaggaga cgttcggcga agatccgtac ctcgtggcgc agatgggcat cgcgtacgtc     600
cgcgggctgc agggagacga cctgagccag ggcgtgatgg cgacgggcaa gcacttcgtg     660
```

-continued

```
ggctacgggg cgtccgaggg cggcatgaac tgggcgccgg cgcacatccc ggagcgcgag    720
ctgcgcgagg tgtacctgtt cccgttcgag gcggcggtgc gcgaggcggg gctcggcgcc    780
atcatgccgg gtaccacga gctcgacggc gtgccctgcc acgacaatcc agggcttttg    840
cgcgagaccc tccgcgggcg ctggggcttt caggggctcg tggtgtcgga ctatttcgcc    900
gtgaatcagc tgttcgaata tcatcaggtg gcccgggaca aggcggaggc cgcggcgctc    960
gccgtgcgcg ccggggtgga cgtggagctg ccgacgcgcg acgtgtacgg caagccgctc    1020
atcgaggccg ttgcacgagg gctcgtcagc ccggccgaga tcgacgaact cgtgcgccgg    1080
gtgctcacgt ggaagttccg gctcggcctc ttcgatcacc cgtttgtcga cgagggcgcg    1140
gccatcgccg tcttcgacaa cgcggagcag cgtcaggtgg cgcggaggc ggcggagaag    1200 tcgatggtcc tcctcaaaaa cgacgggctt ctgcccctcg cgccccgcgg caccatcgcc    1260
gtgatcggcc caaacgcgca cacgacgcgc aatttggtag gcgattacgc ctacccgtgc    1320
cacatcgagt cgctcctcga gcagtccgag gacaacgtgt ttcagacccc gcttccgagc    1380
ggcgtgaaac acgtggacga gttcatcctc atgcggacca tcctcgaggc catccgccat    1440
cgcgtcgggt cggaggcgca ggtcgtctac gcgaaggggt gcgacatcct cggcggtgag    1500
gatgcggagc tcgaggaggc ggtggcgctt gccgcgaagg cggacgtggc ggttgtggtg    1560
gtgggcgatc gcgccgggct cacggacgcg tgcacgacag gggaatcgcg agacagagcc    1620
acgctctcgc tcatcgggcg gcaggaggaa ctcgtgcggc gcgtaatcgc cacgggcacg    1680
aagacggtcg tggtgctcgt gagcgggcgg ccgctcgcca tcccggacat cgcggagcgg    1740
gcgaacgccg ttctcgaggc gtggctgccg ggcgaggaag gcgcggaggc ggtggccgcg    1800
gtcctgtttg gcgacgtgaa tccgtccggg aagctgccca tcacgattcc gcgcagcgtg    1860
ggccaggtgc caatttacta cgggcacaag ccgtcgggcg gccgctcgca ctggaagggc    1920
gcgtatgtgg acgagagcaa tctgccgctc tatccgtttg gcacgggct gtcctacacg    1980 gcgttcgcgt accgggatct ggcgctgtct ccgagcgtcc tgggcgtgca cggcgaggtc    2040
gaggtgtcgt gcgtgatcga aaacgtcggg gctcgcgcgg gcgaagaggt ggtgcaactg    2100
tacgcacgcg acgtggcggc ggacgtgacg cggccggtga aggcgctctg cggctttgcg    2160
cgggtggcgc tcgcgccggg agagaaggcg cgagtgcggt tccgggttc agcgcaccag    2220 ttcggcttct acaaccggga gatgcggtat gtcgtggagc cgggcgagat cgagttcatg    2280 gtggggcgt cgtccgagga catccgcctg cgcggggcgg tgcggatgga cggcgcggtg    2340
acggagatcg agcacgagaa ggtataccag agcgcggtgg acgtcgagcg gatgtga      2397
```

<210> SEQ ID NO 13
<211> LENGTH: 798
<212> TYPE: PRT
<213> ORGANISM: Artificial
<220> FEATURE:
<223> OTHER INFORMATION: Artificial mutant of Alicyclobacillus
    acidocaldarius

<400> SEQUENCE: 13

```
Met Asn Ile Lys Ala Ala Ser Ala Pro Asp Glu Gln Arg Arg Leu Pro
1               5                   10                  15

Val Thr Pro Val Tyr Leu Asp Pro Ala Gln Ser Ile Glu Ala Arg Val
            20                  25                  30

Asp Ala Leu Leu Ala Asp Met Thr Leu Glu Glu Lys Val Ala Gln Leu
        35                  40                  45

Thr Ser Ile Trp Ala Phe Glu Val Leu Asp Glu Leu Glu Phe Ser Ala
```

-continued

```
            50                  55                  60
Glu Lys Ala Ala Val Leu Gly Gln Gly Ile Gly Gln Val Thr Arg
65                  70                  75                  80

Ile Gly Gly Ala Thr Asn Leu Asp Pro Pro Asp Val Ala Arg Leu Ala
                85                  90                  95

Asn Gln Ile Gln Arg Tyr Leu Arg Asp His Thr Arg Leu Gly Ile Pro
                100                 105                 110

Ala Leu Ile His Glu Glu Ser Cys Ser Gly Tyr Met Ala Lys Gly Ala
                115                 120                 125

Thr Cys Phe Pro Gln Thr Ile Gly Ile Ala Ser Thr Trp Asp Val Asp
130                 135                 140

Leu Ala Arg Arg Ile Gly Ala Ile Ile Arg Asp Gln Met Arg Ala Val
145                 150                 155                 160

Gly Ala Arg Gln Ala Leu Ala Pro Leu Leu Asp Val Ala Arg Asp Pro
                165                 170                 175

Arg Trp Gly Arg Val Glu Glu Thr Phe Gly Glu Asp Pro Tyr Leu Val
                180                 185                 190

Ala Gln Met Gly Ile Ala Tyr Val Arg Gly Leu Gln Gly Asp Asp Leu
                195                 200                 205

Ser Gln Gly Val Met Ala Thr Gly Lys His Phe Val Gly Tyr Gly Ala
210                 215                 220

Ser Glu Gly Gly Met Asn Trp Ala Pro Ala His Ile Pro Glu Arg Glu
225                 230                 235                 240

Leu Arg Glu Val Tyr Leu Phe Pro Phe Glu Ala Ala Val Arg Glu Ala
                245                 250                 255

Gly Leu Gly Ala Ile Met Pro Gly Tyr His Glu Leu Asp Gly Val Pro
                260                 265                 270

Cys His Asp Asn Pro Gly Leu Leu Arg Glu Thr Leu Arg Gly Arg Trp
                275                 280                 285

Gly Phe Gln Gly Leu Val Val Ser Asp Tyr Phe Ala Val Asn Gln Leu
                290                 295                 300

Phe Glu Tyr His Gln Val Ala Arg Asp Lys Ala Glu Ala Ala Ala Leu
305                 310                 315                 320

Ala Val Arg Ala Gly Val Asp Val Glu Leu Pro Thr Arg Asp Val Tyr
                325                 330                 335

Gly Lys Pro Leu Ile Glu Ala Val Ala Arg Gly Leu Val Ser Pro Ala
                340                 345                 350

Glu Ile Asp Glu Leu Val Arg Arg Val Leu Thr Trp Lys Phe Arg Leu
                355                 360                 365

Gly Leu Phe Asp His Pro Phe Val Asp Glu Gly Ala Ala Ile Ala Val
                370                 375                 380

Phe Asp Asn Ala Glu Gln Arg Gln Val Ala Arg Glu Ala Ala Glu Lys
385                 390                 395                 400

Ser Met Val Leu Leu Lys Asn Asp Gly Leu Leu Pro Leu Ala Pro Arg
                405                 410                 415

Gly Thr Ile Ala Val Ile Gly Pro Asn Ala His Thr Thr Arg Asn Leu
                420                 425                 430

Val Gly Asp Tyr Ala Tyr Pro Cys His Ile Glu Ser Leu Leu Glu Gln
                435                 440                 445

Ser Glu Asp Asn Val Phe Gln Thr Pro Leu Pro Ser Gly Val Lys His
                450                 455                 460

Val Asp Glu Phe Ile Leu Met Arg Thr Ile Leu Glu Ala Ile Arg His
465                 470                 475                 480
```

```
Arg Val Gly Ser Glu Ala Gln Val Val Tyr Ala Lys Gly Cys Asp Ile
                485                 490                 495

Leu Gly Gly Glu Asp Ala Glu Leu Glu Ala Val Ala Leu Ala Ala
        500                 505                 510

Lys Ala Asp Val Ala Val Val Val Gly Asp Arg Ala Gly Leu Thr
    515                 520                 525

Asp Ala Cys Thr Thr Gly Glu Ser Arg Asp Arg Ala Thr Leu Ser Leu
    530                 535                 540

Ile Gly Arg Gln Glu Glu Leu Val Arg Val Ile Ala Thr Gly Thr
545                 550                 555                 560

Lys Thr Val Val Val Leu Val Ser Gly Arg Pro Leu Ala Ile Pro Asp
                565                 570                 575

Ile Ala Glu Arg Ala Asn Ala Val Leu Glu Ala Trp Leu Pro Gly Glu
                580                 585                 590

Glu Gly Ala Glu Ala Val Ala Ala Val Leu Phe Gly Asp Val Asn Pro
            595                 600                 605

Ser Gly Lys Leu Pro Ile Thr Ile Pro Arg Ser Val Gly Gln Val Pro
    610                 615                 620

Ile Tyr Tyr Gly His Lys Pro Ser Gly Gly Arg Ser His Trp Lys Gly
625                 630                 635                 640

Ala Tyr Val Asp Glu Ser Asn Leu Pro Leu Tyr Pro Phe Gly His Gly
                645                 650                 655

Leu Ser Tyr Thr Ala Phe Ala Tyr Arg Asp Leu Ala Leu Ser Pro Ser
            660                 665                 670

Val Leu Gly Val His Gly Glu Val Glu Val Ser Cys Val Ile Glu Asn
    675                 680                 685

Val Gly Ala Arg Ala Gly Glu Glu Val Val Gln Leu Tyr Ala Arg Asp
    690                 695                 700

Val Ala Ala Asp Val Thr Arg Pro Val Lys Ala Leu Cys Gly Phe Ala
705                 710                 715                 720

Arg Val Ala Leu Ala Pro Gly Glu Lys Ala Arg Val Arg Phe Arg Val
                725                 730                 735

Ser Ala His Gln Phe Gly Phe Tyr Asn Arg Glu Met Arg Tyr Val Val
            740                 745                 750

Glu Pro Gly Glu Ile Glu Phe Met Val Gly Ala Ser Ser Glu Asp Ile
        755                 760                 765

Arg Leu Arg Gly Ala Val Arg Met Asp Gly Ala Val Thr Glu Ile Glu
    770                 775                 780

His Glu Lys Val Tyr Gln Ser Ala Val Asp Val Glu Arg Met
785                 790                 795

<210> SEQ ID NO 14
<211> LENGTH: 798
<212> TYPE: PRT
<213> ORGANISM: Artificial
<220> FEATURE:
<223> OTHER INFORMATION: Artificial mutant of Alicyclobacillus
      acidocaldarius

<400> SEQUENCE: 14

Met Asn Leu Lys Ala Ala Ser Ala Pro Asp Glu Gln Arg Arg Leu Pro
1               5                   10                  15

Val Thr Pro Val Tyr Leu Asp Pro Ala Gln Ser Ile Glu Ala Arg Val
                20                  25                  30

Asp Ala Leu Leu Ala Asp Met Thr Leu Glu Glu Lys Val Ala Gln Leu
            35                  40                  45
```

```
Thr Ser Ile Trp Ala Phe Glu Val Leu Asp Glu Leu Glu Phe Ser Ala
 50              55                  60
Glu Lys Ala Ala Ala Val Leu Gly Gln Gly Ile Gly Gln Val Thr Arg
 65                  70                  75                  80
Ile Gly Gly Ala Thr Asn Leu Asp Pro Pro Asp Val Ala Arg Leu Ala
                 85                  90                  95
Asn Gln Ile Gln Arg Tyr Leu Arg Asp His Thr Arg Leu Gly Ile Pro
             100                 105                 110
Ala Leu Ile His Glu Glu Ser Cys Ser Gly Tyr Met Ala Lys Gly Ala
             115                 120                 125
Thr Cys Phe Pro Gln Thr Ile Gly Ile Ala Ser Thr Trp Asp Val Asp
 130                 135                 140
Leu Ala Arg Arg Ile Gly Ala Ile Ile Arg Asp Gln Met Arg Ala Val
145                 150                 155                 160
Gly Ala Arg Gln Ala Leu Ala Pro Leu Leu Asp Val Ala Arg Asp Pro
                 165                 170                 175
Arg Trp Gly Arg Val Glu Glu Thr Phe Gly Glu Asp Pro Tyr Leu Val
             180                 185                 190
Ala Gln Met Gly Ile Ala Tyr Val Arg Gly Leu Gln Gly Asp Asp Leu
             195                 200                 205
Ser Gln Gly Val Met Ala Thr Gly Lys His Phe Val Gly Tyr Gly Ala
 210                 215                 220
Ser Glu Gly Gly Met Asn Trp Ala Pro Ala His Ile Pro Glu Arg Glu
225                 230                 235                 240
Leu Arg Glu Val Tyr Leu Phe Pro Phe Glu Ala Ala Val Arg Glu Ala
                 245                 250                 255
Gly Leu Gly Ala Ile Met Pro Gly Tyr His Glu Leu Asp Gly Val Pro
             260                 265                 270
Cys His Asp Asn Pro Gly Leu Leu Arg Glu Thr Leu Arg Gly Arg Trp
             275                 280                 285
Gly Phe Gln Gly Leu Val Val Ser Asp Tyr Phe Ala Val Asn Gln Leu
 290                 295                 300
Phe Glu Tyr His Gln Val Ala Arg Asp Lys Ala Glu Ala Ala Ala Leu
305                 310                 315                 320
Ala Val Arg Ala Gly Val Asp Val Glu Leu Pro Thr Arg Asp Val Tyr
                 325                 330                 335
Gly Lys Pro Leu Ile Glu Ala Val Ala Arg Gly Leu Val Ser Pro Ala
             340                 345                 350
Glu Ile Asp Glu Leu Val Arg Arg Val Leu Thr Trp Lys Phe Arg Leu
             355                 360                 365
Gly Leu Phe Asp His Pro Phe Val Asp Glu Gly Ala Ala Ile Ala Val
 370                 375                 380
Phe Asp Asn Ala Glu Gln Arg Gln Val Ala Arg Glu Ala Ala Glu Lys
385                 390                 395                 400
Ser Met Val Leu Leu Lys Asn Asp Gly Leu Leu Pro Leu Ala Pro Arg
                 405                 410                 415
Gly Thr Ile Ala Val Ile Gly Pro Asn Ala His Thr Thr Arg Asn Leu
             420                 425                 430
Val Gly Asp Tyr Ala Tyr Pro Cys His Ile Glu Ser Leu Leu Glu Gln
             435                 440                 445
Ser Glu Asp Asn Val Phe Gln Thr Pro Leu Pro Ser Gly Val Lys His
 450                 455                 460
Val Asp Glu Phe Ile Leu Met Arg Thr Ile Leu Glu Ala Ile Arg His
465                 470                 475                 480
```

```
Arg Val Gly Ser Glu Ala Gln Val Val Tyr Ala Lys Gly Cys Asp Ile
            485                 490                 495
Leu Gly Gly Glu Asp Ala Glu Leu Glu Glu Ala Val Ala Leu Ala Ala
            500                 505                 510
Lys Ala Asp Val Ala Val Val Val Gly Asp Arg Ala Gly Leu Thr
            515                 520                 525
Asp Ala Cys Thr Thr Gly Glu Ser Arg Asp Arg Ala Thr Leu Ser Leu
            530                 535                 540
Ile Gly Arg Gln Glu Glu Leu Val Arg Val Ile Ala Thr Gly Thr
545                 550                 555                 560
Lys Thr Val Val Val Leu Val Ser Gly Arg Pro Leu Ala Ile Pro Asp
                565                 570                 575
Ile Ala Glu Arg Ala Asn Ala Val Leu Glu Ala Trp Leu Pro Gly Glu
                580                 585                 590
Glu Gly Ala Glu Ala Val Ala Ala Val Leu Phe Gly Asp Val Asn Pro
            595                 600                 605
Ser Gly Lys Leu Pro Ile Thr Ile Pro Arg Ser Val Gly Gln Val Pro
            610                 615                 620
Ile Tyr Tyr Gly His Lys Pro Ser Gly Gly Arg Ser His Trp Lys Gly
625                 630                 635                 640
Ala Tyr Val Asp Glu Ser Asn Leu Pro Leu Tyr Pro Phe Gly His Gly
                645                 650                 655
Leu Ser Tyr Thr Ala Phe Ala Tyr Arg Asp Leu Ala Leu Ser Pro Ser
                660                 665                 670
Val Leu Gly Val His Gly Glu Val Glu Val Ser Cys Val Ile Glu Asn
            675                 680                 685
Val Gly Ala Arg Ala Gly Glu Glu Val Val Gln Leu Tyr Ala Arg Asp
            690                 695                 700
Val Ala Ala Asp Val Thr Arg Pro Val Lys Ala Leu Cys Gly Phe Ala
705                 710                 715                 720
Arg Val Ala Leu Ala Pro Gly Glu Lys Ala Arg Val Arg Phe Arg Val
                725                 730                 735
Ser Ala His Gln Phe Gly Phe Tyr Asn Arg Glu Met Arg Tyr Val Val
                740                 745                 750
Glu Pro Gly Glu Ile Glu Phe Met Val Gly Ala Ser Ser Glu Asp Ile
            755                 760                 765
Arg Leu Arg Gly Ala Val Arg Met Asp Gly Ala Val Thr Glu Ile Glu
            770                 775                 780
His Glu Lys Val Tyr Gln Ser Ala Val Asp Val Glu Arg Met
785                 790                 795

<210> SEQ ID NO 15
<211> LENGTH: 798
<212> TYPE: PRT
<213> ORGANISM: Artificial
<220> FEATURE:
<223> OTHER INFORMATION: Artificial mutant of Alicyclobacillus
      acidocaldarius

<400> SEQUENCE: 15

Met Asn Val Arg Ala Ala Ser Ala Pro Asp Glu Gln Arg Arg Leu Pro
1               5                   10                  15
Val Thr Pro Val Tyr Leu Asp Pro Ala Gln Ser Ile Glu Ala Arg Val
            20                  25                  30
Asp Ala Leu Leu Ala Asp Met Thr Leu Glu Glu Lys Val Ala Gln Leu
            35                  40                  45
```

-continued

Thr Ser Ile Trp Ala Phe Glu Val Leu Asp Glu Leu Glu Phe Ser Ala
50              55                  60

Glu Lys Ala Ala Ala Val Leu Gly Gln Gly Ile Gly Gln Val Thr Arg
65              70                  75                  80

Ile Gly Gly Ala Thr Asn Leu Asp Pro Pro Asp Val Ala Arg Leu Ala
            85                  90                  95

Asn Gln Ile Gln Arg Tyr Leu Arg Asp His Thr Arg Leu Gly Ile Pro
        100                 105                 110

Ala Leu Ile His Glu Glu Ser Cys Ser Gly Tyr Met Ala Lys Gly Ala
        115                 120                 125

Thr Cys Phe Pro Gln Thr Ile Gly Ile Ala Ser Thr Trp Asp Val Asp
130                 135                 140

Leu Ala Arg Arg Ile Gly Ala Ile Ile Arg Asp Gln Met Arg Ala Val
145                 150                 155                 160

Gly Ala Arg Gln Ala Leu Ala Pro Leu Leu Asp Val Ala Arg Asp Pro
                165                 170                 175

Arg Trp Gly Arg Val Glu Glu Thr Phe Gly Glu Asp Pro Tyr Leu Val
                180                 185                 190

Ala Gln Met Gly Ile Ala Tyr Val Arg Gly Leu Gln Gly Asp Asp Leu
            195                 200                 205

Ser Gln Gly Val Met Ala Thr Gly Lys His Phe Val Gly Tyr Gly Ala
210                 215                 220

Ser Glu Gly Gly Met Asn Trp Ala Pro Ala His Ile Pro Glu Arg Glu
225                 230                 235                 240

Leu Arg Glu Val Tyr Leu Phe Pro Phe Glu Ala Ala Val Arg Glu Ala
                245                 250                 255

Gly Leu Gly Ala Ile Met Pro Gly Tyr His Glu Leu Asp Gly Val Pro
                260                 265                 270

Cys His Asp Asn Pro Gly Leu Leu Arg Glu Thr Leu Arg Gly Arg Trp
        275                 280                 285

Gly Phe Gln Gly Leu Val Val Ser Asp Tyr Phe Ala Val Asn Gln Leu
290                 295                 300

Phe Glu Tyr His Gln Val Ala Arg Asp Lys Ala Glu Ala Ala Ala Leu
305                 310                 315                 320

Ala Val Arg Ala Gly Val Asp Val Glu Leu Pro Thr Arg Asp Val Tyr
                325                 330                 335

Gly Lys Pro Leu Ile Glu Ala Val Ala Arg Gly Leu Val Ser Pro Ala
            340                 345                 350

Glu Ile Asp Glu Leu Val Arg Arg Val Leu Thr Trp Lys Phe Arg Leu
        355                 360                 365

Gly Leu Phe Asp His Pro Phe Val Asp Glu Gly Ala Ala Ile Ala Val
        370                 375                 380

Phe Asp Asn Ala Glu Gln Arg Gln Val Ala Arg Glu Ala Ala Glu Lys
385                 390                 395                 400

Ser Met Val Leu Leu Lys Asn Asp Gly Leu Leu Pro Leu Ala Pro Arg
                405                 410                 415

Gly Thr Ile Ala Val Ile Gly Pro Asn Ala His Thr Thr Arg Asn Leu
            420                 425                 430

Val Gly Asp Tyr Ala Tyr Pro Cys His Ile Glu Ser Leu Leu Glu Gln
        435                 440                 445

Ser Glu Asp Asn Val Phe Gln Thr Pro Leu Pro Ser Gly Val Lys His
450                 455                 460

Val Asp Glu Phe Ile Leu Met Arg Thr Ile Leu Glu Ala Ile Arg His

```
                465                 470                 475                 480
Arg Val Gly Ser Glu Ala Gln Val Val Tyr Ala Lys Gly Cys Asp Ile
                    485                 490                 495
Leu Gly Gly Glu Asp Ala Glu Leu Glu Glu Ala Val Ala Leu Ala Ala
                500                 505                 510
Lys Ala Asp Val Ala Val Val Val Gly Asp Arg Ala Gly Leu Thr
            515                 520                 525
Asp Ala Cys Thr Thr Gly Glu Ser Arg Asp Arg Ala Thr Leu Ser Leu
            530                 535                 540
Ile Gly Arg Gln Glu Glu Leu Val Arg Val Ile Ala Thr Gly Thr
545                 550                 555                 560
Lys Thr Val Val Val Leu Val Ser Gly Arg Pro Leu Ala Ile Pro Asp
                565                 570                 575
Ile Ala Glu Arg Ala Asn Ala Val Leu Glu Ala Trp Leu Pro Gly Glu
                580                 585                 590
Glu Gly Ala Glu Ala Val Ala Ala Val Leu Phe Gly Asp Val Asn Pro
                595                 600                 605
Ser Gly Lys Leu Pro Ile Thr Ile Pro Arg Ser Val Gly Gln Val Pro
            610                 615                 620
Ile Tyr Tyr Gly His Lys Pro Ser Gly Gly Arg Ser His Trp Lys Gly
625                 630                 635                 640
Ala Tyr Val Asp Glu Ser Asn Leu Pro Leu Tyr Pro Phe Gly His Gly
                    645                 650                 655
Leu Ser Tyr Thr Ala Phe Ala Tyr Arg Asp Leu Ala Leu Ser Pro Ser
                660                 665                 670
Val Leu Gly Val His Gly Glu Val Glu Val Ser Cys Val Ile Glu Asn
                675                 680                 685
Val Gly Ala Arg Ala Gly Glu Glu Val Val Gln Leu Tyr Ala Arg Asp
            690                 695                 700
Val Ala Ala Asp Val Thr Arg Pro Val Lys Ala Leu Cys Gly Phe Ala
705                 710                 715                 720
Arg Val Ala Leu Ala Pro Gly Glu Lys Ala Arg Val Arg Phe Arg Val
                    725                 730                 735
Ser Ala His Gln Phe Gly Phe Tyr Asn Arg Glu Met Arg Tyr Val Val
                740                 745                 750
Glu Pro Gly Glu Ile Glu Phe Met Val Gly Ala Ser Ser Glu Asp Ile
                755                 760                 765
Arg Leu Arg Gly Ala Val Arg Met Asp Gly Ala Val Thr Glu Ile Glu
            770                 775                 780
His Glu Lys Val Tyr Gln Ser Ala Val Asp Val Glu Arg Met
785                 790                 795

<210> SEQ ID NO 16
<211> LENGTH: 798
<212> TYPE: PRT
<213> ORGANISM: Artificial
<220> FEATURE:
<223> OTHER INFORMATION: Artificial mutant of Alicyclobacillus
      acidocaldarius

<400> SEQUENCE: 16

Met Asn Val Lys Ala Ala Ser Ala Pro Glu Glu Gln Arg Arg Leu Pro
1               5                   10                  15

Val Thr Pro Val Tyr Leu Asp Pro Ala Gln Ser Ile Glu Ala Arg Val
                20                  25                  30

Asp Ala Leu Leu Ala Asp Met Thr Leu Glu Glu Lys Val Ala Gln Leu
```

```
                    35                  40                  45
Thr Ser Ile Trp Ala Phe Glu Val Leu Asp Glu Leu Glu Phe Ser Ala
             50                  55                  60
Glu Lys Ala Ala Ala Val Leu Gly Gln Gly Ile Gly Gln Val Thr Arg
 65                  70                  75                  80
Ile Gly Gly Ala Thr Asn Leu Asp Pro Pro Asp Val Ala Arg Leu Ala
                 85                  90                  95
Asn Gln Ile Gln Arg Tyr Leu Arg Asp His Thr Arg Leu Gly Ile Pro
                100                 105                 110
Ala Leu Ile His Glu Glu Ser Cys Ser Gly Tyr Met Ala Lys Gly Ala
                115                 120                 125
Thr Cys Phe Pro Gln Thr Ile Gly Ile Ala Ser Thr Trp Asp Val Asp
            130                 135                 140
Leu Ala Arg Arg Ile Gly Ala Ile Ile Arg Asp Gln Met Arg Ala Val
145                 150                 155                 160
Gly Ala Arg Gln Ala Leu Ala Pro Leu Leu Asp Val Ala Arg Asp Pro
                165                 170                 175
Arg Trp Gly Arg Val Glu Glu Thr Phe Gly Glu Asp Pro Tyr Leu Val
            180                 185                 190
Ala Gln Met Gly Ile Ala Tyr Val Arg Gly Leu Gln Gly Asp Asp Leu
            195                 200                 205
Ser Gln Gly Val Met Ala Thr Gly Lys His Phe Val Gly Tyr Gly Ala
            210                 215                 220
Ser Glu Gly Gly Met Asn Trp Ala Pro Ala His Ile Pro Glu Arg Glu
225                 230                 235                 240
Leu Arg Glu Val Tyr Leu Phe Pro Phe Glu Ala Ala Val Arg Glu Ala
                245                 250                 255
Gly Leu Gly Ala Ile Met Pro Gly Tyr His Glu Leu Asp Gly Val Pro
            260                 265                 270
Cys His Asp Asn Pro Gly Leu Leu Arg Glu Thr Leu Arg Gly Arg Trp
            275                 280                 285
Gly Phe Gln Gly Leu Val Val Ser Asp Tyr Phe Ala Val Asn Gln Leu
        290                 295                 300
Phe Glu Tyr His Gln Val Ala Arg Asp Lys Ala Glu Ala Ala Ala Leu
305                 310                 315                 320
Ala Val Arg Ala Gly Val Asp Val Glu Leu Pro Thr Arg Asp Val Tyr
                325                 330                 335
Gly Lys Pro Leu Ile Glu Ala Val Ala Arg Gly Leu Val Ser Pro Ala
            340                 345                 350
Glu Ile Asp Glu Leu Val Arg Arg Val Leu Thr Trp Lys Phe Arg Leu
            355                 360                 365
Gly Leu Phe Asp His Pro Phe Val Asp Glu Gly Ala Ala Ile Ala Val
        370                 375                 380
Phe Asp Asn Ala Glu Gln Arg Gln Val Ala Arg Glu Ala Ala Glu Lys
385                 390                 395                 400
Ser Met Val Leu Leu Lys Asn Asp Gly Leu Leu Pro Leu Ala Pro Arg
                405                 410                 415
Gly Thr Ile Ala Val Ile Gly Pro Asn Ala His Thr Thr Arg Asn Leu
            420                 425                 430
Val Gly Asp Tyr Ala Tyr Pro Cys His Ile Glu Ser Leu Leu Glu Gln
            435                 440                 445
Ser Glu Asp Asn Val Phe Gln Thr Pro Leu Pro Ser Gly Val Lys His
450                 455                 460
```

```
Val Asp Glu Phe Ile Leu Met Arg Thr Ile Leu Glu Ala Ile Arg His
465                 470                 475                 480

Arg Val Gly Ser Glu Ala Gln Val Val Tyr Ala Lys Gly Cys Asp Ile
            485                 490                 495

Leu Gly Gly Glu Asp Ala Glu Leu Glu Glu Ala Val Ala Leu Ala Ala
            500                 505                 510

Lys Ala Asp Val Ala Val Val Val Gly Asp Arg Ala Gly Leu Thr
515                 520                 525

Asp Ala Cys Thr Thr Gly Glu Ser Arg Asp Arg Ala Thr Leu Ser Leu
530                 535                 540

Ile Gly Arg Gln Glu Glu Leu Val Arg Arg Val Ile Ala Thr Gly Thr
545                 550                 555                 560

Lys Thr Val Val Val Leu Val Ser Gly Arg Pro Leu Ala Ile Pro Asp
                565                 570                 575

Ile Ala Glu Arg Ala Asn Ala Val Leu Glu Ala Trp Leu Pro Gly Glu
            580                 585                 590

Glu Gly Ala Glu Ala Val Ala Ala Val Leu Phe Gly Asp Val Asn Pro
            595                 600                 605

Ser Gly Lys Leu Pro Ile Thr Ile Pro Arg Ser Val Gly Gln Val Pro
610                 615                 620

Ile Tyr Tyr Gly His Lys Pro Ser Gly Gly Arg Ser His Trp Lys Gly
625                 630                 635                 640

Ala Tyr Val Asp Glu Ser Asn Leu Pro Leu Tyr Pro Phe Gly His Gly
                645                 650                 655

Leu Ser Tyr Thr Ala Phe Ala Tyr Arg Asp Leu Ala Leu Ser Pro Ser
            660                 665                 670

Val Leu Gly Val His Gly Glu Val Glu Val Ser Cys Val Ile Glu Asn
            675                 680                 685

Val Gly Ala Arg Ala Gly Glu Glu Val Val Gln Leu Tyr Ala Arg Asp
690                 695                 700

Val Ala Ala Asp Val Thr Arg Pro Val Lys Ala Leu Cys Gly Phe Ala
705                 710                 715                 720

Arg Val Ala Leu Ala Pro Gly Glu Lys Ala Arg Val Arg Phe Arg Val
                725                 730                 735

Ser Ala His Gln Phe Gly Phe Tyr Asn Arg Glu Met Arg Tyr Val Val
            740                 745                 750

Glu Pro Gly Glu Ile Glu Phe Met Val Gly Ala Ser Ser Glu Asp Ile
            755                 760                 765

Arg Leu Arg Gly Ala Val Arg Met Asp Gly Ala Val Thr Glu Ile Glu
770                 775                 780

His Glu Lys Val Tyr Gln Ser Ala Val Asp Val Glu Arg Met
785                 790                 795

<210> SEQ ID NO 17
<211> LENGTH: 798
<212> TYPE: PRT
<213> ORGANISM: Artificial
<220> FEATURE:
<223> OTHER INFORMATION: Artificial mutant of Alicyclobacillus
      acidocaldarius

<400> SEQUENCE: 17

Met Asn Val Lys Ala Ala Ser Ala Pro Asp Asp Gln Arg Arg Leu Pro
1               5                   10                  15

Val Thr Pro Val Tyr Leu Asp Pro Ala Gln Ser Ile Glu Ala Arg Val
            20                  25                  30
```

```
Asp Ala Leu Leu Ala Asp Met Thr Leu Glu Glu Lys Val Ala Gln Leu
             35                  40                  45

Thr Ser Ile Trp Ala Phe Glu Val Leu Asp Glu Leu Glu Phe Ser Ala
 50                  55                  60

Glu Lys Ala Ala Ala Val Leu Gly Gln Gly Ile Gly Gln Val Thr Arg
 65                  70                  75                  80

Ile Gly Gly Ala Thr Asn Leu Asp Pro Pro Asp Val Ala Arg Leu Ala
                 85                  90                  95

Asn Gln Ile Gln Arg Tyr Leu Arg Asp His Thr Arg Leu Gly Ile Pro
                100                 105                 110

Ala Leu Ile His Glu Glu Ser Cys Ser Gly Tyr Met Ala Lys Gly Ala
            115                 120                 125

Thr Cys Phe Pro Gln Thr Ile Gly Ile Ala Ser Thr Trp Asp Val Asp
130                 135                 140

Leu Ala Arg Arg Ile Gly Ala Ile Ile Arg Asp Gln Met Arg Ala Val
145                 150                 155                 160

Gly Ala Arg Gln Ala Leu Ala Pro Leu Leu Asp Val Ala Arg Asp Pro
                165                 170                 175

Arg Trp Gly Arg Val Glu Glu Thr Phe Gly Glu Asp Pro Tyr Leu Val
                180                 185                 190

Ala Gln Met Gly Ile Ala Tyr Val Arg Gly Leu Gln Gly Asp Asp Leu
            195                 200                 205

Ser Gln Gly Val Met Ala Thr Gly Lys His Phe Val Gly Tyr Gly Ala
210                 215                 220

Ser Glu Gly Gly Met Asn Trp Ala Pro Ala His Ile Pro Glu Arg Glu
225                 230                 235                 240

Leu Arg Glu Val Tyr Leu Phe Pro Phe Glu Ala Ala Val Arg Glu Ala
                245                 250                 255

Gly Leu Gly Ala Ile Met Pro Gly Tyr His Glu Leu Asp Gly Val Pro
                260                 265                 270

Cys His Asp Asn Pro Gly Leu Leu Arg Glu Thr Leu Arg Gly Arg Trp
            275                 280                 285

Gly Phe Gln Gly Leu Val Val Ser Asp Tyr Phe Ala Val Asn Gln Leu
290                 295                 300

Phe Glu Tyr His Gln Val Ala Arg Asp Lys Ala Glu Ala Ala Ala Leu
305                 310                 315                 320

Ala Val Arg Ala Gly Val Asp Val Glu Leu Pro Thr Arg Asp Val Tyr
                325                 330                 335

Gly Lys Pro Leu Ile Glu Ala Val Ala Arg Gly Leu Val Ser Pro Ala
                340                 345                 350

Glu Ile Asp Glu Leu Val Arg Arg Val Leu Thr Trp Lys Phe Arg Leu
            355                 360                 365

Gly Leu Phe Asp His Pro Phe Val Asp Glu Gly Ala Ala Ile Ala Val
370                 375                 380

Phe Asp Asn Ala Glu Gln Arg Gln Val Ala Arg Glu Ala Ala Glu Lys
385                 390                 395                 400

Ser Met Val Leu Leu Lys Asn Asp Gly Leu Leu Pro Leu Ala Pro Arg
                405                 410                 415

Gly Thr Ile Ala Val Ile Gly Pro Asn Ala His Thr Thr Arg Asn Leu
                420                 425                 430

Val Gly Asp Tyr Ala Tyr Pro Cys His Ile Glu Ser Leu Leu Glu Gln
            435                 440                 445

Ser Glu Asp Asn Val Phe Gln Thr Pro Leu Pro Ser Gly Val Lys His
450                 455                 460
```

```
Val Asp Glu Phe Ile Leu Met Arg Thr Ile Leu Glu Ala Ile Arg His
465                 470                 475                 480

Arg Val Gly Ser Glu Ala Gln Val Val Tyr Ala Lys Gly Cys Asp Ile
                485                 490                 495

Leu Gly Gly Glu Asp Ala Glu Leu Glu Ala Val Ala Leu Ala Ala
            500                 505                 510

Lys Ala Asp Val Ala Val Val Val Gly Asp Arg Ala Gly Leu Thr
        515                 520                 525

Asp Ala Cys Thr Thr Gly Glu Ser Arg Asp Arg Ala Thr Leu Ser Leu
        530                 535                 540

Ile Gly Arg Gln Glu Glu Leu Val Arg Arg Val Ile Ala Thr Gly Thr
545                 550                 555                 560

Lys Thr Val Val Val Leu Val Ser Gly Arg Pro Leu Ala Ile Pro Asp
                565                 570                 575

Ile Ala Glu Arg Ala Asn Ala Val Leu Glu Ala Trp Leu Pro Gly Glu
            580                 585                 590

Glu Gly Ala Glu Ala Val Ala Ala Val Leu Phe Gly Asp Val Asn Pro
        595                 600                 605

Ser Gly Lys Leu Pro Ile Thr Ile Pro Arg Ser Val Gly Gln Val Pro
    610                 615                 620

Ile Tyr Tyr Gly His Lys Pro Ser Gly Gly Arg Ser His Trp Lys Gly
625                 630                 635                 640

Ala Tyr Val Asp Glu Ser Asn Leu Pro Leu Tyr Pro Phe Gly His Gly
                645                 650                 655

Leu Ser Tyr Thr Ala Phe Ala Tyr Arg Asp Leu Ala Leu Ser Pro Ser
            660                 665                 670

Val Leu Gly Val His Gly Glu Val Glu Val Ser Cys Val Ile Glu Asn
        675                 680                 685

Val Gly Ala Arg Ala Gly Glu Glu Val Val Gln Leu Tyr Ala Arg Asp
    690                 695                 700

Val Ala Ala Asp Val Thr Arg Pro Val Lys Ala Leu Cys Gly Phe Ala
705                 710                 715                 720

Arg Val Ala Leu Ala Pro Gly Glu Lys Ala Arg Val Arg Phe Arg Val
                725                 730                 735

Ser Ala His Gln Phe Gly Phe Tyr Asn Arg Glu Met Arg Tyr Val Val
            740                 745                 750

Glu Pro Gly Glu Ile Glu Phe Met Val Gly Ala Ser Ser Glu Asp Ile
        755                 760                 765

Arg Leu Arg Gly Ala Val Arg Met Asp Gly Ala Val Thr Glu Ile Glu
    770                 775                 780

His Glu Lys Val Tyr Gln Ser Ala Val Asp Val Glu Arg Met
785                 790                 795
```